US007960377B2

(12) United States Patent
Newcom et al.

(10) Patent No.: US 7,960,377 B2
(45) Date of Patent: Jun. 14, 2011

(54) SUBSTITUTED PYRIDOXAZINES

(75) Inventors: Jason S. Newcom, Northford, CT (US); Stephen J. O'Connor, Guilford, CT (US); Gary R. Gustafson, Ridgefield, CT (US)

(73) Assignee: Cara Therapeutics, Inc., Shelton, CT (US)

( * ) Notice: Subject to any disclaimer, the term of this patent is extended or adjusted under 35 U.S.C. 154(b) by 220 days.

(21) Appl. No.: 12/409,626

(22) Filed: Mar. 24, 2009

(65) Prior Publication Data

US 2009/0247502 A1 Oct. 1, 2009

Related U.S. Application Data

(60) Provisional application No. 61/040,330, filed on Mar. 28, 2008.

(51) Int. Cl.
*C07D 403/04* (2006.01)
*C07D 487/04* (2006.01)
*A61K 31/5365* (2006.01)

(52) U.S. Cl. .................................... 514/230.5; 544/105

(58) Field of Classification Search ............... 514/230.5; 544/105
See application file for complete search history.

(56) References Cited

U.S. PATENT DOCUMENTS

2007/0191603 A1* 8/2007 Ackermann et al. ............ 544/50

FOREIGN PATENT DOCUMENTS

| | | | |
|---|---|---|---|
| WO | WO03032989 A1 | | 4/2003 |
| WO | WO2004052373 A1 | | 12/2006 |
| WO | WO2006134378 A1 | | 12/2006 |
| WO | WO 2007093507 A1 | * | 8/2007 |
| WO | WO2009120660 A3 | | 10/2009 |

OTHER PUBLICATIONS

Vippagunta et al, "Crystalline Solids" Advanced Drug Delivery Reviews, vol. 48, pp. 3-26 (2001).*

Hanus, O.L., *Discovery and Isolation of Anandamide and Other Endocannabinoids*, Chemistry and Biodiversity (2007), vol. 4: 1828-1841, Verlag Hely. Chim. Acta AG, Zurich.

Mackie, K., *Cannabinoid Receptors as Therapeutics Targets*, Annu. Rev. Pharmacol. Toxicol. (2006) vol. 46: 101-122.

Pertwee, R.G., *The Therapeutic Potential of Drugs That Target Cannabinoid Receptors or Modulate the Tissue Levels or Actions of Endocannabinoids*, AAPS Journal (2005) vol. 7(3) Article 64:E625-E654.

Raitio, K.H. et al., *Targeting the Cannabinoid CB2 Receptor: Mutations, Modeling and Development of CB2 Selective Ligands*, Curr. Med. Chem. (2005) vol. 12:1217-1237.

Mackie K. and Ross, R.A., *CB2 cannabinoid receptors: new vistas*, Br. J. Pharmacol. (2008) vol. 153:177-178.

* cited by examiner

*Primary Examiner* — Kahsay T Habte
(74) *Attorney, Agent, or Firm* — Algis Anilionis

(57) ABSTRACT

The invention provides compounds having the structure of formula I,

Formula I

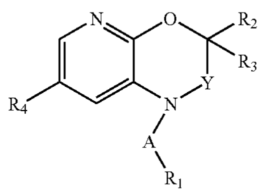

and prodrugs, stereoisomers, racemates, salts, hydrates, solvates, acid salt hydrates and isomorphic crystalline forms thereof, wherein A, Y and the groups $R_1$, $R_2$, $R_3$ and $R_4$ are defined in the specification. These compounds can be administered in pharmaceutical formulations to modulate cannabinoid receptor activity for the prevention and treatment of a variety of diseases and conditions, including pain, inflammation and pruritis.

20 Claims, No Drawings

SUBSTITUTED PYRIDOXAZINES

BACKGROUND OF THE INVENTION

Classical cannabinoids such as the marijuana-derived compound $\Delta^9$-tetra-hydro-cannabinol, ($\Delta^9$-THC) exert their pharmacological effects through interaction with specific members of the G-protein coupled receptor (GPCR) family. To date, two cannabinoid receptors have been cloned and characterized: CB1, a receptor found in the mammalian brain and to a lesser extent in peripheral tissues; and CB2, a receptor found primarily in the peripheral tissues, particularly in cells of the immune system. Several endogenous ligands for these cannabinoid receptors, known as endocannabinoids, have been identified (for a review see Hanus, L. O., *Discovery and isolation of anandamide and other endocannabinoids.*, Chem. Biodivers. (2007) 8:1828-41.)

Compounds that are modulators of one or both of the cannabinoid receptors have been shown to produce a variety of pharmacological effects that may be of therapeutic benefit in humans (see, for example, Mackie, K., *Cannabinoid receptors as therapeutic targets*, Ann. Rev. Pharmacol. Toxicol. (2006) 46: 101-122; Pertwee, R. G., *The therapeutic potential of drugs that target cannabinoid receptors or modulate the tissue levels or actions of endocannabinoids*, AAPS J. (2005) 7:E625-654). The cannabinoid receptor modulator can be an agonist, an inverse agonist or a neutral antagonist, and may interact at the same (orthosteric) site as the endogenous ligand, or at a different (allosteric) site.

Activation of the CB1 receptor in the brain is believed to mediate undesirable psycho-tropic effects associated with $\Delta^9$-THC and other centrally acting cannabinoid ligands. As a result, there has been considerable interest in developing compounds that possess high affinity and selectivity for the CB2 receptor (see for example, Raitio, K. H. et al., *Targeting the Cannabinoid CB2 Receptor: Mutations, Modeling and Development of selective CB2 ligands*, Curr. Med. Chem. (2005) 12: 1217-37). CB2 receptor agonists have shown efficacy in preclinical models of neuropathic and inflammatory pain and may also find application in cancer, multiple sclerosis, osteoporosis, Alzheimer's disease, liver disease and diabetes (Mackie, K.; Ross R A; *CB2 cannabinoid receptors: new vistas*, Br. J. Pharmacol. (2008) 153: 177-78 and references cited therein). There is an ongoing need to identify new cannabinoid receptor ligands that exhibit improved drug-like properties. In addition there is a need for new cannabinoid receptor ligands that are restricted to the periphery with low or minimal effects on the central nervous system (CNS).

SUMMARY OF THE INVENTION

The present invention provides compounds having the structure of formula I

I

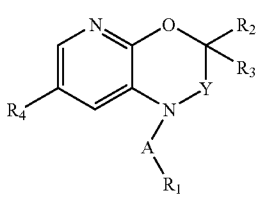

wherein the moiety A is chosen from $(CH_2)_n$, $CO(CH_2)_n$, and $SO_2(CH_2)_n$; and the moiety Y is chosen from $(CH_2)_p$ and CO.

The radical $R_1$ is chosen from $C_1$-$C_6$ alkyl, $C_3$-$C_8$ cycloalkyl, —$NR_5R_6$, aryl, and a 4- to 10-membered heterocyclyl, wherein the aryl of $R_1$ is optionally substituted with 1 to 5 substituents independently chosen from halogen, $C_1$-$C_6$ alkyl, $C_1$-$C_6$ alkoxy, O-aryl, CN, $NO_2$, $OCF_3$, and $CF_3$; and the 5- to 10-membered heterocyclyl of $R_1$ is optionally substituted with 1 to 3 substituents independently chosen from halogen, $C_1$-$C_6$ alkyl, $C_1$-$C_6$ alkoxy, CN, $NO_2$, $OCF_3$, and $CF_3$.

Radicals $R_2$ and $R_3$ are each independently chosen from H and $C_1$-$C_3$ alkyl; $R_4$ is $CONR_7R_8$, $COOR_8$, or

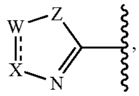, wherein W is chosen from N, $NR_{17}$, O, $CR_9R_{10}$, $CR_9R_{10}CR_{11}R_{12}$, and $CR_{13}$; X is chosen from N, $NR_{17}$, CO, $CR_{14}$, and $CR_{15}R_{16}$; and Z is chosen from $NR_{17}$, O, and S.

Radicals $R_5$ and $R_6$ are independently chosen from hydrogen, $C_1$-$C_6$ alkyl, $(CH_2)_nC_3$-$C_8$cycloalkyl, $(CH_2)_n$aryl, $(CH_2)_n$-5- to 10-membered heterocyclyl, wherein the aryl of the $(CH_2)_n$aryl and heterocycle of the $(CH_2)_n$-5- to 10-membered heterocyclyl of $R_5$ and $R_6$ are each optionally substituted with 1 to 5 substituents independently chosen from halogen, $C_1$-$C_6$alkyl, CN, $OCF_3$, and $CF_3$. Alternatively, $R_5$ and $R_6$, taken together with nitrogen atom to which they are bonded, form a 4- to 10-membered heterocyclyl that can be optionally substituted with 1 to 4 substituents independently chosen from halogen, $C_1$-$C_3$ alkyl, $CF_3$, aryl, 5- to 6-membered heterocyclyl, and $NR_{28}R_{29}$.

Radicals $R_7$ and $R_8$ are independently chosen from H, $C_1$-$C_6$ alkyl, $(CH_2)_nC_3$-$C_8$ cycloalkyl, $(CH_2)_n$aryl, $(CH_2)_n$-4- to 10-membered heterocyclyl, and $(CH_2)_qCR_{18}R_{19}R_{20}$, wherein the $(CH_2)_n$aryl, $(CH_2)_n$-linked 4- to 10-membered heterocyclyl of $R_7$ and $R_9$ are each optionally substituted with 1 to 4 substituents independently chosen from halogen, CN, $NO_2$, $CF_3$, $OCF_3$, $C_1$-$C_6$ alkyl, and $C_1$-$C_6$ alkoxy. Alternatively, $R_7$ and $R_8$, taken together with nitrogen atom to which they are bonded, form a 4- to 10-membered heterocyclyl optionally substituted with 1 to 3 substituents independently chosen from halogen, $CF_3$, $OCF_3$, $C_1$-$C_6$ alkyl, $C_1$-$C_6$ alkyl-$OR_{24}$, $COR_{24}$, $OR_{24}$, $(CH_2)_nCOOR_{24}$, $CONR_{24}R_{25}$, $(CH_2)_nNR_{24}R_{25}$, $SO_2R_{24}$, $SO_2NR_{24}R_{25}$, and 5- to 6-membered heterocyclyl.

I In formula I, each instance of the radicals, $R_9$, $R_{10}$, $R_{11}$, and $R_{12}$ is independently chosen from hydrogen and $C_1$-$C_6$ alkyl; $R_{13}$ is chosen from H, $C_1$-$C_6$ alkyl, $(CH_2)_n$—$C_3$-$C_8$ cycloalkyl, and aryl; $R_{14}$ is chosen from H, $C_1$-$C_6$ alkyl, $CONR_{26}R_{27}$, and aryl, wherein the aryl of $R_{14}$ is optionally substituted with 1 to 4 substituents independently chosen from halogen, $C_1$-$C_6$ alkyl, $C_1$-$C_6$ alkoxy, CN, $OCF_3$, and $CF_3$. Alternatively, $R_{13}$ and $R_{14}$, taken together with atoms to which they are bonded, form a 5- to 6-membered saturated, partially unsaturated, or unsaturated cycloalkyl, or a 5- to 7-membered heterocyclyl, each of which are optionally substituted with 1 to 3 substituents independently chosen from halogen and $C_1$-$C_3$ alkyl;

Each instance of $R_{15}$, $R_{16}$, and $R_{17}$ is independently chosen from hydrogen and $C_1$-$C_6$ alkyl. $R_{18}$ is chosen from hydrogen, $C_1$-$C_6$ alkyl, CN, $COR_{21}$, $(CH_2)_mOR_{22}$, $(CH_2)_mNR_{22}R_{23}$, $(CH_2)_nCOOR_{22}$, and $(CH_2)_nCONR_{22}R_{23}$.

Radical $R_{19}$ is chosen from hydrogen, $C_1$-$C_6$ alkyl, $(CH_2)_nC_3$-$C_8$ cycloalkyl, and $(CH_2)_mOR_{22}$. $R_{20}$ is chosen from hydrogen, $C_1$-$C_6$ alkyl, $(CH_2)_nC_3$-$C_8$ cycloalkyl, and aryl. $R_{21}$ is chosen from hydrogen, $C_1$-$C_6$ alkyl, $(CH_2)_nC_3$-$C_8$ cycloalkyl, and aryl.

In a first alternative of the compounds of formula I, $R_{19}$ and $R_{20}$, taken together with the atom to which they are bonded, form a 3- to 6-membered cycloalkyl or 4- to 7-membered heterocyclyl; wherein the 3- to 6-membered cycloalkyl or 4- to 7-membered heterocyclyl are each optionally substituted with 1 to 2 substituents independently chosen from halogen, $C_1$-$C_3$ alkyl, and $OR_{22}$. In a second alternative of the compounds of formula I, $R_{20}$ and $R_{21}$, taken together with atoms to which they are bonded, form a 5- to 7-membered cycloalkyl or 5- to 7-membered heterocyclyl.

Radical $R_{22}$ is chosen from hydrogen, $C_1$-$C_6$ alkyl, and $(CH_2)_nC_3$-$C_8$ cycloalkyl, and $R_{23}$ is chosen from hydrogen, $C_1$-$C_6$ alkyl, and $(CO)C_1$-$C_6$ alkyl. Alternatively, $R_{22}$ and $R_{23}$, taken together with the nitrogen atom to which they are bonded, form a 4- to 10-membered heterocyclyl optionally substituted with 1 to 3 substituents independently chosen from halogen, $CF_3$, $OCF_3$, $C_1$-$C_6$ alkyl, $C_1$-$C_6$ alkoxy, and $SO_2$—$C_1$-$C_6$ alkyl.

Radical $R_{24}$ is chosen from hydrogen, $C_1$-$C_6$ alkyl, $(CH_2)_nC_3$-$C_8$ cycloalkyl, aryl, and 4- to 10-membered heterocyclyl, wherein the aryl and 4- to 10-membered heterocyclyl are each optionally substituted with 1 to 3 substituents independently chosen from halogen, $CF_3$, $OCF_3$, $C_1$-$C_6$ alkyl, $C_1$-$C_6$ alkoxy; and $R_{25}$ is chosen from hydrogen, $C_1$-$C_6$ alkyl, and CO—$C_1$-$C_6$ alkyl. Alternatively, $R_{24}$ and $R_{25}$, taken together with the nitrogen atom to which they are bonded, form a 4- to 10-membered heterocyclyl.

Radicals $R_{26}$ and $R_{27}$ are independently chosen from hydrogen, $C_1$-$C_6$ alkyl, $(CH_2)_n$—$C_5$-$C_8$ cycloalkyl, and $C_2$-$C_8$ alkyloxyalkyl, or in another alternative of the compounds of formula I, $R_{26}$ and $R_{27}$, taken together with nitrogen atom to which they are bonded, form a 5- to 9-membered heterocyclyl.

Each instance of the radicals $R_{28}$ and $R_{29}$ is independently chosen from hydrogen and $C_1$-$C_6$ alkyl; alternatively, $R_{28}$ and $R_{29}$, taken together with the nitrogen to which they are bonded, form a 4-6 membered heterocyclyl optionally substituted with 1 to 4 substituents independently chosen from halogen and $C_1$-$C_6$ alkyl.

In formula I, the operator, p is 1 or 2; and each instance of n, m and q is independently chosen from 0 and an integer from 1 to 3. However, in the molecules of formula I of the invention, m and q are not both equal to zero. Similarly, if in formula I, the moiety A is $SO_2$, and $R_1$ is aryl or substituted aryl, and $R_7$ is hydrogen, then $R_8$ is not aryl, heteroaryl, substituted aryl, or substituted heteroaryl.

The present invention also provides prodrugs, stereoisomers, racemates, salts, hydrates, solvates, acid salt hydrates, and isomorphic crystalline forms of the compounds having the structure of Formula I. Also provided are pharmaceutical compositions that include a compound of formula I together with a pharmaceutically acceptable diluent, excipient, or carrier.

The invention further provides a method of prophylaxis or treatment of a cannabinoid receptor-associated disease or condition in a mammal, wherein the method includes administering a composition comprising an effective amount of a compound of formula I to a mammal in need thereof.

DETAILED DESCRIPTION OF THE INVENTION

The following definitions elucidate the meaning of the listed terms as used herein:

Alkyl—a saturated branched or straight chain monovalent hydrocarbon radical of up to about 8 carbon atoms. Thus, the term alkyl includes, but is not limited to, methyl, ethyl, propyl, isopropyl, n-butyl, t-butyl. A chain of 1-6 carbon atoms is also herein interchangeably designated as $C_1$-$C_6$ alkyl; a chain of 3 to 6 carbon atoms may be designated as $C_3$-$C_6$ alkyl, and so forth.

Alkenyl—refers to branched or straight chain hydrocarbon radical having at least one double bond. It should be noted that in an alkenyl substituted heterocycle, an unsaturated carbon atom cannot be bound directly to the nitrogen atom, i.e. there must be at least one saturated carbon atom intervening between the nitrogen atom and the nearest unsaturated carbon atom.

Alkynyl—refers to branched or straight chain hydrocarbon radical having at least one triple bond. It should be noted that in an alkynyl substituted heterocycle, the unsaturated carbon atom cannot be bound directly to the nitrogen atom, i.e. there must be at least one saturated carbon atom intervening between the nitrogen atom and the nearest unsaturated carbon atom.

Alkoxy—refers to an —O-alkyl substituent group linked through the oxygen atom and where the alkyl group is as defined above, such as for instance and without limitation, —O-methyl, O-ethyl, —O-propyl and so forth.

Alkoxyalkyl—refers to an alkyl-O-alkyl substituent group, such as for instance and without limitation, methoxyethylene (—$CH_2CH_2$—O—$CH_3$) or ethoxymethylene (—$CH_2$—O—$CH_2CH_3$) as examples of a $C_3$ alkoxyalkyl.

Cycloalkyl—a saturated monocyclic, polycyclic or bridged hydrocarbon ring system radical or linking group. A ring of 3 to 10 carbon atoms may be interchangeably designated as $C_3$-$C_{10}$ cycloalkyl; a ring of 3 to 7 carbon atoms may be designated as $C_3$-$C_7$cycloalkyl and so forth. Cycloalkyl typically includes, but is not limited to such saturated carbocycles as cyclopropyl, cyclobutyl, cyclopentyl, cyclohexyl, cycloheptyl, cyclooctyl and 1,3,3-trimethylbicyclo[2.2.1]heptyl.

Cycloalkenyl—a partially unsaturated monocyclic, polycyclic or bridged hydro-carbon ring system radical or linking group. Cycloalkenyl typically includes, but is not limited to, cyclobutenyl, cyclopentenyl, cyclohexenyl, cycloheptenyl and cyclooctenyl.

Heterocyclyl—a saturated, partially unsaturated or unsaturated monocyclic, polycyclic or bridged hydrocarbon ring system radical or linking group, wherein one or more ring carbon atoms have been replaced with one or more heteroatoms independently selected from N, O, or S. A heterocyclyl ring system further includes a ring system having up to 4 nitrogen atom ring members or a ring system having from 0 to 3 nitrogen atom ring members and up to two oxygen or sulfur atom ring members. A heterocyclyl radical is derived by the removal of one hydrogen atom from a single carbon or nitrogen ring atom. In addition, the sulfur atom can be in the (—S—), (—SO—) or (—$SO_2$—) oxidation state. Heterocyclyl includes, but is not limited to, furyl, thienyl, 2H-pyrrole, 2-pyrrolinyl, 3-pyrrolinyl, pyrrolidinyl, pyrrolyl, 1,3-dioxolanyl, oxazolyl, thiazolyl, imidazolyl, 2-imidazolinyl, imidazolidinyl, 2-pyrazolinyl, pyrazolidinyl, pyrazolyl, isoxazolyl, isothiazolyl, oxadiazolyl, triazolyl, thiadiazolyl, tetrazolyl, 2H-pyranyl, 4H-pyranyl, pyridinyl, piperidinyl, 1,4-dioxanyl, morpholinyl, 1,4-dithianyl, thiomorpholinyl, pyridazinyl, pyrimidinyl, pyrazinyl, piperazinyl, azepanyl, diazepinyl, indolizinyl, indolyl, isoindolyl, 3H-indolyl, indolinyl, benzo[b]furyl, benzo[b]thienyl, 1H-indazolyl, benzimidazolyl, benzothiazolyl, purinyl, 4H-quinolizinyl, quinolinyl, isoquinolinyl, cinnolinyl, phthalazinyl, quinazolinyl, quinoxalinyl, 1,8-napthyridinyl, pteridinyl, quinuclidinyl.

Alkylheterocyclyl—an optionally substituted heterocyclyl group bonded to the end carbon atom of $C_1$-$C_4$ alkyl group.

Aryl—an unsaturated, π-electron-conjugated monocyclic or polycyclic hydrocarbon ring system radical or linking group of 6, 10 or 14 carbon atoms. An aryl radical is derived by the removal of one hydrogen atom from a single carbon ring atom. Aryl includes, but is not limited to, phenyl, naphthalenyl, azulenyl, anthracenyl. Haloaryl—aryl with one or more halogen substituents.

Heteroaryl—an aromatic heterocycle such as pyrrolyl, pyrazolyl, imidazolyl, triazolyl, benzimidazolyl, benzoxazolyl, azabenzoxazolyl, oxazolyl, isoxazolyl, thiazolyl, isothiazolyl, furyl, thienyl, pyridyl, pyrazinyl or pyrimidinyl. It should be noted that as used herein, heteroaryl moieties are included in the definition of "heterocyclyl".

Alkylaryl—an optionally substituted aryl group bonded to the end carbon atom of $C_1$-$C_4$ alkyl group. Alkylaryl includes, but is not limited to, benzyl, phenylethyl, phenylpropyl and phenylbutyl.

Amino—a radical of the formula —$NH_2$, or a linking group of the formula —NH—. Aminoalkyl—a radical of the formula —NH-alkyl or —N(alkyl)$_2$. Aminosulfonylalkyl—a radical of the formula —$NHSO_2$-alkyl. Sulfonylaminoalkyl—a linking group of the formula —$SO_2$NH-alkyl- or a radical of the formula —$SO_2$N(alkyl)$_2$.

Alkylamide—a linking group of the formula -alkyl-C(O)NH— or a radical of the formula -alkyl-C(O)$NH_2$. Amidoalkyl—a linking group of the formula —NHC(O)-alkyl- or a radical of the formula —NHC(O)-alkyl.

Carboxy—a radical of the formula —COOH. Cyano—a radical of the formula —C≡N. Halogen—fluoro, chloro, bromo or iodo. Hydroxyl—OH. Oxo—a group of the formula =O in which the oxygen atom is double bonded to a carbon atom.

Abbreviations Used Herein:
AcOH acetic acid
Boc Butyloxy carboxyl
Burgess reagent methyl N-(triethylammoniumsulphonyl)carbamate
DBU 1,8-diazabicyclo[5.4.0]-undec-7-ene
DCM dichloromethane
DMF dimethylformamide
DCE 1,2-dichloroethane
DIBAL-H diisobutyl aluminum hydride
DIPEA N,N-diisopropylethylamine
DMAP 4-dimethylaminopyridine
DMSO dimethylsulfoxide
ESI electron spray ionization
EtOAc ethyl acetate
HCl hydrochloric acid
$^1$H-NMR proton nuclear magnetic resonance
HPLC high performance/pressure liquid chromatography
$K_3PO_4$ potassium phosphate
LC-MS liquid chromatography-mass spectrometry
LiOH lithium hydroxide
MeOH methanol
$NaHCO_3$ sodium carbonate
$Na_2SO_4$ sodium sulfate
$POCl_3$ phosphoryl trichloride
$PPh_3Cl_2$ dichloro(triphenyl)phosphorane
$SOCl_2$ thionyl chloride
TBAF tetrabutylammonium fluoride
TBAI tetrabutylammonium iodide
TBTU O-(benzotriazol-1-yl)-N,N,N',N'-tetramethyluronium tetrafluoroborate
TFA trifluoroacetic acid
THF tetrahydrofuran
TLC thin layer chromatography
TMS tetramethylsilane
TsOH p-toluenesulfonic acid
UPLC ultra performance/pressure liquid chromatography.

As used herein, the terms: a single compound, salt, polymorph, isomer, solvate are also interchangeably referred to in the plural form (i.e. compounds, salts, polymorphs, isomers and solvates).

The compounds of the present invention can contain one or more stereogenic centers, depending upon the location and nature of the various substituents desired. These stereogenic centers may be present in the (R) or (S) configuration, resulting in racemic mixtures and/or diastereomeric mixtures. Substituents on a partially or fully saturated ring may also be present in either cis or trans form. All such configurations (including enantiomers and diastereomers) of the compounds described or exemplified herein, are contemplated within the scope of the present invention. Compounds of the invention can also exist as individual stereoisomers or as mixtures in varying ratios (e.g. enantiomerically enriched or racemates). Enantiomeric mixtures of the compounds may be partially or fully resolved through standard purification and/or separation techniques known in the art, including but not limited to chiral chromatography (e.g. chiral derivatized solid phase), formation and separation of diastereomeric salts (e.g. tartaric acid salts or camphorsulfonic acid salts), or enzymatic separation. Diastereomeric mixtures may be separated by techniques well known in the art, based on their physical and/or chemical differences, or by methods described above.

In this specification, the term "salts of a compound of formula I" refers to a complex of the compound with an inorganic or organic counter ion or counter ions. For examples, see Handbook of Pharmaceutical Salts: Properties, Selection and Use; Stahl P. H., Wermuth, C. G., Eds.; John Wiley and Sons, 2002. Pharmaceutically useful salts include those obtained by treating the compound, functioning as a base, with an inorganic or organic acid to form a salt or salts. Additional pharmaceutically useful salts include those obtained by treating the compound, functioning as an acid, with an inorganic or organic base to form a salt or salts. Other pharmaceutically useful salts include those obtained by treatment of basic nitrogen-containing groups with such agents as alkyl halides (such as chlorides or bromides) to form a quaternary ammonium salt or salts.

As used herein, the term "solvates" describes a complex wherein the compound is coordinated with a stoichiometric or other proportional amount of a solvent molecule. Specific solvates, wherein the solvent is water, is referred to as hydrates.

Among the compounds described or exemplified herein are those which modulate a signal that regulates a biological activity, by acting as an agonist, a partial agonist, an inverse agonist or a neutral antagonist upon binding at a cannabinoid receptor such as CB2 and/or CB1. CB1 and CB2 receptors primarily couple to G proteins of the inhibitory G protein ($G_{j/o}$) class. The α subunits from these G proteins inhibit adenylyl cyclase and therefore CB1/CB2 agonists tend to reduce the intracellular concentration of cAMP, while inverse agonists increase the intracellular cAMP concentration.

In one embodiment, the invention provides a compound of the structure of formula I

I

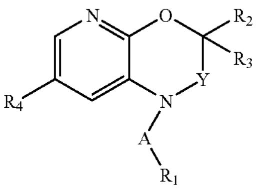

or a prodrug, stereoisomer, racemate, salt, hydrate, solvate, acid salt hydrate, or an isomorphic crystalline form thereof, wherein: A is selected from the group consisting of $(CH_2)_n$, $CO(CH_2)_n$, and $SO_2(CH_2)_n$; and Y is selected from the group consisting of $(CH_2)_p$ and CO.

In another embodiment, the invention provides a compound of the structure of formula I wherein the radical $R_1$ is $C_1$-$C_6$ alkyl, $C_3$-$C_8$ cycloalkyl, —$NR_5R_6$, aryl, or 4- to 10-membered heterocyclyl, wherein the aryl of $R_1$ is optionally substituted with 1 to 5 substituents independently chosen from halogen, $C_1$-$C_6$ alkyl, $C_1$-$C_6$ alkoxy, O-aryl, CN, $NO_2$, $OCF_3$, and $CF_3$; and the 5- to 10-membered heterocyclyl of $R_1$ is optionally substituted with 1 to 3 substituents independently selected from the group consisting of halogen, $C_1$-$C_6$ alkyl, $C_1$-$C_6$alkoxy, CN, $NO_2$, $OCF_3$, and $CF_3$.

In another embodiment, the invention provides a compound of the structure of formula I wherein the radicals $R_2$ and $R_3$ are each independently hydrogen or $C_1$-$C_3$ alkyl.

In another embodiment, the invention provides a compound of the structure of formula I wherein the radical $R_4$ is $CONR_7R_8$, $COOR_8$, or

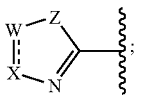

representing either:

(i)

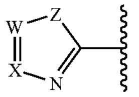

or (ii)

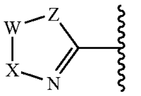

wherein the moiety, W is chosen from N, $NR_{17}$, O, $CR_9R_{10}$, $CR_9R_{10}CR_{11}R_{12}$, and $CR_{13}$; the moiety, X is chosen from N, $NR_{17}$, CO, $CR_{14}$, and $CR_{15}R_{16}$; and moiety, Z is $NR_{17}$, O, or S. It will be understood that the options for each of the moieties W and X in (i) are limited according to the valence of the ring atom(s) of the moiety: thus, in (i) W can be N or $CR_{13}$ but not O, $NR_{17}$, $CR_9R_{10}$ or $CR_9R_{10}CR_{11}R_{12}$; and X can be N or $CR_{14}$, but not $NR_{17}$, CO or $CR_{15}R_{16}$.

In still another embodiment, the radicals $R_5$ and $R_6$ are independently chosen from hydrogen, $C_1$-$C_6$ alkyl, $(CH_2)_nC_3$-$C_8$ cycloalkyl, $(CH_2)_n$aryl, and $(CH_2)_n$-5- to 10-membered heterocyclyl; wherein the aryl of $(CH_2)_n$aryl and heterocycle of $(CH_2)_n$-5- to 10-membered heterocyclyl of $R_5$ and $R_6$ are each optionally substituted with 1 to 5 substituents independently selected from the group consisting of halogen, $C_1$-$C_6$ alkyl, CN, $OCF_3$, and $CF_3$. Alternatively, $R_5$ and $R_6$, taken together with nitrogen atom to which they are bonded, form a 4- to 10-membered heterocyclyl optionally substituted with 1 to 4 substituents independently chosen from halogen, $C_1$-$C_3$ alkyl, $CF_3$, aryl, 5- to 6-membered heterocyclyl, and $NR_{28}R_{29}$.

In a further embodiment, the radicals $R_7$ and $R_8$ are independently chosen from hydrogen, $C_1$-$C_6$ alkyl, $(CH_2)_nC_3$-$C_8$ cycloalkyl, $(CH_2)_n$aryl, $(CH_2)_n$-4- to 10-membered heterocyclyl, and $(CH_2)_qCR_{18}R_{19}R_{20}$; wherein the $(CH_2)_n$aryl, $(CH_2)_n$-linked 4- to 10-membered heterocyclyl of $R_7$ and $R_8$ are each optionally substituted with 1 to 4 substituents independently chosen from halogen, CN, $NO_2$, $CF_3$, $OCF_3$, $C_1$-$C_6$ alkyl, and $C_1$-$C_6$ alkoxy. Alternatively, $R_7$ and $R_8$, taken together with nitrogen atom to which they are bonded, form a 4- to 10-membered heterocyclyl optionally substituted with 1 to 3 substituents independently chosen from halogen, $CF_3$, $OCF_3$, $C_1$-$C_6$ alkyl, $C_1$-$C_6$ alkyl-$OR_{24}$, $COR_{24}$, $OR_{24}$, $(CH_2)_nCOOR_{24}$, $CONR_{24}R_{25}$, $(CH_2)_nNR_{24}R_{25}$, $SO_2R_{24}$, $SO_2NR_{24}R_{25}$, and 5- to 6-membered heterocyclyl.

In another embodiment, each instance of the radicals $R_9$, $R_{10}$, $R_{11}$, and $R_{12}$ is independently chosen from hydrogen and $C_1$-$C_6$ alkyl; the radical $R_{13}$ is chosen from hydrogen, $C_1$-$C_6$ alkyl, $(CH_2)_n$—$C_3$-$C_8$ cycloalkyl, and aryl; the radical $R_{14}$ is chosen from hydrogen, $C_1$-$C_6$alkyl, $CONR_{26}R_{27}$, and aryl; wherein the aryl of $R_{14}$ is optionally substituted with 1 to 4 substituents independently chosen from halogen, $C_1$-$C_6$ alkyl, $C_1$-$C_6$ alkoxy, CN, $OCF_3$, and $CF_3$. Alternatively, $R_{13}$ and $R_{14}$, taken together with atoms to which they are bonded, form a 5- to 6-membered saturated, partially unsaturated, or unsaturated cycloalkyl, or a 5- to 7-membered heterocyclyl, each of which are optionally substituted with 1 to 3 substituents independently chosen from halogen and $C_1$-$C_3$ alkyl.

In another embodiment, each instance of the radicals $R_{15}$, $R_{16}$, and $R_{17}$ is independently chosen from hydrogen and $C_1$-$C_6$ alkyl; radical $R_{18}$ is chosen from hydrogen, $C_1$-$C_6$ alkyl, CN, $COR_{21}$, $(CH_2)_mOR_{22}$, $(CH_2)_mNR_{22}R_{23}$, $(CH_2)_nCOOR_{22}$, and $(CH_2)_nCONR_{22}R_{23}$; radical $R_{19}$ is chosen from hydrogen, $C_1$-$C_6$ alkyl, $(CH_2)_nC_3$-$C_8$ cycloalkyl, and $(CH_2)_mOR_{22}$; radical $R_{20}$ is chosen from hydrogen, $C_1$-$C_6$ alkyl, $(CH_2)_nC_3$-$C_8$ cycloalkyl, and aryl; and radical $R_{21}$ is chosen from hydrogen, $C_1$-$C_6$ alkyl, $(CH_2)_nC_3$-$C_8$ cycloalkyl, and aryl. Alternatively, either (i) $R_{19}$ and $R_{20}$, taken together with the atom to which they are bonded, form a 3- to 6-membered cycloalkyl or 4- to 7-membered heterocyclyl; wherein the 3- to 6-membered cycloalkyl or 4- to 7-membered heterocyclyl are each optionally substituted with 1 to 2 substituents independently chosen from halogen, $C_1$-$C_3$ alkyl, and $OR_{22}$; or (ii) $R_{20}$ and $R_{21}$, taken together with atoms to which they are bonded, form a 5- to 7-membered cycloalkyl or 5- to 7-membered heterocyclyl.

In another embodiment, radical $R_{22}$ is chosen from hydrogen, $C_1$-$C_6$ alkyl, and $(CH_2)_nC_3$-$C_8$ cycloalkyl; and $R_{23}$ is chosen from hydrogen, $C_1$-$C_6$ alkyl, and $(CO)C_1$-$C_6$ alkyl. Alternatively, radicals $R_{22}$ and $R_{23}$, taken together with the nitrogen atom to which they are bonded, form a 4- to 10-membered heterocyclyl optionally substituted with 1 to 3 substituents independently is chosen from halogen, $CF_3$, $OCF_3$, $C_1$-$C_6$ alkyl, $C_1$-$C_6$ alkoxy, and $SO_2$—$C_1$-$C_6$alkyl.

In still another embodiment, radical $R_{24}$ is chosen from hydrogen, $C_1$-$C_6$ alkyl, $(CH_2)_nC_3$-$C_8$ cycloalkyl, aryl, and 4- to 10-membered heterocyclyl, wherein the aryl and 4- to 10-membered heterocyclyl are each optionally substituted with 1 to 3 substituents independently chosen from halogen, $CF_3$, $OCF_3$, $C_1$-$C_6$ alkyl, and $C_1$-$C_6$ alkoxy; $R_{25}$ is chosen from hydrogen, $C_1$-$C_6$ alkyl, and CO—$C_1$-$C_6$ alkyl. Alternatively, $R_{24}$ and $R_{25}$, taken together with the nitrogen atom to which they are bonded, form a 4- to 10-membered heterocyclyl.

In still yet another embodiment, the radicals $R_{26}$ and $R_{27}$ are independently chosen from hydrogen, $C_1$-$C_6$ alkyl, $(CH_2)_n$—$C_5$-$C_8$ cycloalkyl, and $C_2$-$C_8$ alkyloxyalkyl, or $R_{26}$ and $R_{27}$, taken together with nitrogen atom to which they are bonded, form a 5- to 9-membered heterocyclyl.

In another embodiment, each instance of $R_{28}$ and $R_{29}$ is independently chosen from hydrogen and $C_1$-$C_6$ alkyl. Alternatively, $R_{28}$ and $R_{29}$, taken together with the nitrogen to which they are bonded, form a 4-6 membered heterocyclyl optionally substituted with 1 to 4 substituents independently chosen from halogen and $C_1$-$C_6$ alkyl.

In one embodiment of the compounds of the present invention, the operator p is 1 or 2; and each instance of n, m and q is independently 0 or an integer from 1 to 3. In another embodiment, m and q are not both zero.

In another embodiment, when the moiety A of formula I is $SO_2$, and $R_1$ is aryl or substituted aryl, and $R_7$ is hydrogen, then $R_8$ is not aryl, heteroaryl, substituted aryl, or substituted heteroaryl.

In a further embodiment of the compounds of the present invention, the radical $R_1$ is aryl, optionally substituted with 1 to 3 substituents independently chosen from halogen, $C_1$-$C_6$alkyl, $C_1$-$C_6$ alkoxy, and $CF_3$; and radicals, $R_2$ and $R_3$ are both hydrogen. In another embodiment, $R_4$ is $CONR_7R_8$.

In another embodiment, $R_5$ and $R_6$ are each independently chosen from $C_1$-$C_6$ alkyl, $(CH_2)_n$aryl, 5- to 10-membered heterocyclyl, wherein the aryl of $(CH_2)_n$aryl and the 5- to 10-membered heterocyclyl of $R_5$ and $R_6$ are each optionally substituted with 1 to 5 substituents independently chosen from halogen, $C_1$-$C_6$ alkyl, CN, $OCF_3$, and $CF_3$.

In still another embodiment, $R_5$ and $R_6$, taken together with nitrogen atom to which they are bonded, form a 4- to 10-membered heterocyclyl optionally substituted with 1 to 4 substituents independently chosen from halogen, $C_1$-$C_3$ alkyl, $CF_3$, aryl, 5- to 6-membered heterocyclyl, and $NR_{28}R_{29}$.

In still a further embodiment, $R_2$ and $R_3$ are both hydrogen; $R_4$ is $CONR_7R_8$, and $R_7$ is chosen from hydrogen and $C_1$-$C_6$ alkyl.

In another embodiment of the compounds of formula I, $R_2$ and $R_3$ are both hydrogen; and $R_4$ is

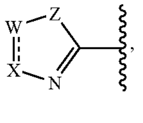

wherein the moiety, X is chosen from nitrogen, $CR_{14}$, and $CR_{15}R_{16}$; and the moiety, Z is chosen from $NR_{17}$ and oxygen.

In another embodiment, the moiety, W is $CR_{13}$, X is chosen from nitrogen and $CR_{14}$; and Z is chosen from $NR_{17}$ and oxygen, and radicals $R_{13}$ and $R_{14}$, taken together with atoms to which they are bonded, form a 5- to 6-membered partially unsaturated, or unsaturated cycloalkyl, or a 5- to 7-membered heterocyclyl, each of which are optionally substituted with 1 to 3 substituents independently chosen from halogen and $C_1$-$C_3$ alkyl.

In another embodiment the moiety, W is oxygen and the moiety, Z is NH. In still another embodiment the moiety, W is O, the moiety, X is $CR_{14}$; and the moiety, Z is nitrogen.

In another embodiment of the compounds of formula I, the moiety, A is $SO_2$; the radical $R_1$ is $NR_5R_6$; $R_2$ and $R_3$ are each independently chosen from hydrogen and $CH_3$; $R_4$ is $CONHR_8$; and $R_8$ is chosen from $C_1$-$C_6$ alkyl and $(CH_2)_q CR_{18}R_{19}R_{20}$; wherein $R_{18}$ is chosen from $(CH_2)_mOR_{22}$, $(CH_2)_nCOOR_{22}$, and $(CH_2)_nCONR_{22}R_{23}$; and $R_{19}$ and $R_{20}$ are each independently chosen from $C_1$-$C_6$ alkyl.

In another embodiment of the compounds of formula I, the moiety, A is $SO_2$; the radical $R_1$ is aryl optionally substituted with 1 to 5 substituents independently chosen from halogen, $C_1$-$C_6$ alkyl, CN, $OCF_3$, and $CF_3$; $R_2$ and $R_3$ are each independently chosen from hydrogen and $CH_3$; $R_4$ is $CONHR_8$; and $R_8$ is chosen from $C_1$-$C_6$ alkyl $(CH_2)_qCR_{18}R_{19}R_{20}$; wherein $R_{18}$ is chosen from $(CH_2)_mOR_{22}$, $(CH_2)_nCOOR_{22}$, and $(CH_2)_nCONR_{22}R_{23}$; and $R_{19}$ and $R_{20}$ are each independently chosen from $C_1$-$C_6$ alkyl.

In still another embodiment of the compounds of formula I, the moiety, A is chosen from $CH_2$ and $SO_2$; the radical $R_1$ is chosen from $C_1$-$C_6$ alkyl, aryl, haloaryl, and $CF_3$aryl; $R_2$ and $R_3$ are each independently selected from the group consisting of hydrogen and $CH_3$; and $R_4$ is

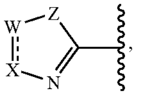

wherein the moiety, X is chosen from nitrogen, $CR_{14}$, and $CR_{15}R_{16}$; and the moiety, Z is chosen from $NR_{17}$ and oxygen.

In still a further embodiment of the compounds of formula I, the moiety, A is chosen from $CH_2$ and $SO_2$; the radical $R_1$ is $NR_5R_6$; $R_2$ and $R_3$ are each independently chosen from hydrogen and $CH_3$; and $R_4$ is

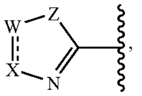

wherein the moiety, X is chosen from nitrogen, $CR_{14}$, and $CR_{15}R_{16}$; and the moiety, Z is chosen from $NR_{17}$ and oxygen.

It will be understood that the invention contemplates tautomeric forms of the compounds of formula I. Further, when n=0, the linker $(CH_2)_n$ represents a bond.

In certain embodiments the compounds of the present invention bind one or more cannabinoid receptors such as, without limitation the CB1 receptor or the CB2 receptor. The cannabinoid receptors are generally defined as the group of G protein-coupled receptors that bind the group of substances that are structurally related to Δ9-tetrahydrocannabinol (THC).

In certain embodiments, the compounds of the present invention have an $EC_{50}$ for a CB receptor in a range of from about 0.1 nM to about 30 μM. In other embodiments, the compounds have an $EC_{50}$ for a CB receptor of from about 0.1 nM to about 3 μM. In further embodiments, the compounds have an $EC_{50}$ for a CB receptor of from about 0.1 nM to about 300 nM.

In this specification, salts of a compound of formula I refers to a complex of the compound with an inorganic or organic counter ion or counter ions. For examples, see Handbook of Pharmaceutical Salts: Properties, Selection and Use; Stahl P. H., Wermuth, C. G., Eds.; John Wiley and Sons, 2002. Pharmaceutically useful salts include those obtained by treating the compound, functioning as a base, with an inorganic or organic acid to form a salt or salts. Additional pharmaceutically useful salts include those obtained by treating the compound, functioning as an acid, with an inorganic or organic base to form a salt or salts. Other pharmaceutically useful salts include those obtained by treatment of basic nitrogen-containing groups with such agents as alkyl halides (such as chlorides or bromides) to form a quaternary ammonium a salt or salts.

In certain embodiments, the compounds of the present invention are useful as therapeutic and/or prophylactic agents for the treatment or prevention of a cannabinoid-associated disease or condition. An effective amount of the compound, prodrug, stereoisomer, racemate, salt, hydrate, solvate, acid salt hydrate, or an isomorphic crystalline form of a compound of the present invention can be administered to a mammal in need of such treatment or prophylaxis in order to manage, ameliorate, treat, cure or prevent such a disease or condition. The term "cannabinoid-associated disease or condition" as used herein means a disease or condition that is treatable by therapeutic compounds that act directly or indirectly on a cannabinoid receptor. In particular embodiments, the compounds of the present invention are useful as therapeutic and/or prophylactic agents for the treatment or prevention of a CB-associated disease or condition. These compounds can be administered to a mammal in need of such treatment or prophylaxis in order to manage, ameliorate, treat, cure or prevent a CB-associated disease or condition. The term "CB-associated disease or condition" as used herein means a disease or condition that is treatable by therapeutic compounds that act directly or indirectly on a CB receptor.

Such cannabinoid-associated disease or conditions that can be managed, ameliorated, treated, inhibited, cured or prevented by administration of compounds or pharmaceutical compositions of the present invention include, but are not limited to: pain, inflammation and pruritis (itching).

The compounds and pharmaceutical compositions of the present invention can be administered to treat or prevent pain of a variety of origins, such as inflammatory pain, visceral pain, postoperative pain, metastatic cancer pain, break-through cancer pain, neuropathic pain, musculoskeletal pain, dysmenorrhea (menstrual pain), migraine and headache. Neuropathic pain includes pain due to diabetic neuropathy, fibromyalgia, lower back pain, sciatica, and pain from physical trauma, cancer, amputation, toxins or chronic inflammatory conditions. Other forms of pain preventable or treatable by compounds and pharmaceutical compositions of the present invention include, for instance, virally-induced pain, chemotherapy-induced pain, somatic pain, cutaneous pain, ocular/otitic pain and gastrointestinal pain.

The compounds and pharmaceutical compositions of the present invention are also useful for the treatment and prevention of inflammatory diseases and conditions. These include for instance, inflammation due to rheumatoid arthritis, systemic lupus erythematosus, Crohn's disease, psoriasis, eczema, multiple sclerosis, diabetes and thyroiditis, as well as ocular and otic inflammation.

The compounds and pharmaceutical compositions of the present invention are also useful in the treatment and prevention of pruritis. The pruritis may be due to atopic dermatitis, eczema, or insect bites. Other forms of pruritis treatable or preventable by the compounds and pharmaceutical compositions of the present invention include ocular and/or otic pruritis, kidney dialysis-induced pruritis and opioid-induced pruritis.

The compounds and pharmaceutical compositions of the present invention are also useful in the treatment and prevention of skin disorders (e.g. sunburn, dermatitis, pruritis); lung disorders (e.g. chronic obstructive pulmonary disease, cough, asthma, bronchitis); ophthalmic disorders (e.g. glaucoma, retinitis, reinopathies, uveitis, conjunctivitis); gastrointestinal disorders (e.g. ulcerative colitis, irritable bowel syndrome, coeliac disease, inflammatory bowel disease, gastroesophageal reflux disease, organ transplant, nausea, emesis); cardiovascular disorders (e.g. stroke, cardiac arrest, atherosclerosis, myocardial ischemia); neurodegenerative, neuroinflammatory or psychiatric disorders (e.g. senile dementia, Alzheimer's disease, vascular dementia, amyotrophic lateral sclerosis, neuroinflammation, tinnitus); bladder disorders (e.g. bladder hyper-reflexia, cystitis) and cancer, such as for instance, lymphoblastic leukemia and lymphoma, acute myelogenous leukemia, chronic lymphocytic leukemia, glioma, skin cancer, breast cancer, prostate cancer, liver cancer, kidney cancer, lung cancer, pancreatic cancer.

In addition, compounds and pharmaceutical compositions of the present invention can be used to modulate bone formation and/or resorption for treating certain conditions including, but not limited to, ankylosing spondylitis, gout, arthritis associated with gout, osteoarthritis and osteoporosis.

The compounds of the present invention can be administered as pharmaceutical compositions in readily available formulations in solid or liquid form. Solid formulations can include optional inactive fillers, carriers or diluents and can be formed into tablets or encapsulated for oral delivery. Liquid formulations include solutions, suspensions and slurries suitable for oral, topical or parenteral routes of administration.

The compounds and pharmaceutical compositions of the present invention can be delivered by any of the standard routes, for example orally, parentarally, sublingually, dermally, transdermally, rectally, via inhalation, or by buccal, nasal, ocular or otic administration.

General Methods

All reactions involving moisture sensitive compounds were carried out under an anhydrous nitrogen or argon atmosphere. All reagents were purchased from commercial sources and used without further purification. Unless otherwise noted, the starting materials used in the examples were obtained from readily available commercial sources or synthesized by standard methods known to those skilled in the art of organic synthesis. Reactions performed under microwave irradiation conditions were carried out in a Biotage Initiator® 60 microwave system (Charlottesville, Va.; model#10986-22V) with a 300 watt magnetron. Normal phase chromatography and reverse phase chromatography was performed on an ISCO CombiFlash® Companion® or CombiFlash® Companion/TS® system (Teledyne Isco, Inc., Lincoln, Nebr.). Reverse phase chromatography was also performed on a Waters Autopurification System with 3100 Mass Detector. The HPLC column was a Waters XBridge C18 5 μm OBD 19×150 mm; eluants were A: water with 0.1% formic acid and B: acetonitrile with 0.1% formic acid. Gradient elution was from 5% B-95% B. The total run time was 13 minutes. Mass spectra (MS) data were acquired on the Waters SQ Detector/3100 Mass detector using electrospray techniques or a Waters ZQ mass spectrometer with a Waters 600 HPLC pump and a 2487 UV detector and a 1525u binary LC pump with integrated degasser.

Compounds were characterized by their LCMS-Electrospray/chemical ionization mass spectra (LC ESCI-MS) on one of the following systems:

1. Waters HPLC-MS system (Waters Corp., Milford, Mass.) equipped with a 2767 Sample Manager, 2545 Binary Gradient Module, SFO System Fluidics Organizer, 2996 Photodiode Array Detector and 3100 Mass Detector. Data were collected across a range of wavelengths from 220 nm to 280 nm in positive ESCI mode. Spectra were scanned from 100-1400 atomic mass units (amu). The HPLC column was a Waters XBridge C18 3.5 μm 4.6×30 mm; eluants were A: water with 0.1% formic acid and B: acetonitrile with 0.1% formic acid. Gradient elution was from 5% B to 95% B over 2.3 minutes with an initial hold of 0.2 minutes and a final hold at 95% B of 0.5 minutes. Total run time was 4 minutes.

2. Waters (Waters Corporation, Milford, Mass.) UPLC-MS system equipped with an Acquity Sample Manager, Acquity Binary Solvent Manager, Acquity Photodiode Array Detector, Acquity Evaporative Light Scattering Detector and SQ Detector. Data were collected at 220 nm and 254 nm and in positive electrospray-chemical ionization mode. The UPLC column used was a Waters Acquity UPLC BEH C18 1.7 μm 2.1×50 mm. Spectra were scanned from 100-1400 amu. The eluants were A: water with 0.1% formic acid and B: acetonitrile with 0.1% formic acid. Gradient elution from 5% B to 95% B over 0.8 minutes was used with a final hold at 95% B of 0.2 minutes at a flow rate of 0.8 milliliters per minute. Total run time was 1.5 minutes.

Nuclear magnetic resonance spectra were recorded using a Bruker Avance III (400 MHz shielded) spectrometer equipped with a Gradient Multinuclear Broadband Fluorine Observe (BBFO) probe. Spectra were acquired in the indicated solvent. Chemical shifts (δ) are given in ppm (parts per million upfield or downfield from TMS defined as 0 ppm). Coupling constants J are in hertz (Hz). Peak shapes in the NMR spectra are indicated by symbols 'q' (quartet), 't' (triplet), 'd' (doublet), 's' (singlet), 'br s' (broad singlet), 'br' (broad) 'm' (multiplet) and 'dd' (doublet of doublets).

Synthetic Schemes

Compounds of the present invention can be prepared according to the non-limiting synthetic schemes outlined in the general Schemes 1 to 11 shown below.

One series of compounds of the invention can be readily synthesized from intermediate 1-8. Intermediate 1-8 can be prepared as shown in scheme 1.

Nucleophilic aromatic substitution of methyl 6-chloro-5-nitronicotinate (1-1) is effected by treatment with a nucleophile, 1-2, in a polar aprotic solvent, such as DMF or an organic solvent mixture that includes DMF, such as for instance, THF/DMF, in the presence of a base such as an inorganic carbonate.

Scheme 1

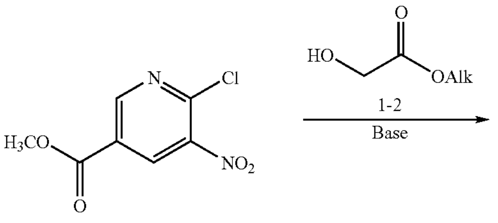

1-1

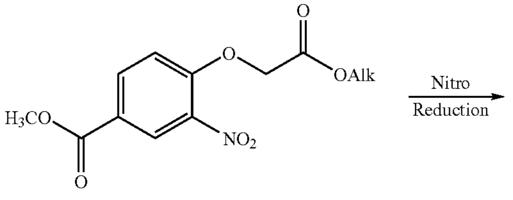

1-3

-continued

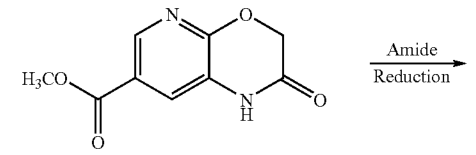

1-4

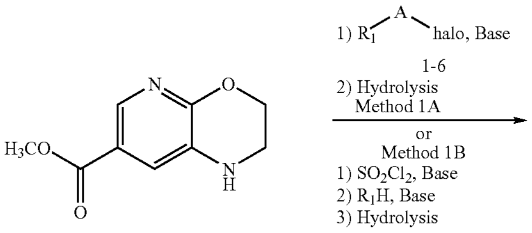

1-5

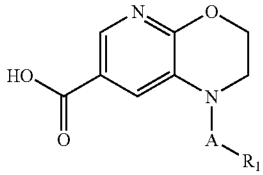

1-7

Chlorination

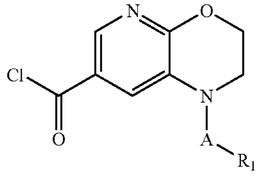

1-8

Reduction of the nitro moiety in intermediate 1-3 occurs under a variety of metal mediated conditions, including, but not limited to iron in acidic media, palladium-catalyzed hydrogenation, and tin(II) chloride in alcoholic solvents. Under the reaction conditions, cyclization occurs concomitantly with reduction to provide intermediate, 1-4. Selective reduction of lactam 1-4 can be effected with a reducing agent, such as borane, in an aprotic ethereal solvent. Intermediate 1-5 is then coupled with intermediate 1-6 (Method 1A, A=$SO_2$, CO) in the presence of a tertiary amine base and/or DMAP in a solvent such as DCM. Subsequent hydrolysis of the methyl ester under basic conditions (e.g. LiOH in a THF/MeOH/Water mixture) provides intermediate 1-7.

Alternatively, intermediate 1-5 can also be treated with sulfuryl chloride (Method 1B) in the presence of a tertiary amine base in aprotic solvents such as $CHCl_3$. The resulting sulfamoyl chloride is treated with $R^1H$ (when $R^1$=$NR_5R_6$) Synthesis of intermediate 1-8 is completed by treatment of intermediate 1-7 with a chlorinating reagent, such as $SOCl_2$ in an aprotic solvent, such as toluene or 1,2-dichloroethane at elevated temperatures (such as, for instance, at 70° C.).

Scheme 2

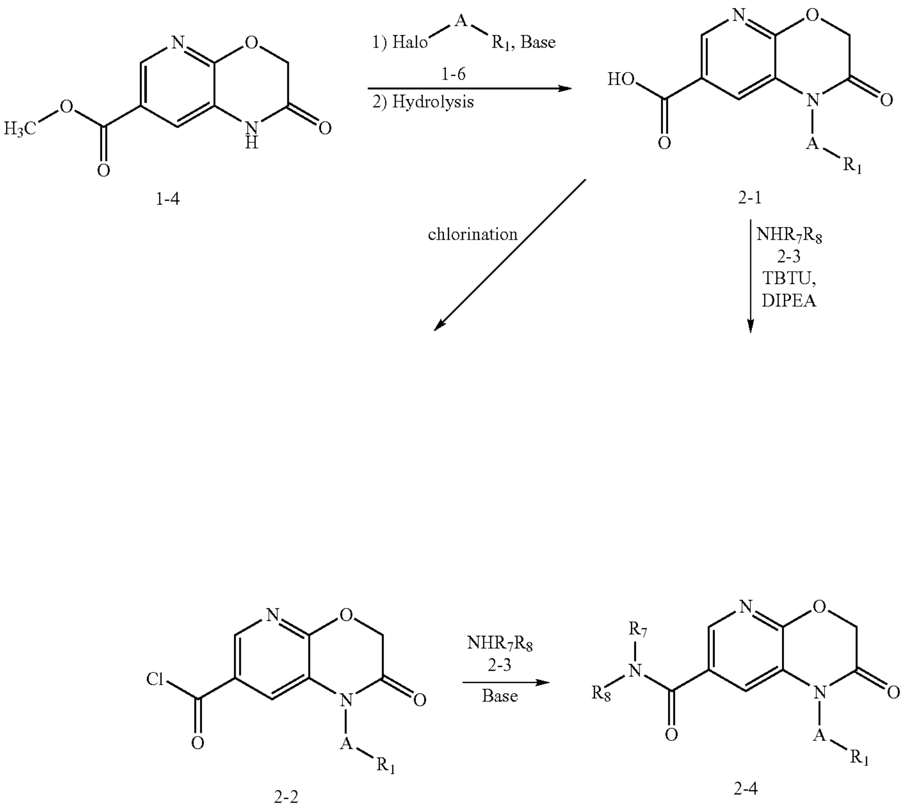

Additionally, intermediate 1-4 can be used to complete the synthesis of compounds of 2-4 shown in Scheme 2. Intermediate 1-4 is coupled with intermediate 1-6 ($A=CH_2$) in the presence of a carbonate base and/or iodine salt (e.g. TBAI) in a polar aprotic solvent such as DMF. This reaction is followed by hydrolysis of the methyl ester under basic conditions (e.g. LiOH in a THF/MeOH/water mixture) provides intermediate 2-1. Amide 2-4 is produced by directly coupling with a peptide-coupling reagent, such as, for example TBTU, in the presence of a tertiary amine in a polar aprotic solvent (e.g. DMF). Alternatively, 2-4 can be prepared through a two-step procedure also outlined in Scheme 2. Intermediate 2-1 is treated with a chlorinating reagent, such as $SOCl_2$ in an aprotic solvent, such as toluene or 1,2-dichloroethane at elevated temperatures (such as, for instance, at 70° C.) to provide intermediate 2-2. Intermediate 2-2 is then treated with amine 2-3 in an organic solvent such as DCM in the presence of aqueous carbonate base to provide compounds having the structure of 2-4.

Scheme 3

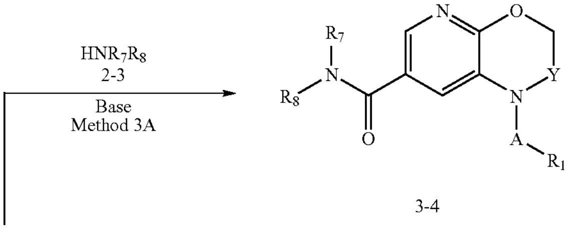

-continued

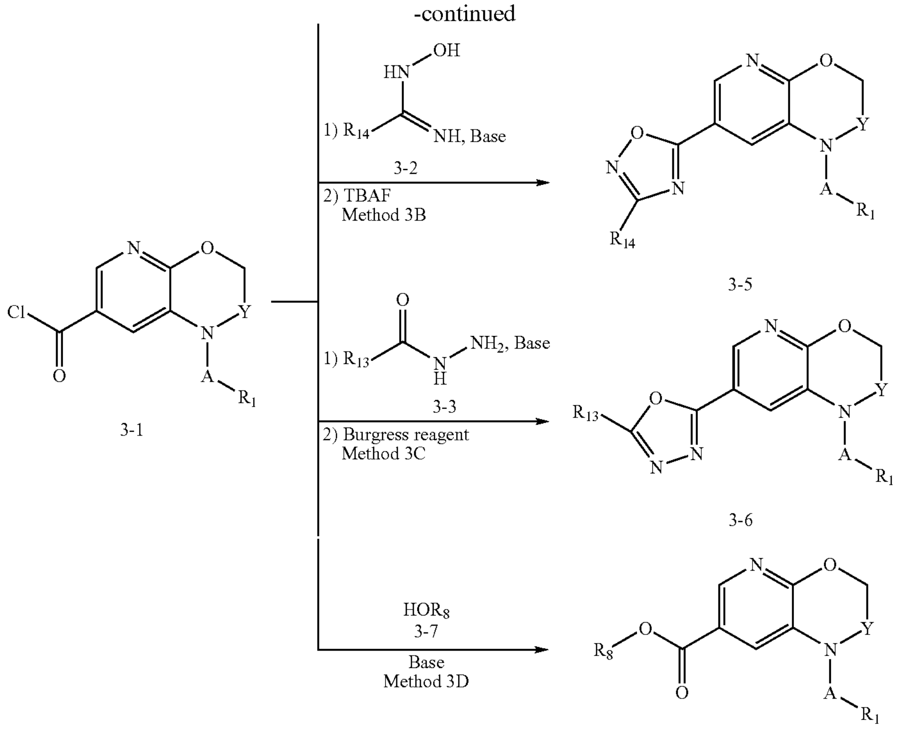

3-1

3-5

3-6

3-8

Intermediate 3-1 (having the structure of compound 1-8 or 2-2, wherein Y═$CH_2$or C═O respectively) can be used to complete the synthesis of compounds 3-4, 3-5 and 3-6 as depicted in Scheme 3. The methods shown in scheme 3 can also be used for the synthesis of 1,2,3,4-tetrahydropyrido[2,3-b][1,4]oxazepine compounds, wherein Y═$(CH_2)_2$. For example, treatment of intermediate 3-1 with amine 2-3 ($HNR_7R_8$) in DCM in the presence of an aqueous bicarbonate solution (Method 3A) provides 3-4 directly.

Alternatively, compounds having the structure of 3-5 can be derived from intermediate 3-1 through a two step process shown in Method 3B. Treatment of intermediate 3-1 with a substituted hydroxyimidamide (3-2) in the presence of a tertiary amine base in aprotic solvents such as DCM, followed by treatment of the resulting intermediate with TBAF in an ethereal solvent such as THF provides substituted 1,2,4-oxadiazolyl compounds 3-5.

Compounds 3-6 can be derived from intermediate 3-1 through a two step process outlined in Method 3C. The two step procedure begins with the treatment of intermediate 3-1 with a substituted hydrazide (3-3) in the presence of a tertiary amine base in an aprotic solvent, such as DCM. Cyclization of the resulting intermediate is effected with Burgess reagent in a polar aprotic solvent such as DMF at elevated temperatures, by, for instance, heating to 180° C. using microwave irradiation.

Additionally compounds having the structure 3-8 can be derived from intermediate 3-1 by treatment of intermediate 3-1 with alcohol 3-7 ($HOR_8$) in DCM in the presence of an aqueous bicarbonate solution or tertiary amine base (Method 3D).

Scheme 4 (below) outlines the process for the synthesis of compounds having the structure of 4-5. The synthesis begins with intermediate 4-1 (compound 3-5 wherein $R_{13}$═$CO_2Et$). Hydrolysis of the ester 4-1 under basic conditions (such as LiOH in a THF/MeOH/water mixture) provides acid 4-2.

Activation of the acid to a suitable coupling partner is accomplished by treating intermediate 4-2 with a chlorinating reagent, such as $SOCl_2$ in an aprotic solvent, such as toluene or 1,2-dichloroethane at elevated temperatures (such as, for instance, at 70° C.). In the final step, intermediate 4-3 is treated with amine 4-4 ($HNR_{26}R_{27}$) in DCM in the presence of an aqueous bicarbonate solution to provide compound 4-5.

Scheme 4

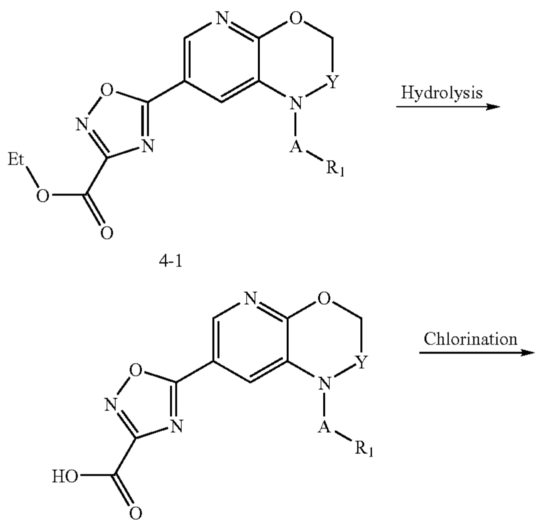

4-1

4-2

-continued

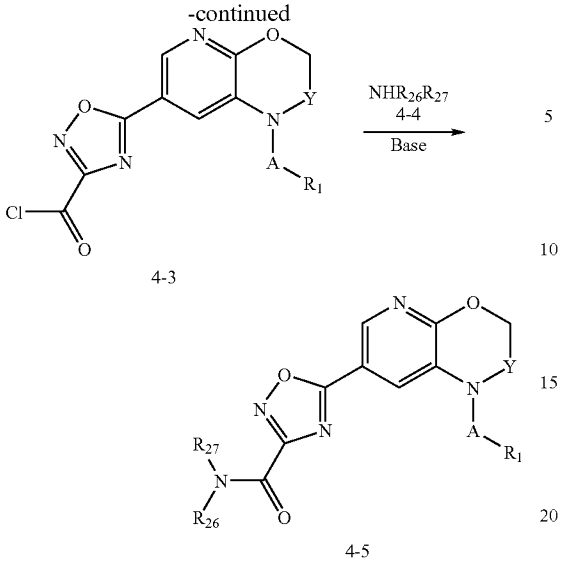

Scheme 5 (below) outlines the synthesis of 5-membered heterocyclic derivatives having the structure of 5-5. Intermediate 3-1 is coupled with an α-aminocarbonyl compound, 5-1 or 5-3, in a solvent such as DCM under basic conditions (such as, for example, aqueous carbonate or tertiary amine) to provide intermediate 5-2, or compound 5-4, respectively. Compound 5-4 is formed from intermediate 5-2 by addition of nucleophile $R_{21}$-M (such as a Grignard reagent, or a metal hydride reagent, or other nucleophile). Cyclization providing compounds of the formula 5-5 (Method 5A) is accomplished under dehydration conditions (such as, for example, $POCl_3$, $PPh_3Cl_2$, then DBU or Burgess Reagent under microwave irradiation). Alternatively (Method 5B), treatment of intermediate 5-4 with an amine ($H_2NR_{17}$) in mildly acidic solutions (e.g. ammonium acetate or methyl amine and TsOH in DMF) at elevated temperatures (such as, for instance, at 100-150° C.) affords compounds of the formula 5-6.

Scheme 5

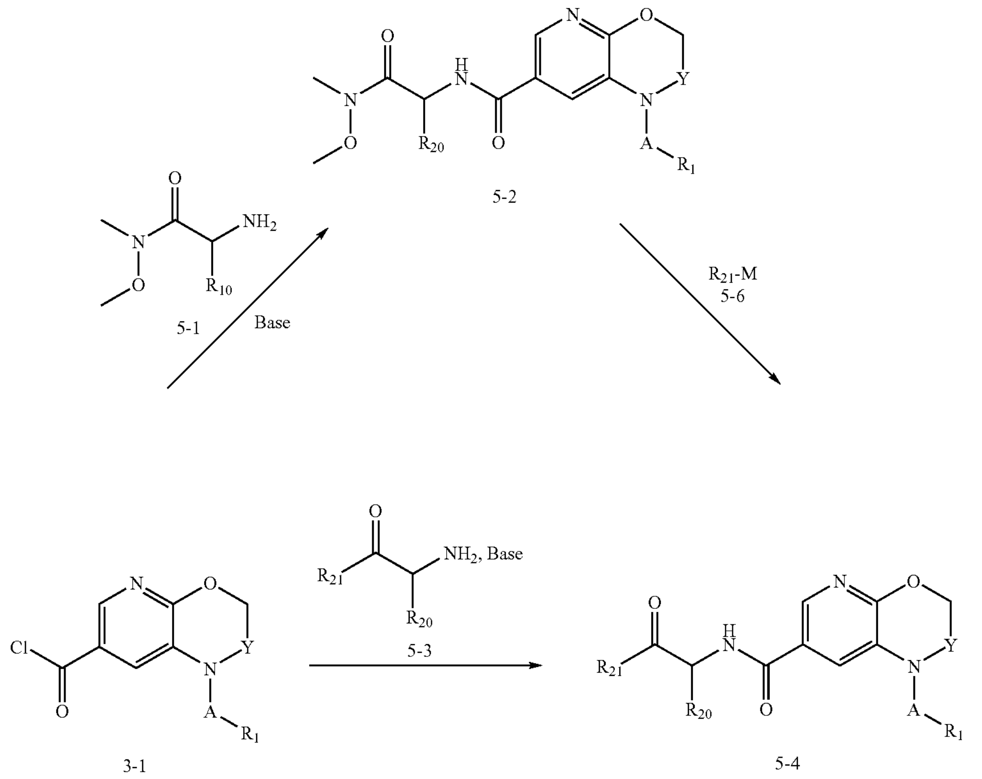

-continued

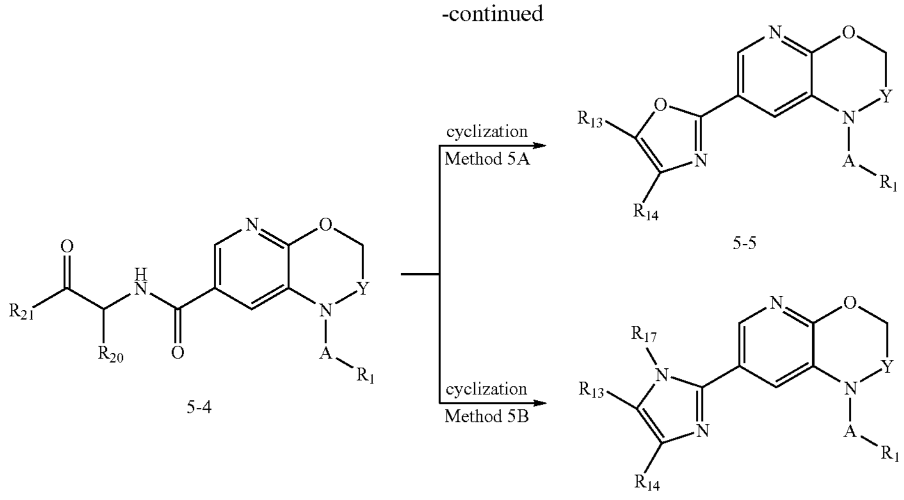

5-4

5-5

5-6

Scheme 6 (below) outlines the synthesis of 5-membered and 6-membered partially saturated heterocyclic derivatives having the structure of 6-6. Intermediate 6-1 is treated with a source of ammonia to provide carboxamide 6-2. Dehydration of 6-2 is accomplished with the choice of an appropriate dehydrating agent (such as $POCl_3$, $P_2O_5$) at elevated temperatures. Direct conversion of nitrile 6-3 to compounds of the structure 6-6 can be accomplished by treatment with the appropriately substituted amino alcohol or diamine in the presence of elemental sulfur in an alcoholic solvent. Additionally, nitrile 6-3 may be stirred in an acidic alcoholic medium to generate (in situ) the corresponding imidate. The imidate is immediately treated with the appropriately substituted amino alcohol or diamine to provide compounds of the structure 6-6.

Scheme 6

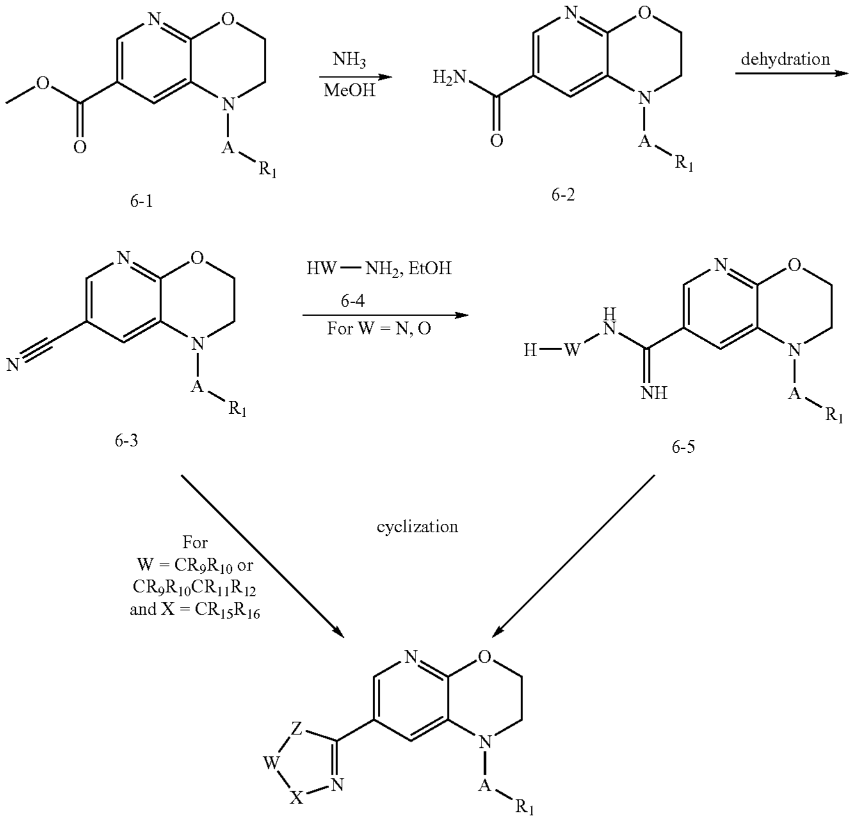

6-1

6-2

6-3

6-5

6-6

Alternatively (when W is N, or O), compounds of the structure 6-6 may be obtained through a two step process. Nitrile 6-3 is treated with intermediate 6-4 (hydrazine or hydroxylamine) in an alcoholic solvent at elevated temperatures. Intermediate 6-5 is then treated with the appropriate electrophile such as a ketone in the presence of acid (e.g. AcOH, TsOH and the like) a dialkyl carbonate, or phosgene providing compounds of the structure 6-6.

Scheme 7 (below) outlines an alternative synthesis of compounds of the formula 7-4 (i.e. compound 3-4 wherein Y=$CH_2$). The amine of intermediate 1-5 is protected (PG=protecting group, such as for instance Boc see Greene and Wuts, Protective *Groups in Organic Synthesis*—3rd ed. New York: John Wiley & Sons, Inc, 1999.) by treatment with $(Boc)_2O$ in DCM in the presence of a tertiary amine base and DMAP.

ethane at elevated temperatures (such as, for instance, at 70° C.). Amide formation is accomplished by treatment of intermediate 7-2 with amine 2-3 ($HNR_7R_8$) in DCM in the presence of an aqueous bicarbonate solution or alternatively a tertiary amine base. The protected nitrogen is then liberated under suitable conditions (For PG=Boc deprotection occurs upon treatment with a strong acid such as TFA or HCl), which provides intermediate 7-3. Intermediate 7-3 is then coupled with intermediate 1-6 (A=$SO_2$, CO) in the presence of a tertiary amine base and/or DMAP in a solvent such as DCM to provide compounds of the formula 7-4.

Subsets of compounds of the structure 3-4 are depicted by compounds 8-1 and 8-3. These compounds, containing an ester moiety, can be hydrolyzed as illustrated in Scheme 8 (below). Hydrolysis of esters 8-1 and 8-3 under basic conditions (such as LiOH in a THF/MeOH/water mixture) provides acids 8-2 and 8-4 respectively.

Scheme 7

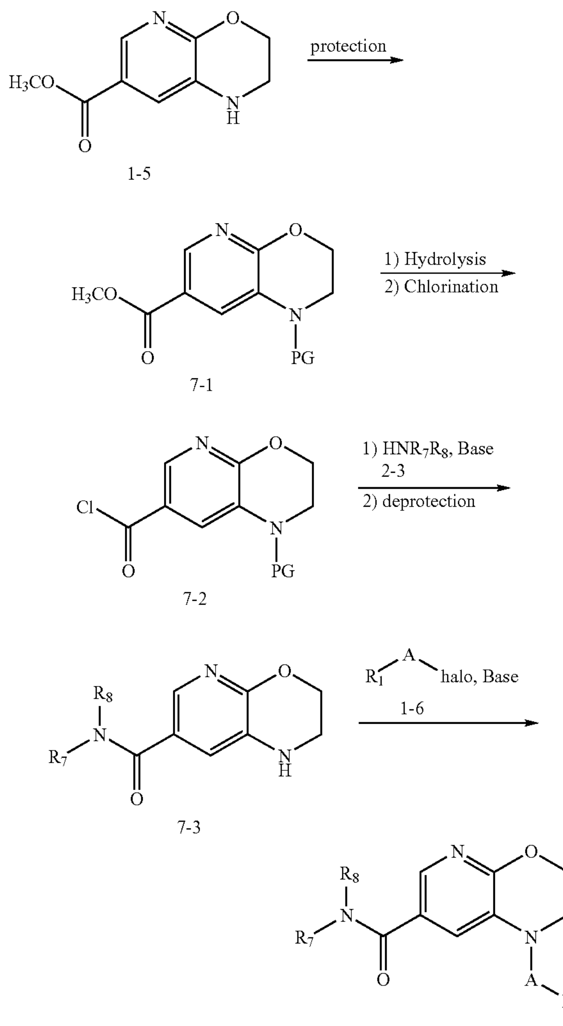

1-5
7-1
7-2
7-3
7-4

Scheme 8

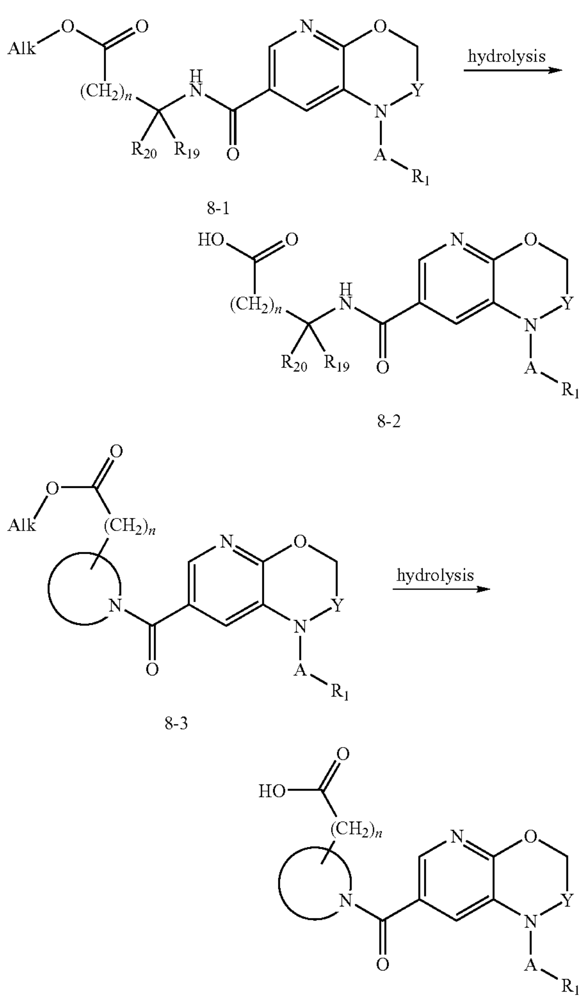

8-1
8-2
8-3
8-4

The acid chloride 7-2 is synthesized as previously described; hydrolysis of the ester under basic conditions (e.g. LiOH in a THF/MeOH/Water mixture) followed by treatment of the resulting acid with a chlorinating reagent, such as $SOCl_2$ in an aprotic solvent, such as toluene or 1,2-dichloro- Similarly, Scheme 9 describes conditions for the reduction of intermediates 8-1 and 8-3. Reduction of the esters 8-1 and 8-3 is achieved using metal hydride reagent (such as DIBAL-H or $LiAlH_4$, etc) in an ethereal solvent (such as THF or $Et_2O$) providing compounds 9-1 and 9-2 respectively.

Scheme 9

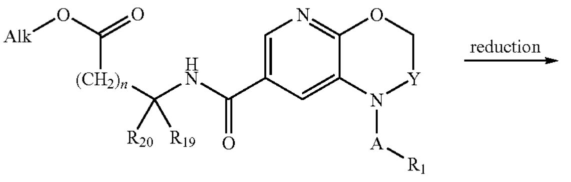

8-1

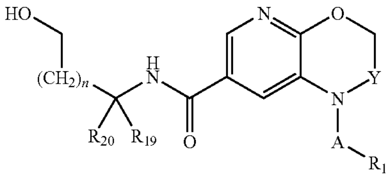

9-1

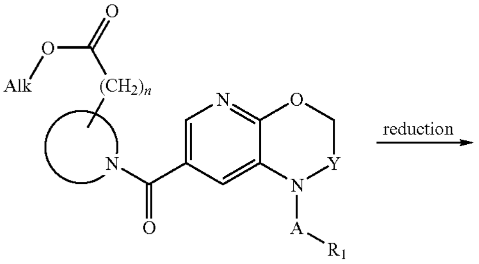

8-3

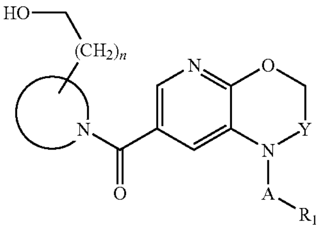

9-2

Scheme 10

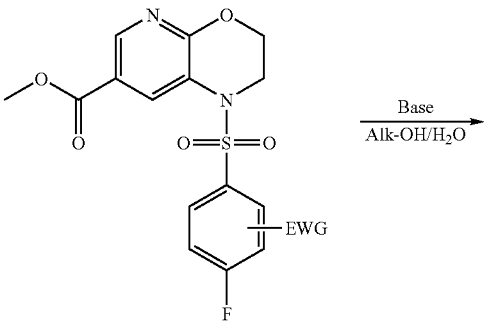

10-1

-continued

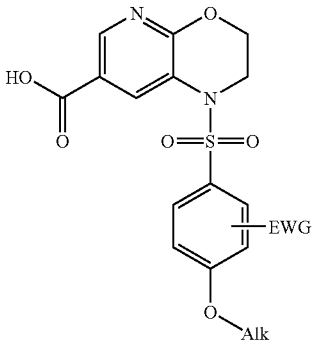

10-2

Scheme 10 outlines an alternative synthesis for a subset of compounds of the formula 1-7. Compounds such as intermediate 10-1 that contain a 4-fluoro substituted aryl sulfonamide and an electron withdrawing group (EWG) are susceptible to nucleophilic aromatic substitution. Hydrolysis under basic conditions (such as LiOH in a THF/alcohol/water mixture) provides acid 10-2 in which the fluorine is exchanged with the alcohol.

Scheme 11

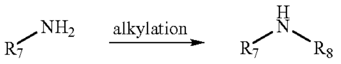

11-1 2-3

Scheme 11 discloses the synthesis of compounds of the structure 2-3. Alkylation of the primary amine 11-1 occurs by treatment of the amine with an alkyl halide in the presence of a base (such as, for instance, an inorganic carbonate, metal hydroxide or a metal hydride) in a solvent such as DMF. Alternatively alkylation of 11-1 can occur by treatment with an aldehyde in the presence of sodium triacetoxy borohydride in a solvent such as THF.

EXAMPLES

Intermediate A: Preparation of methyl 2-oxo-2,3-dihydro-1H-pyrido[2,3-b][1,4]oxazine-7-carboxylate

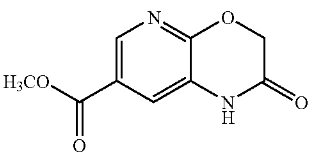

Step 1: Preparation of methyl 6-(2-ethoxy-2-oxoethoxy)-5-nitronicotinate

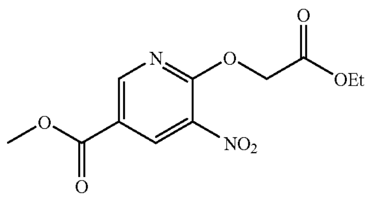

To a solution of methyl 6-chloro-5-nitronicotinate (3 g, 13.85 mmol) in THF (60 mL) and DMF (30.0 mL) was added ethyl 2-hydroxyacetate (1.573 mL, 16.62 mmol) and potassium carbonate (5.74 g, 41.6 mmol). The reaction was stirred at room temperature for 24 hours. TLC analysis of the reaction mixture indicated partial consumption of starting material. Ethyl 2-hydroxyacetate (1 mL, 10.57 mmol) and potassium carbonate (2 g, 14.5 mmol) were added and the reaction was stirred at room temperature for 72 hours. TLC analysis of the reaction mixture indicated nearly complete consumption of starting material. The reaction mixture was partially concentrated under reduced pressure for removal of THF. The resulting red solution was diluted with $H_2O$ (200 mL) and 1N HCl was added to adjust the pH to 7. The aqueous layer was extracted with EtOAc (3×200 mL). The combined organics were dried over anhydrous $Na_2SO_4$ and concentrated in vacuo. The resulting solid was purified by flash column chromatography using a gradient elution of hexanes with 10-70% EtOAc to provide methyl 6-(2-ethoxy-2-oxoethoxy)-5-nitronicotinate (2.43 g, 8.55 mmol, 61.7% yield) as a white solid.

$^1$H-NMR ($CDCl_3$) δ 8.95 (d, 1H), 8.88 (d, 1H), 5.12 (s, 2H), 4.23 (q, 2H), 3.97 (s, 3H), 1.27 (t, 3H).

Step 2: Preparation of methyl 2-oxo-2,3-dihydro-1H-pyrido[2,3-b][1,4]oxazine-7-carboxylate To a solution of methyl 6-(2-ethoxy-2-oxoethoxy)-5-nitronicotinate (2.43 g, 8.55 mmol) in AcOH (50 mL) was added iron powder (1.910 g, 34.2 mmol). The reaction was heated to 70° C. and stirred at that temperature for 2 hours. The reaction was concentrated in vacuo and diluted with water (300 mL). The solution was adjusted to pH=6 by addition of solid $K_3PO_4$. The aqueous layer was extracted with EtOAc (8×200 mL) and the combined organics were dried over anhydrous $Na_2SO_4$ and concentrated in vacuo. Methyl 2-oxo-2,3-dihydro-1H-pyrido[2,3-b][1,4]oxazine-7-carboxylate (1.24 g, 5.96 mmol, 69.7% yield) was isolated as an off-white solid and used without purification. LCMS (+ESI) m/z=209.0 $[M+H]^+$; $^1$H-NMR (DMSO-d6) δ 11.0 (s, 1H), 8.35 (d, 1H), 7.67 (d, 1H), 4.90 (s, 2H), 3.85 (s, 3H).

Intermediate B: Preparation of methyl 2,3-dihydro-1H-pyrido[2,3-b][1,4]oxazine-7-carboxylate

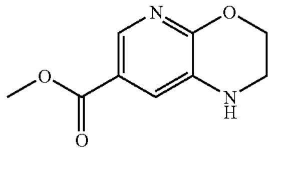

To a suspension of methyl 2-oxo-2,3-dihydro-1H-pyrido[2,3-b][1,4]oxazine-7-carboxylate (1.24 g, 5.96 mmol) in THF (30 mL) at 0° C. was added borane-tetrahydro-furan complex (23.83 mL, 23.83 mmol). The reaction was warmed to room temperature and allowed to stir for 2 hours. LCMS analysis of the reaction mixture indicated consumption of starting material. The reaction was chilled to 0° C. and quenched slowly with MeOH (20 mL). The reaction mixture was concentrated in vacuo and the treated with 5% sulfuric acid in MeOH (50 mL). The solution was heated to reflux for 1 hour. The solvent was removed under reduced pressure and the resulting oil was dissolved in EtOAc (100 mL) and washed successively with saturated aqueous $NaHCO_3$ (2×50 mL) and brine (50 mL). The combined organics were dried over anhydrous $Na_2SO_4$ and concentrated in vacuo to provide methyl 2,3-dihydro-1H-pyrido[2,3-b][1,4]oxazine-7-carboxylate (1 g, 5.15 mmol, 86% yield) as a white solid. The product was used without purification. LCMS (+ESI) m/z=195.0 $[M+H]^+$.

Intermediate C: Preparation of 1-(phenylsulfonyl)-2,3-dihydro-1H-pyrido[2,3-b][1,4]oxazine-7-carboxylic acid

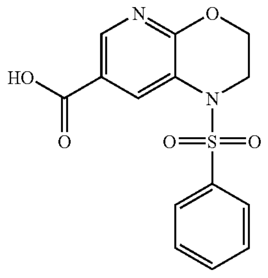

Step 1: Preparation of methyl 1-(phenylsulfonyl)-2,3-dihydro-1H-pyrido[2,3-b][1,4]oxazine-7-carboxylate To a solution of methyl 2,3-dihydro-1H-pyrido[2,3-b][1,4]oxazine-7-carboxylate (278.9 mg, 1.436 mmol) in DCM (20 mL) was added benzenesulfonyl chloride (278 μL, 2.156 mmol), DIPEA (753 μL, 4.31 mmol) and DMAP (88 mg, 0.719 mmol). The reaction was stirred at room temperature for 16 hours. LCMS analysis indicated a predominance of product in the reaction mixture. The solvent was removed under reduced pressure and the resulting oil was purified by flash column chromatography using a gradient elution of hexanes with 25-70% EtOAc to provide methyl 1-(phenylsulfonyl)-2,3-dihydro-1H-pyrido[2,3-b][1,4]oxazine-7-carboxylate (280 mg, 0.837 mmol, 58.3% yield) as a yellow glass. LCMS (+ESI) m/z=334.8 $[M+H]^+$.

Step 2: Preparation of 1-(phenylsulfonyl)-2,3-dihydro-1H-pyrido[2,3-b][1,4]oxazine-7-carboxylic acid To a solution of methyl 1-(phenylsulfonyl)-2,3-dihydro-1H-pyrido[2,3-b][1,4]oxazine-7-carboxylate (270 mg, 0.808 mmol) in THF (10 mL)/MeOH (10 mL)/water (10 mL) was added lithium hydroxide (38.7 mg, 1.615 mmol). The reaction was stirred at room temperature for 16 hours. LCMS analysis of the reaction mixture identified the molecular ion corresponding to product. The reaction mixture was concentrated in vacuo to remove the organic solvents. The aqueous layer was acidified with 1N aqueous HCl (10 mL), which resulted in a white precipitate formation. The aqueous layer was extracted with EtOAc (2×30 mL). The combined organics were dried over anhydrous $Na_2SO_4$ and concentrated in vacuo to provide 1-(phenylsulfonyl)-2,3-dihydro-1H-pyrido[2,3-b][1,4]oxazine-7-carboxylic acid (230 mg, 0.718 mmol, 89% yield) as an off-white solid that was used without further purification. LCMS (+ESI) m/z=321.0 $[M+H]^+$.

The compounds listed in Table 1 were prepared using the procedure described for the synthesis of Intermediate C. These compounds were prepared by treating intermediate B under the above-described conditions, with the appropriate substituted or unsubstituted sulfonyl chloride as detailed above. For example, Intermediate D, E, and F were prepared by substituting 4-fluorophenylsulfonyl chloride, 3-pyridylsulfonyl chloride, and 4-chlorosulfonyl chloride respectively in place of benzenesulfonyl chloride in step 1 of the preparation of Intermediate C.

TABLE 1

| Intermediate | Compound | Name | LCMS |
|---|---|---|---|
| D | 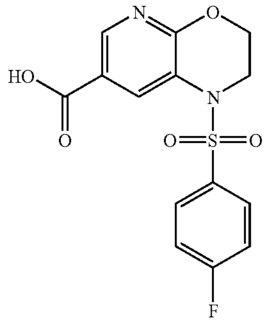 | 1-(4-fluorophenylsulfonyl)-2,3-dihydro-1H-pyrido[2,3-b][1,4]oxazine-7-carboxylic acid | $[M + H]^+ = 339.0$ |
| E | 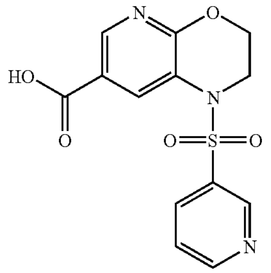 | 1-(pyridin-3-ylsulfonyl)-2,3-dihydro-1H-pyrido[2,3-b][1,4]oxazine-7-carboxylic acid | $[M + H]^+ = 322.0$ |
| F | 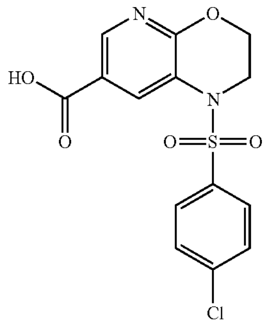 | 1-(4-chlorophenylsulfonyl)-2,3-dihydro-1H-pyrido[2,3-b][1,4]oxazine-7-carboxylic acid | $[M + H]^+ = 354.9$ |
| G | 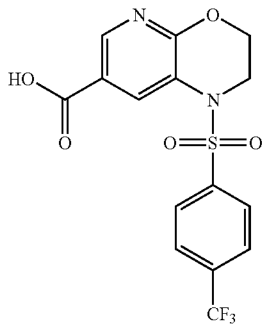 | 1-(4-(trifluoromethyl)phenylsulfonyl)-2,3-dihydro-1H-pyrido[2,3-b][1,4]oxazine-7-carboxylic acid | $[M + H]^+ = 389.0$ |

TABLE 1-continued

| Intermediate | Compound | Name | LCMS |
|---|---|---|---|
| H | 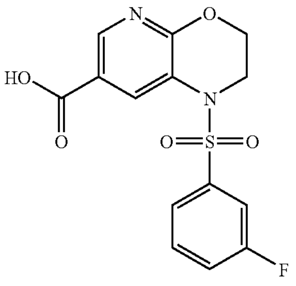 | 1-(3-fluorophenylsulfonyl)-2,3-dihydro-1H-pyrido[2,3-b][1,4]oxazine-7-carboxylic acid | $[M + H]^+ = 339.0$ |
| I | 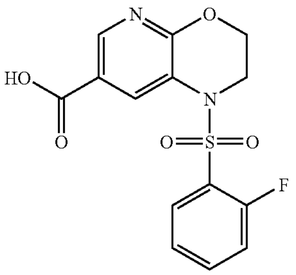 | 1-(2-fluorophenylsulfonyl)-2,3-dihydro-1H-pyrido[2,3-b][1,4]oxazine-7-carboxylic acid | $[M + H]^+ = 339.0$ |
| J | 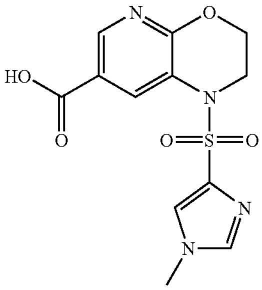 | 1-(1-methyl-1H-imidazol-4-ylsulfonyl)-2,3-dihydro-1H-pyrido[2,3-b][1,4]oxazine-7-carboxylic acid | $[M + H]^+ = 325.0$ |
| K | 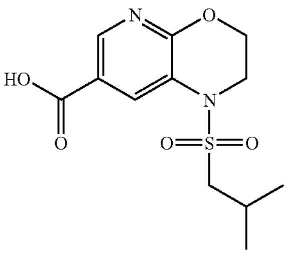 | 1-(isobutylsulfonyl)-2,3-dihydro-1H-pyrido[2,3-b][1,4]oxazine-7-carboxylic acid | $[M + H]^+ = 301.0$ |
| L | 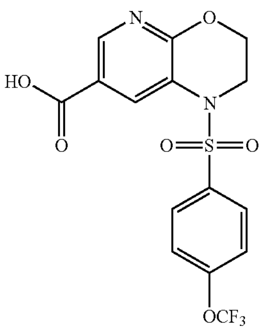 | 1-(4-(trifluoromethoxy)phenylsulfonyl)-2,3-dihydro-1H-pyrido[2,3-b][1,4]oxazine-7-carboxylic acid | $[M + H]^+ = 405.1$ |

TABLE 1-continued

| Intermediate | Compound | Name | LCMS |
| --- | --- | --- | --- |
| M | 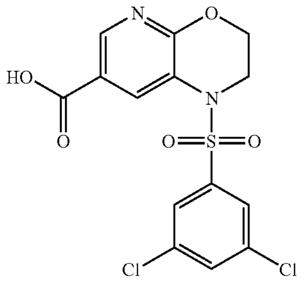 | 1-(3,5-dichlorophenyl-sulfonyl)-2,3-dihydro-1H-pyrido[2,3-b][1,4]oxazine-7-carboxylic acid | $[M + H]^+ = 389.0$ |
| N | 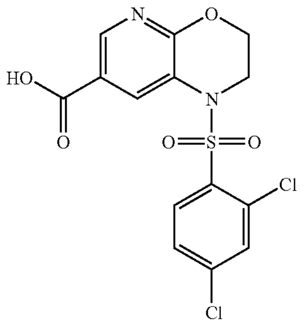 | 1-(2,4-dichlorophenyl-sulfonyl)-2,3-dihydro-1H-pyrido[2,3-b][1,4]oxazine-7-carboxylic acid | $[M + H]^+ = 389.0$ |
| O | 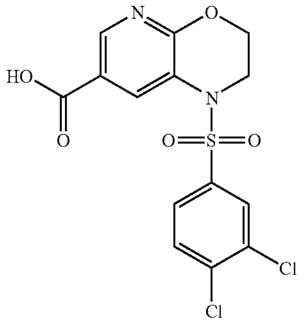 | 1-(3,4-dichlorophenyl-sulfonyl)-2,3-dihydro-1H-pyrido[2,3-b][1,4]oxazine-7-carboxylic acid | $[M + H]^+ = 389.0$ |
| P | 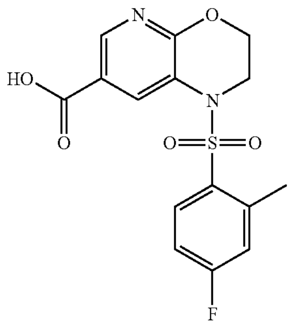 | 1-(4-fluoro-2-methylphenyl-sulfonyl)-2,3-dihydro-1H-pyrido[2,3-b][1,4]oxazine-7-carboxylic acid | $[M + H]^+ = 353.1$ |
| Q | 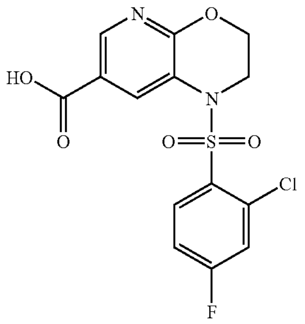 | 1-(2-chloro-4-fluorophenyl-sulfonyl)-2,3-dihydro-1H-pyrido[2,3-b][1,4]oxazine-7-carboxylic acid | $[M + H]^+ = 373.0$ |

TABLE 1-continued

| Intermediate | Compound | Name | LCMS |
| --- | --- | --- | --- |
| R | 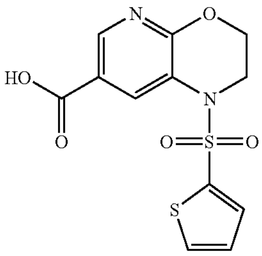 | 1-(thiophen-2-ylsulfonyl)-2,3-dihydro-1H-pyrido[2,3-b][1,4]oxazine-7-carboxylic acid | $[M + H]^+ = 327.0$ |
| S | 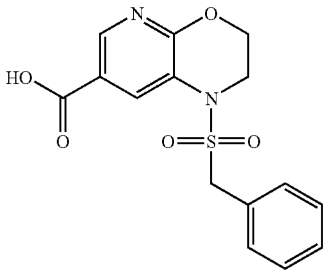 | 1-(benzylsulfonyl)-2,3-dihydro-1H-pyrido[2,3-b][1,4]oxazine-7-carboxylic acid | $[M + H]^+ = 335.1$ |
| T | 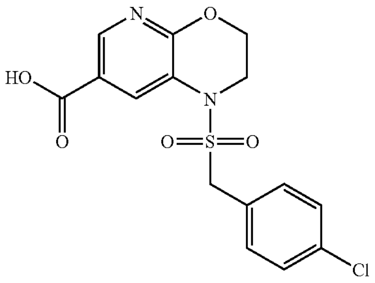 | 1-(4-chlorobenzylsulfonyl)-2,3-dihydro-1H-pyrido[2,3-b][1,4]oxazine-7-carboxylic acid | $[M + H]^+ = 369.0$ |
| U | 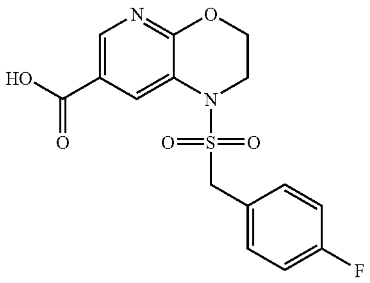 | 1-(4-fluorobenzylsulfonyl)-2,3-dihydro-1H-pyrido[2,3-b][1,4]oxazine-7-carboxylic acid | $[M + H]^+ = 353.1$ |
| V | 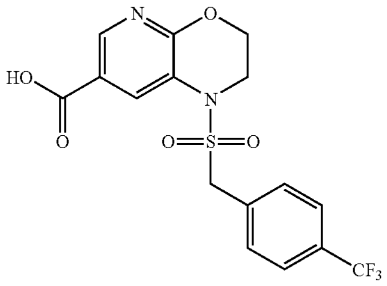 | 1-(4-(trifluoromethyl)-benzylsulfonyl)-2,3-dihydro-1H-pyrido[2,3-b][1,4]-oxazine-7-carboxylic acid | $[M + H]^+ = 403.1$ |

TABLE 1-continued

| Intermediate | Compound | Name | LCMS |
| --- | --- | --- | --- |
| W | 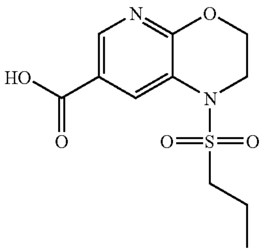 | 1-(propylsulfonyl)-2,3-dihydro-1H-pyrido[2,3-b][1,4]oxazine-7-carboxylic acid | $[M + H]^+ = 287.1$ |
| X | 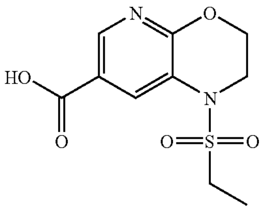 | 1-(ethylsulfonyl)-2,3-dihydro-1H-pyrido[2,3-b][1,4]oxazine-7-carboxylic acid | $[M + H]^+ = 273.1$ |
| Y | 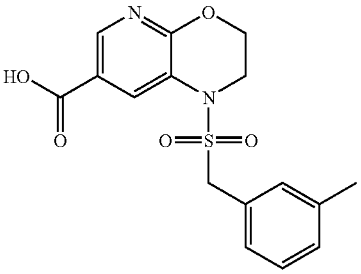 | 1-(3-methylbenzylsulfonyl)-2,3-dihydro-1H-pyrido[2,3-b][1,4]oxazine-7-carboxylic acid | $[M + H]^+ = 349.1$ |
| Z | 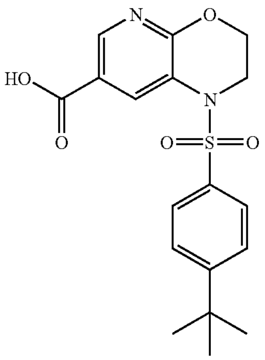 | 1-(4-tert-butylphenyl-sulfonyl)-2,3-dihydro-1H-pyrido[2,3-b][1,4]oxazine-7-carboxylic acid | $[M + H]^+ = 377.1$ |
| AA | 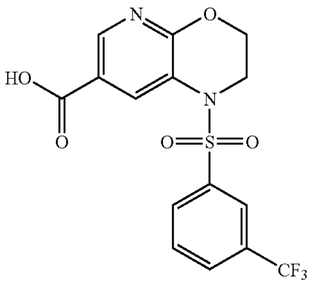 | 1-(3-(trifluoromethyl)-phenylsulfonyl)-2,3-dihydro-1H-pyrido[2,3-b][1,4]oxazine-7-carboxylic acid | $[M + H]^+ = 389.0$ |

TABLE 1-continued

| Intermediate | Compound | Name | LCMS |
|---|---|---|---|
| AB | 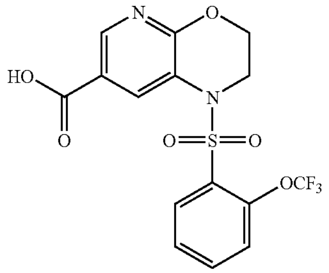 | 1-(2-(trifluoromethoxy) phenylsulfonyl)-2,3-dihydro-1H-pyrido[2,3-b][1,4]oxazine-7-carboxylic acid | $[M + H]^+ = 405.0$ |
| AC | 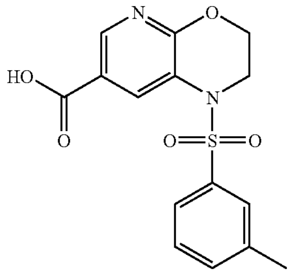 | 1-(m-tolylsulfonyl)-2,3-dihydro-1H-pyrido[2,3-b][1,4]oxazine-7-carboxylic acid | $[M + H]^+ = 335.1$ |
| AD | 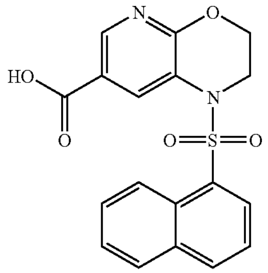 | 1-(naphthalen-1-ylsulfonyl)-2,3-dihydro-1H-pyrido[2,3-b][1,4]oxazine-7-carboxylic acid | $[M + H]^+ = 371.1$ |
| AE | 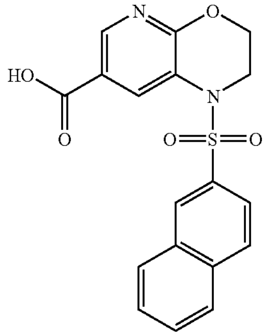 | 1-(naphthalen-2-ylsulfonyl)-2,3-dihydro-1H-pyrido[2,3-b][1,4]oxazine-7-carboxylic acid | $[M + H]^+ = 371.1$ |
| AF | 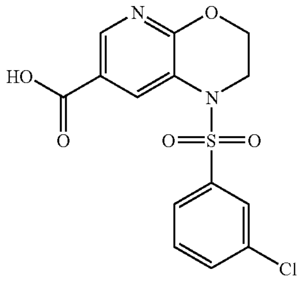 | 1-(3-chlorophenylsulfonyl)-2,3-dihydro-1H-pyrido[2,3-b][1,4]oxazine-7-carboxylic acid | $[M + H]^+ = 355.0$ |

TABLE 1-continued

| Intermediate | Compound | Name | LCMS |
| --- | --- | --- | --- |
| AG | 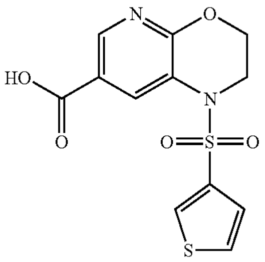 | 1-(thiophen-3-ylsulfonyl)-2,3-dihydro-1H-pyrido[2,3-b][1,4]oxazine-7-carboxylic acid | $[M + H]^+ = 327.0$ |
| AH | 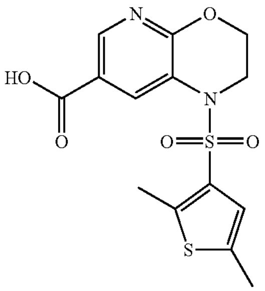 | 1-(2,5-dimethylthiophen-3-ylsulfonyl)-2,3-dihydro-1H-pyrido[2,3-b][1,4]oxazine-7-carboxylic acid | $[M + H]^+ = 355.0$ |
| AI | 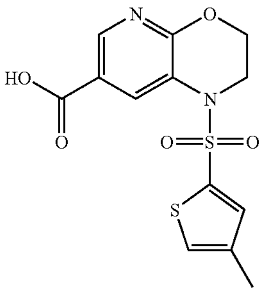 | 1-(4-methylthiophen-2-ylsulfonyl)-2,3-dihydro-1H-pyrido[2,3-b][1,4]oxazine-7-carboxylic acid | $[M + H]^+ = 341.0$ |
| AJ | 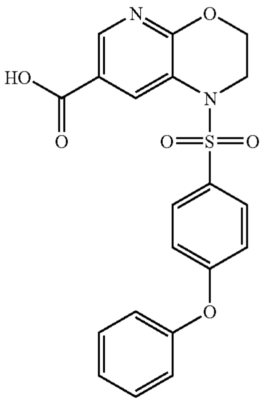 | 1-(4-phenoxyphenyl-sulfonyl)-2,3-dihydro-1H-pyrido[2,3-b][1,4]oxazine-7-carboxylic acid | $[M + H]^+ = 413.1$ |
| AK | 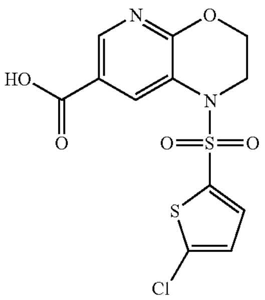 | 1-(5-chlorothiophen-2-ylsulfonyl)-2,3-dihydro-1H-pyrido[2,3-b][1,4]oxazine-7-carboxylic acid | $[M + H]^+ = 361.0$ |

TABLE 1-continued

| Intermediate | Compound | Name | LCMS |
|---|---|---|---|
| AL | 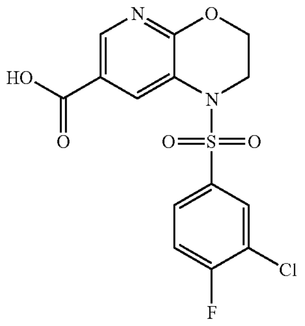 | 1-(3-chloro-4-fluorophenylsulfonyl)-2,3-dihydro-1H-pyrido[2,3-b][1,4]oxazine-7-carboxylic acid | $[M + H]^+ = 373.0$ |
| AM | 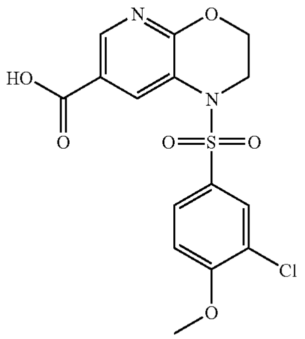 | 1-(3-chloro-4-methoxyphenylsulfonyl)-2,3-dihydro-1H-pyrido[2,3-b][1,4]oxazine-7-carboxylic acid | $[M + H]^+ = 385.0$ |
| AN | 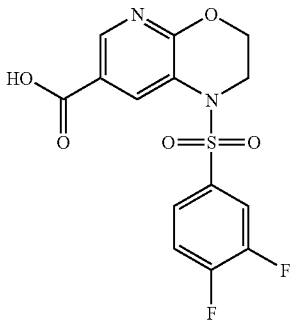 | 1-(3,4-difluorophenylsulfonyl)-2,3-dihydro-1H-pyrido[2,3-b][1,4]oxazine-7-carboxylic acid | $[M + H]^+ = 357.0$ |
| AO | 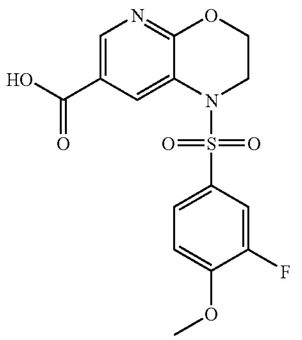 | 1-(3-fluoro-4-methoxyphenylsulfonyl)-2,3-dihydro-1H-pyrido[2,3-b][1,4]oxazine-7-carboxylic acid | $[M + H]^+ = 369.1$ |

TABLE 1-continued

| Intermediate | Compound | Name | LCMS |
| --- | --- | --- | --- |
| AP | 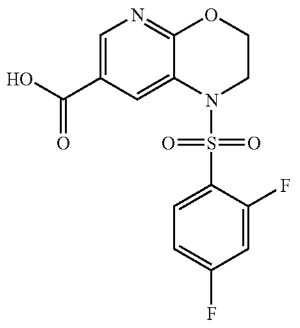 | 1-(2,4-difluorophenylsulfonyl)-2,3-dihydro-1H-pyrido[2,3-b][1,4]oxazine-7-carboxylic acid | $[M + H]^+ = 357.0$ |
| AQ | 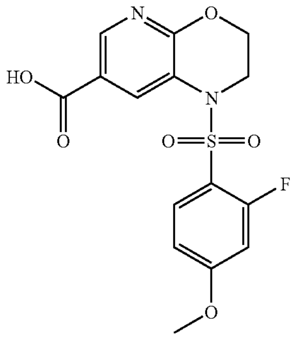 | 1-(2-fluoro-4-methoxyphenylsulfonyl)-2,3-dihydro-1H-pyrido[2,3-b][1,4]oxazine-7-carboxylic acid | $[M + H]^+ = 369.1$ |
| AR | 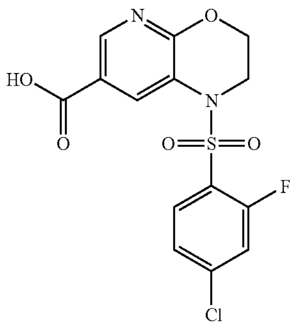 | 1-(4-chloro-2-fluorophenylsulfonyl)-2,3-dihydro-1H-pyrido[2,3-b][1,4]oxazine-7-carboxylic acid | $[M + H]^+ = 373.0$ |

Intermediate AS: Preparation of 1-benzyl-2-oxo-2,3-dihydro-1H-pyrido[2,3-b][1,4]oxazine-7-carboxylic acid

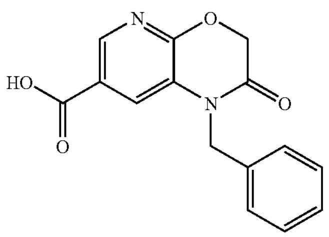

Step 1: Preparation of methyl 1-benzyl-2-oxo-2,3-dihydro-1H-pyrido[2,3-b][1,4]oxazine-7-carboxylate

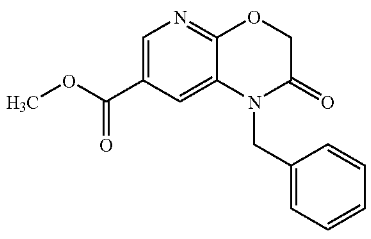

Methyl 2 oxo-2,3-dihydro-1H-pyrido[2,3-b][1,4]oxazine-7-carboxylate (50 mg, 240 μmol) was dissolved in DMF (0.5 mL) in a 2 mL microwave vial containing a magnetic stirrer bar. Potassium carbonate (100 mg, 720 μmol) was added to the vial followed by benzyl bromide (62 mg, 360 μmol) and tetrabutylammonium iodide (10 mg, 27 μmol). The vial was capped and was heated to 100° C. by microwave irradiation for 5 minutes. The reaction mixture was diluted with EtOAc (3 mL) and of saturated aqueous sodium bicarbonate (3 mL). The organic layer was removed and the aqueous layer was extracted with 2 mL of EtOAc. The organic layers were combined, dried over anhydrous $Na_2SO_4$ filtered and evaporated. This yielded 70 mg of a yellow oil which was used without further purification. LCMS (+ESI) m/z=299.1 $[M+H]^+$.

Step 2: Preparation of 1-benzyl-2-oxo-2,3-dihydro-1H-pyrido[2,3-b][1,4]oxazine-7-carboxylic acid

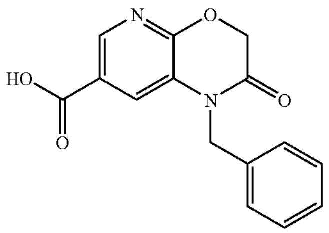

The product from Step 1 was dissolved in MeOH (1 mL) and water (0.5 mL) and placed in a 2 mL microwave vial with a magnetic stirrer bar. Lithium hydroxide (40 mg, 0.96 mmol) was added to the vial. The vial was capped and vortexed to dissolve the LiOH, and the reaction was heated for 5 minutes at 100° C. under microwave irradiation. The reaction was quenched by the addition of aqueous 1M HCl (960 μL). The volatiles were evaporated to dryness. This yielded a white/yellow solid which was used without further purification. LCMS (+ESI) m/z=285.0 $[M+H]^+$.

The compounds listed in Table 2 were prepared using the procedure described in the synthesis of Intermediate AS.

TABLE 2

| Intermediate | Compound | Name | MS |
|---|---|---|---|
| AT | 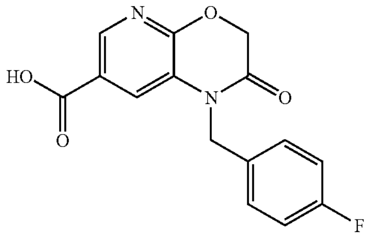 | 1-(4-fluorobenzyl)-2-oxo-2,3-dihydro-1H-pyrido[2,3-b][1,4]oxazine-7-carboxylic acid | $[M + H]^+ = 303.0$ |
| AU | 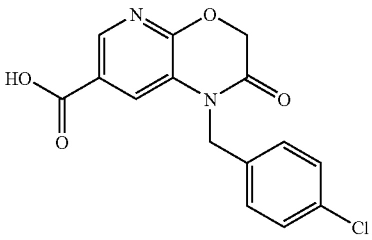 | 1-(4-methylbenzyl)-2-oxo-2,3-dihydro-1H-pyrido[2,3-b][1,4]oxazine-7-carboxylic acid | $[M + H]^+ = 319.0$ |

These compounds were prepared by treating intermediate A under the above-described conditions, using the appropriate substituted or unsubstituted halides as detailed above. For example, Intermediates AT and AU were prepared by substituting 4-fluorobenzyl bromide and 4-chlorobenzyl bromide respectively in place of benzyl bromide in Step 1 of the preparation of Intermediate AS.

Intermediate AV: Preparation of 1-(morpholinosulfonyl)-2,3-dihydro-1H-pyrido[2,3-b][1,4]oxazine-7-carboxylic acid

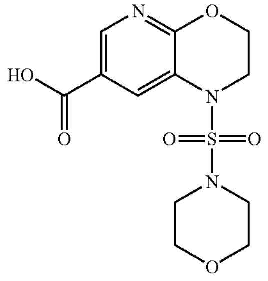

Step 1: Methyl 1-(morpholinosulfonyl)-2,3-dihydro-1H-pyrido[2,3-b][1,4]oxazine-7-carboxylate

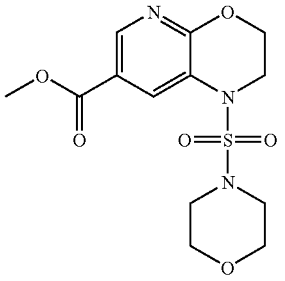

Methyl 2,3-dihydro-1H-pyrido[2,3-b][1,4]oxazine-7-carboxylate (97 mg, 0.50 mmol) was suspended in 4 mL of DCE and sequentially treated with DMAP (61 mg, 0.50 mmol) and triethylamine (0.077 mL, 0.55 mmol). Morpholine-4-sulfonyl chloride (102 mg, 0.55 mmol) was added and the mixture was stirred at ambient temperature for 2 hours and then heated to 50° C. for 2 days. The mixture was cooled to ambient temperature and diluted with 10 mL of DCM and the whole solution poured into 15 mL of 1M aqueous $H_3PO_4$. The layers were separated and the aqueous layer was extracted with 10 mL of DCM. The combined organic phases were dried over $Na_2SO_4$, filtered and concentrated in vacuo. The residue was purified by normal phase flash chromatography (gradient elution 50% to 100% EtOAc/Hexanes) to provide 88 mg (51%) of the title compound as a thick tan oil. $^1H$ NMR ($CDCl_3$) δ 8.59 (d, 1H), 8.34 (d, 1H), 4.48 (m, 2H), 3.86 (s, 3H), 3.77 (m, 2H), 3.69 (m, 4H), 3.26 (m, 4H). LCMS (+ESI) m/z=344.1 $[M+H]^+$.

Step 2: Preparation of 1-(morpholinosulfonyl)-2,3-dihydro-1H-pyrido[2,3-b][1,4]oxazine-7-carboxylic acid The product from Step 1 (80 mg, 0.23 mmol) was dissolved in 2 mL of MeOH and treated with 4M aqueous NaOH (0.29 mL, 1.16 mmol) and the mixture stirred overnight (TLC analysis showed complete consumption of starting material). The mixture was concentrated in vacuo and the residue was dissolved in 5 mL of water and 1.5 mL of 1M aqueous $H_3PO_4$ was added followed by 10 mL of EtOAc. The layers were separated and the aqueous layer extracted with an additional 10 mL portion of EtOAc. The combined organic phases were washed with brine, dried over $Na_2SO_4$, filtered and concentrated in vacuo to give the 76 mg (99%) of the title compound as a white, foamy solid. $^1H$ NMR (DMSO $d_6$) δ 13.23 (bs, 1H), 8.46 (d, 1H), 8.28 (d, 1H), 4.48 (m, 2H), 3.83 (m, 2H), 3.61 (m, 4H), 3.22 (m, 4H). LCMS (+ESI) m/z=330.1 $[M+H]^+$.

Intermediate AW: Preparation of 1-(4-(trifluoromethyl)piperidin-1-ylsulfonyl)-2,3-dihydro-1H-pyrido[2,3-b][1,4]oxazine-7-carboxylic acid

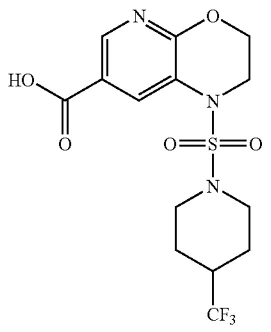

Step 1: Preparation of methyl 1-(chlorosulfonyl)-2,3-dihydro-1H-pyrido[2,3-b][1,4]oxazine-7-carboxylate

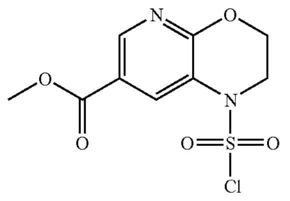

A 100 mL round-bottomed flask was charged with methyl 2,3-dihydro-1H-pyrido[2,3-b][1,4]oxazine-7-carboxylate (4 g, 20.60 mmol) and $CHCl_3$ (200 mL) was added to form a clear solution which was stirred and cooled to −78° C. To the resulting white suspension was added TEA (8.61 mL, 61.8 mmol). A solution of sulfuryl chloride (3.35 mL, 41.2 mmol) in $CHCl_3$ (10 mL) was added dropwise and the reaction mixture was maintained at −78° C. for 1 h. The solution was warmed to 0° C. at which time the mixture turned clear yellow. The reaction was stirred at 0° C. for 2 h. The reaction was quenched with $H_2O$ (200 mL) and extracted with DCM (2×200 mL). The combined organics were washed with 1 N HCl (200 mL) then dried over anhydrous $Na_2SO_4$ and concentrated in vacuo. The resulting solid was purified by flash column chromatography using a gradient elution with 0-25% acetonitrile in DCM to provide methyl 1-(chlorosulfonyl)-2,3-dihydro-1H-pyrido[2,3-b][1,4]oxazine-7-carboxylate (5.34 g, 18.24 mmol, 89% yield) as a white solid. $^1H$-NMR ($CDCl_3$) δ 8.82. (br s, 1H), 8.63 (d, 1H), 4.72 (dd, 2H), 4.10 (dd, 2H), 3.92 (s, 3H).

Step 2: Preparation of methyl 1-(4-(trifluoromethyl)piperidin-1-ylsulfonyl)-2,3-dihydro-1H-pyrido[2,3-b][1,4]oxazine-7-carboxylate

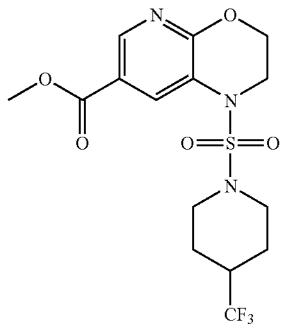

To a solution of methyl 1-(chlorosulfonyl)-2,3-dihydro-1H-pyrido[2,3-b][1,4]oxazine-7-carboxylate (250 mg, 0.854 mmol) in DCM (10 mL) at −10° C. was added TEA (0.595 mL, 4.27 mmol) and 4-(trifluoromethyl)piperidine hydrochloride (324 mg, 1.708 mmol). The reaction was allowed to stir for 3 h at −10° C. and slowly warmed to room temperature over 2 h. The reaction was allowed to stir at room temperature for 16 h. The reaction mixture was diluted with DCM (10 mL) and washed with $H_2O$ (10 mL). The organic layer was dried over anhydrous $Na_2SO_4$ and concentrated in vacuo. The resulting solid was purified by flash column chromatography using a gradient elution of DCM with 0-25% acetonitrile to provide methyl 1-(4-(trifluoromethyl)piperidin-1-ylsulfonyl)-2,3-dihydro-1H-pyrido[2,3-b][1,4]oxazine-7-carboxylate (280 mg, 0.684 mmol, 80% yield) as a white solid. LCMS (+ESI) m/z=410.1 $[M+H]^+$.

Step 3: Preparation of 1-(4-(trifluoromethyl)piperidin-1-ylsulfonyl)-2,3-dihydro-1H-pyrido[2,3-b][1,4]oxazine-7-carboxylic acid

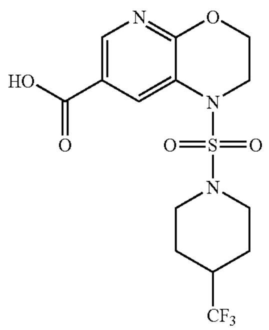

To a solution of methyl 1-(4-(trifluoromethyl)piperidin-1-ylsulfonyl)-2,3-dihydro-1H-pyrido[2,3-b][1,4]oxazine-7-carboxylate (0.280 g, 0.684 mmol) in MeOH (20 mL) was added lithium hydroxide monohydrate (0.144 g, 3.42 mmol) and water (4.00 mL) which provided a white suspension. The reaction was stirred at room temp for 2.5 h. The MeOH was removed under reduced pressure and the resulting aqueous solution was neutralized with concentrated HCl (400 mL) to provide a white solid. The suspension was extracted EtOAc (3×10 mL). The combined organics were dried over anhydrous $Na_2SO_4$ and concentrated in vacuo to provide 1-(4-(trifluoromethyl)piperidin-1-ylsulfonyl)-2,3-dihydro-1H-pyrido[2,3-b][1,4]oxazine-7-carboxylic acid as a white solid. The yield was assumed to be 100% for calculation purposes in subsequent reactions. LCMS (+ESI) m/z=396.1 $[M+H]^+$.

The compounds listed in Table 3 were prepared using the procedure described in the synthesis of Intermediate AV or AW. These compounds were prepared by treating intermediate B under the above-described conditions, using the appropriate substituted or unsubstituted sulfamoyl chloride. Alternatively, the compounds listed in Table 3 were prepared by addition of the appropriate substituted or unsubstituted amine to the compound generated in Intermediate AW step 1.

TABLE 3

| Intermediate | Compound | Name | MS |
|---|---|---|---|
| AX | 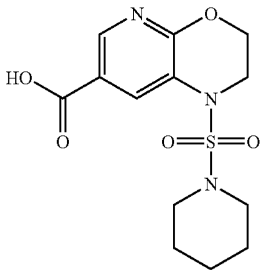 | 1-(piperidin-1-ylsulfonyl)-2,3-dihydro-1H-pyrido[2,3-b][1,4]oxazine-7-carboxylic acid | $[M + H]^+ = 328.1$ |
| AY | 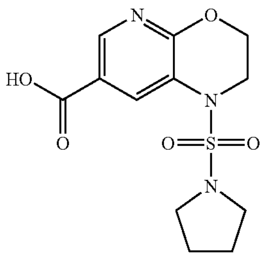 | 1-(pyrrolidin-1-ylsulfonyl)-2,3-dihydro-1H-pyrido[2,3-b][1,4]oxazine-7-carboxylic acid | $[M + H]^+ = 314.1$ |
| AZ | 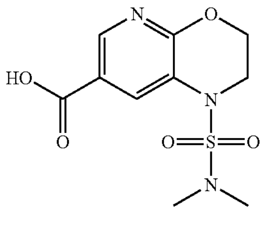 | 1-(N,N-dimethylsulfamoyl)-2,3-dihydro-1H-pyrido[2,3-b][1,4]oxazine-7-carboxylic acid | $[M + H]^+ = 288.1$ |

TABLE 3-continued

| Intermediate | Compound | Name | MS |
|---|---|---|---|
| BA | 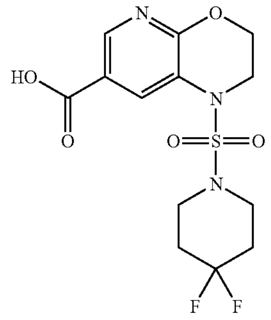 | 1-(4,4-difluoropiperidin-1-ylsulfonyl)-2,3-dihydro-1H-pyrido][2,3-b][1,4]oxazine-7-carboxylic acid | $[M + H]^+ = 364.1$ |
| BB | 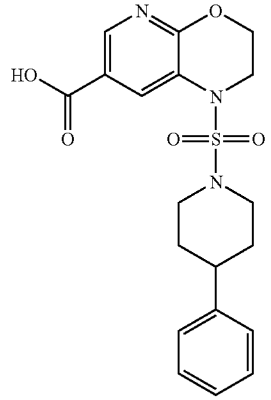 | 1-(4-phenylpiperidin-1-ylsulfonyl)-2,3-dihydro-1H-pyrido[2,3-b][1,4]oxazine-7-carboxylic acid | $[M + H]^+ = 404.1$ |
| BC | 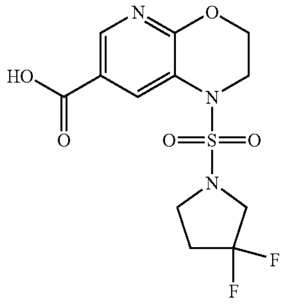 | 1-(3,3-difluoropyrrolidin-1-ylsulfonyl)-2,3-dihydro-1H-pyrido[2,3-b][1,4]oxazine-7-carboxylic acid | $[M + H]^+ = 350.1$ |
| BD | 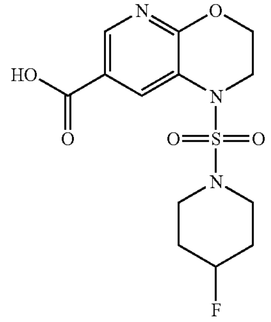 | 1-(4-fluoropiperidin-1-ylsulfonyl)-2,3-dihydro-1H-pyrido[2,3-b][1,4]oxazine-7-carboxylic acid | $[M + H]^+ = 346.1$ |

TABLE 3-continued

| Intermediate | Compound | Name | MS |
| --- | --- | --- | --- |
| BE | 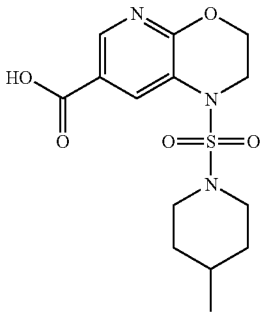 | 1-(4-methylpiperidin-1-ylsulfonyl)-2,3-dihydro-1H-pyrido[2,3-b][1,4]oxazine-7-carboxylic acid | $[M + H]^+ = 342.1$ |
| BF | 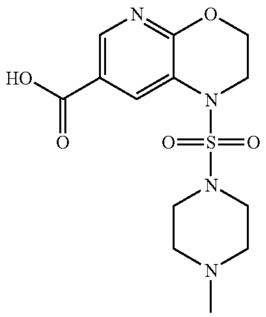 | 1-(4-methylpiperazin-1-ylsulfonyl)-2,3-dihydro-1H-pyrido[2,3-b][1,4]oxazine-7-carboxylic acid | $[M + H]^+ = 343.1$ |
| BG | 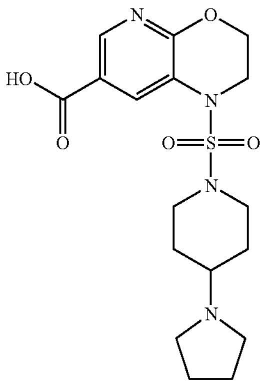 | 1-(4-(pyrrolidin-1-yl)piperidin-1-ylsulfonyl)-2,3-dihydro-1H-pyrido[2,3-b][1,4]oxazine-7-carboxylic acid | $[M + H]^+ = 397.1$ |
| BH | 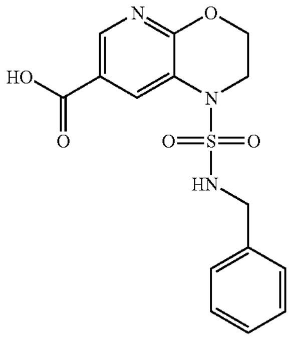 | 1-(N-benzylsulfamoyl)-2,3-dihydro-1H-pyrido[2,3-b][1,4]oxazine-7-carboxylic acid | $[M + H]^+ = 350.1$ |

TABLE 3-continued

| Intermediate | Compound | Name | MS |
|---|---|---|---|
| BI | 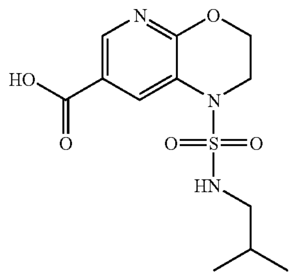 | 1-(N-isobutylsulfamoyl)-2,3-dihydro-1H-pyrido[2,3-b][1,4]oxazine-7-carboxylic acid | $[M + H]^+ = 316.1$ |
| BJ | 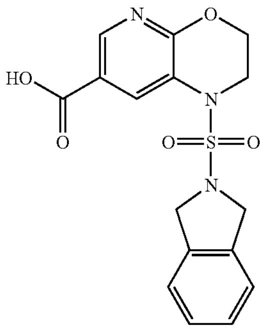 | 1-(isoindolin-2-ylsulfonyl)-2,3-dihydro-1H-pyrido[2,3-b][1,4]oxazine-7-carboxylic acid | $[M + H]^+ = 362.1$ |

Example 1

Preparation of (1-(phenylsulfonyl)-2,3-dihydro-1H-pyrido[2,3-b][1,4]oxazin-7-yl)(piperidin-1-yl)methanone

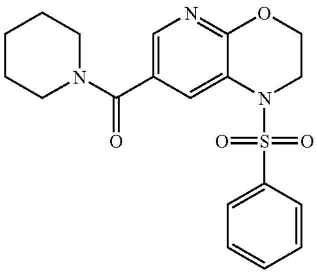

Step 1: Preparation of 1-(phenylsulfonyl)-2,3-dihydro-1H-pyrido[2,3-b][1,4]oxazine-7-carbonyl chloride

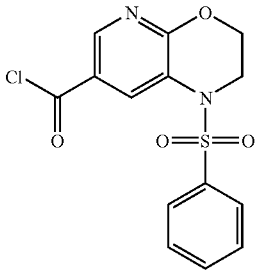

To a solution of 1-(phenylsulfonyl)-2,3-dihydro-1H-pyrido[2,3-b][1,4]oxazine-7-carboxylic acid (230 mg, 0.718 mmol) in DCE (20 mL) was added thionyl chloride (0.5 mL, 6.85 mmol). The solution turned cloudy white. The reaction was heated to 70° C. and stirred at that temperature for 2 hours, after which time the solution was clear. LCMS analysis of the reaction mixture indicated consumption of starting material. The reaction mixture was concentrated in vacuo. 1-(phenylsulfonyl)-2,3-dihydro-1H-pyrido[2,3-b][1,4]oxazine-7-carbonyl chloride (243 mg, 0.718 mmol, 100% yield) was used without purification. LCMS (methanol adduct, i.e. the methyl ester; +ESI) m/z=335.0 $[M+H]^+$.

Step 2: Preparation of (1-(phenylsulfonyl)-2,3-dihydro-1H-pyrido[2,3-b][1,4]oxazin-7-yl)(piperidin-1-yl)methanone To a biphasic mixture of 1-(phenylsulfonyl)-2,3-dihydro-1H-pyrido[2,3-b][1,4]oxazine-7-carbonyl chloride (40 mg, 0.118 mmol) in DCM (1.5 mL) and saturated aqueous $NaHCO_3$ (1.5 mL) was added piperidine (25 μL, 0.253 mmol). The reaction was stirred at room temperature for 16 hours. TLC analysis of the reaction mixture indicated consumption of starting material. The biphasic mixture was extracted with DCM (1.5 mL) (3×2 mL). The combined organics were dried over anhydrous $Na_2SO_4$ and concentrated in vacuo. The resulting solid was purified by flash column chromatography using a gradient elution of hexanes with 10-90% EtOAc to provide (1-(phenylsulfonyl)-2,3-dihydro-1H-pyrido[2,3-b][1,4]oxazin-7-yl)(piperidin-1-yl) methanone (32.5 mg, 0.081 mmol, 68.9% yield) as a white solid. LCMS (+ESI) m/z=388.1 $[M+H]^+$; $^1H$-NMR ($CDCl_3$) δ 8.25. (d, 1H), 8.14 (d, 1H), 7.66 (m, 2H), 7.61 (tt, 1H), 7.49 (m, 2H), 3.93 (m, 2H), 3.85 (m, 2H), 3.69 (br s, 2H), 3.45 (br s, 2H), 1.75-1.55 (m, 6H).

Example 2

Preparation of N-tert-butyl-1-(piperidin-1-ylsulfonyl)-2,3-dihydro-1H-pyrido[2,3-b][1,4]oxazine-7-carboxamide

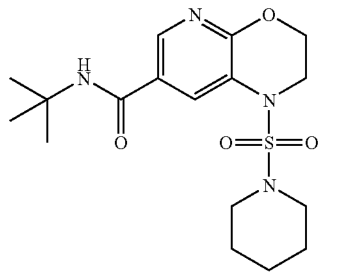

Step 1: Preparation of 1-(piperidin-1-ylsulfonyl)-2,3-dihydro-1H-pyrido[2,3-b][1,4]oxazine-7-carbonyl chloride

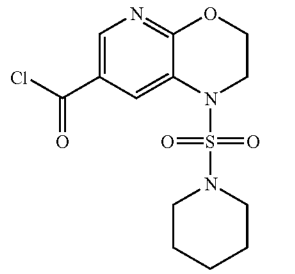

To a suspension of 1-(piperidin-1-ylsulfonyl)-2,3-dihydro-1H-pyrido[2,3-b][1,4]oxazine-7-carboxylic acid (110 mg, 0.336 mmol) in DCE (5 mL) was added oxalyl chloride (293 μL, 3.36 mmol) and DMF (5 μL, 0.065 mmol). The reaction was heated to 50° C. and stirred at that temperature for 16 h. The reaction was concentrated in vacuo and used without further purification. The reaction yield was assumed to be 100% for calculation purposes only. LCMS (methanol adduct, i.e. the methyl ester; +ESI) m/z=342.1 $[M+H]^+$.

Step 2: Preparation of N-tert-butyl-1-(piperidin-1-ylsulfonyl)-2,3-dihydro-1H-pyrido[2,3-b][1,4]oxazine-7-carboxamide To a biphasic mixture of 1-(piperidin-1-ylsulfonyl)-2,3-dihydro-1H-pyrido[2,3-b][1,4]oxazine-7-carbonyl chloride (38 mg, 0.110 mmol) in DCM (2 mL) and saturated aqueous $NaHCO_3$ (2 mL) was added tert-butylamine (50 μL, 0.472 mmol). The reaction was stirred at room temperature for 16 h. The biphasic mixture was extracted with DCM (3×2 mL). The combined organics were dried over anhydrous $Na_2SO_4$ and concentrated in vacuo. The resulting solid was purified by flash column chromatography using a gradient elution of hexanes with 10-70% EtOAc to provide N-tert-butyl-1-(piperidin-1-ylsulfonyl)-2,3-dihydro-1H-pyrido[2,3-b][1,4]oxazine-7-carboxamide (27.7 mg, 0.072 mmol, 65.2% yield over 2 steps) as a white solid. LCMS (+ESI) m/z=383.1 $[M+H]^+$; $^1$H-NMR ($CDCl_3$) δ 8.27. (d, 1H), 8.17 (d, 1H), 5.86 (br s, 1H), 4.49 (dd, 2H), 3.78 (dd, 2H), 3.29 (dd, 4H), 1.67-1.53 (m, 6H), 1.46 (s, 9H).

Example 3

Preparation of N-tert-butyl-1-(4-cyanophenylsulfonyl)-2,3-dihydro-1H-pyrido[2,3-b][1,4]oxazine-7-carboxamide

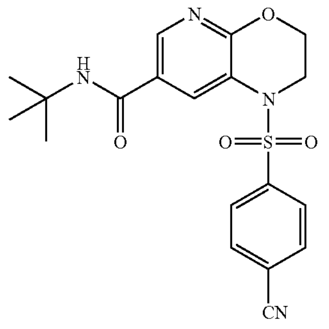

Step 1: Preparation of 1-tert-butyl 7-methyl 2,3-dihydro-1H-pyrido[2,3-b][1,4]oxazine-1,7-dicarboxylate

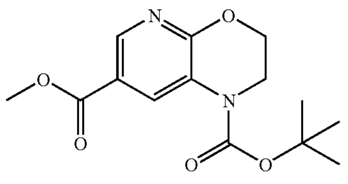

To a solution of methyl 2,3-dihydro-1H-pyrido[2,3-b][1,4]oxazine-7-carboxylate (1.52 g, 7.83 mmol), in DCM (20 mL) was added TEA (2.18 mL, 15.65 mmol), di-tert-butyl dicarbonate ($Boc_2O$) (8.54 g, 15.65 mmol) and DMAP (1.43 g, 11.74 mmol) to provide a pale yellow solution. The reaction mixture was stirred at 40° C. for 18 hours. The reaction was quenched by the addition of brine (5 mL). The phases were separated and the aqueous layer was extracted with DCM (2×5 mL). The combined organics were dried over anhydrous $Na_2SO_4$ and concentrated in vacuo. The resulting paste was purified by flash column chromatography using a gradient elution of hexanes with 0-100% EtOAc to provide 1-tert-butyl 7-methyl 2,3-dihydro-1H-pyrido[2,3-b][1,4]oxazine-1,7-dicarboxylate (1.25 g, 4.25 mmol, 54% yield). LCMS (+ESI) m/z=295.1 $[M+H]^+$.

Step 2: Preparation of 1-(tert-butoxycarbonyl)-2,3-dihydro-1H-pyrido[2,3-b][1,4]oxazine-7-carboxylic acid

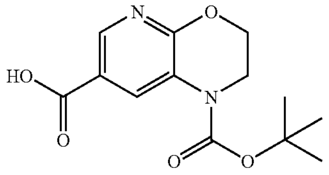

To a suspension of 1-tert-butyl 7-methyl 2,3-dihydro-1H-pyrido[2,3-b][1,4]oxazine-1,7-dicarboxylate (1.25 g, 4.25 mmol) in methanol (20 mL) and water (5 mL) was added lithium hydroxide monohydrate (1.27 g, 30.3 mmol). The reaction was warmed to 40° C. and stirred at that temperature for 18 h. The reaction mixture was concentrated in vacuo to provide 1-(tert-butoxycarbonyl)-2,3-dihydro-1H-pyrido[2,3-b][1,4]oxazine-7-carboxylic acid. The yield was assumed to be 100% for calculation purposes in subsequent reactions. LCMS (+ESI) m/z=281.1 $[M+H]^+$.

Step 3: Preparation of text-butyl 7-(text-butylcarbamoyl)-2,3-dihydro-1H-pyrido[2,3-b][1,4]oxazine-1-carboxylate

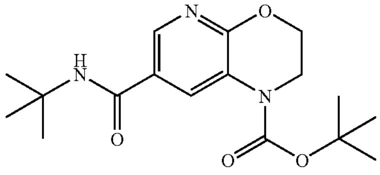

To a suspension of 1-(tert-butoxycarbonyl)-2,3-dihydro-1H-pyrido[2,3-b][1,4]oxazine-7-carboxylic acid (1.191 g, 4.25 mmol) in DMF (10 mL) was added DIPEA (2.22 mL, 12.71 mmol), TBTU (1.12 g, 3.49 mmol) and tert-butylamine (1 mL, 9.43 mmol). The reaction was subjected to microwave irradiation (150° C., 10 min). The reaction was incomplete so additional DIPEA (2.22 mL, 12.71 mmol) and tert-butylamine (1 mL, 9.43 mmol) were added. The reaction was resubjected to microwave irradiation (150° C., 15 min). Additional TBTU (1.12 g, 3.49 mmol) was added and the reaction was again subjected to microwave irradiation (150° C., 5 min). The mixture was diluted with EtOAc (50 mL), washed with water (3×20 mL) and dried over anhydrous $Na_2SO_4$. The crude mixture was used without purification. The yield was assumed to be 100% for calculation purposes in Step 4. LCMS (+ESI) m/z=336.1 $[M+H]^+$.

Step 4: Preparation of N-tert-butyl-2,3-dihydro-1H-pyrido[2,3-b][1,4]oxazine-7-carboxamide

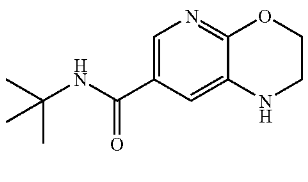

To a suspension of tert-butyl 7-(tert-butylcarbamoyl)-2,3-dihydro-1H-pyrido[2,3-b][1,4]oxazine-1-carboxylate (1.425 g, 4.25 mmol) in DCM (5 mL) and DMF (5 mL) was added TFA (3 mL, 38.9 mmol). The reaction was stirred at 40° C. for 24 h. Additional TFA (2.2 mL, 28.5 mmol) was added to consume unreacted starting material. The reaction was allowed to stir at room temperature for 2 h. A further addition of TFA (4.4 mL, 57.0 mmol) was performed and the reaction was allowed to stir for 2 h. Upon consumption of the starting material the reaction mixture was concentrated in vacuo and purified by flash column chromatography using a gradient elution of DCM and 2-8% MeOH spiked with 1% TEA. The eluant was evaporated to yield an orange oil. The oil was treated with saturated aqueous $NaHCO_3$ (100 mL) and extracted with EtOAc (2×50 mL). The combined organics were dried over $Na_2SO_4$ and concentrated in vacuo to provide N-tert-butyl-2,3-dihydro-1H-pyrido[2,3-b][1,4]oxazine-7-carboxamide (203 mg, 0.864 mmol, 20% yield 3 steps) as a white solid. LCMS (+ESI) m/z=236.1 $[M+H]^+$;

Step 5: Preparation of N-tert-butyl-1-(4-cyanophenylsulfonyl)-2,3-dihydro-1H-pyrido[2,3-b][1,4]oxazine-7-carboxamide To a suspension of N-tert-butyl-2,3-dihydro-1H-pyrido[2,3-b][1,4]oxazine-7-carboxamide (30 mg, 0.128 mmol), in DCM (2 mL) was added 4-cyanobenzene-1-sulfonyl chloride (38.6 mg, 0.191 mmol), DIPEA (0.067 mL, 0.383 mmol) and DMAP (15.58 mg, 0.128 mmol). The reaction was allowed to stir at 40° C. for 1.6 h. The reaction still contained starting material so THF (40 μL) was added and the reaction was stirred at 50° C. for 2 h. Upon consumption of starting material the reaction mixture was concentrated in vacuo. The resulting solid was purified by flash column chromatography using a gradient elution of hexanes with 20-100% EtOAc to provide N-tert-butyl-1-(4-cyanophenylsulfonyl)-2,3-dihydro-m-pyrido[2,3-b][1,4]oxazine-7-carboxamide (29.3 mg, 0.070 mmol, 55% yield) as a white solid. LCMS (+ESI) m/z=401.1 $[M+H]^+$.

The compounds listed in Table 4 were prepared using the procedures described in Example 1 or Example 2. Compounds of Examples 4 to 139 and 197 to 201 were prepared using an intermediate chosen from intermediates C to AR, and the appropriate primary or secondary amine under the conditions described in Example 1. For instance, compounds of Examples 4, 5, and 6 were prepared by substituting morpholine, tert-butyl amine and (S)-2-amino-N,3,3-trimethylbutanamide hydrochloride respectively in place of piperidine in Step 2 of Example 1. Compounds of Examples 140-196 were prepared using an intermediate chosen from intermediates AV-BJ and the appropriate primary or secondary amine under the conditions described in Example 2. For instance, compounds of Examples 141, and 142 were prepared by substituting 3-amino-2,2-dimethylpropan-1-ol and 2-methyl-2-amino butane respectively in place of t-butyl amine in Step 2 of Example 2.

TABLE 4

| Example | Compound | Name | LCMS |
|---|---|---|---|
| 4 | 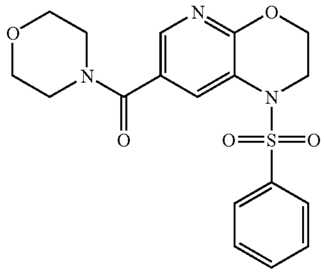 | morpholino(1-(phenyl-sulfonyl)-2,3-dihydro-1H-pyrido[2,3-b][1,4]oxazin-7-yl)methanone | $[M + H]^+ = 390.1$ |
| 5 | 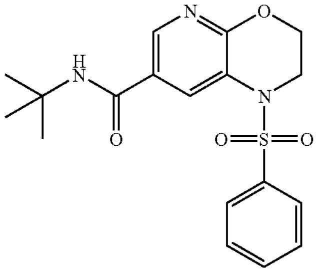 | N-tert-butyl-1-(phenyl-sulfonyl)-2,3-dihydro-1H-pyrido[2,3-b][1,4]oxazine-7-carboxamide | $[M + H]^+ = 376.1$ |
| 6 | 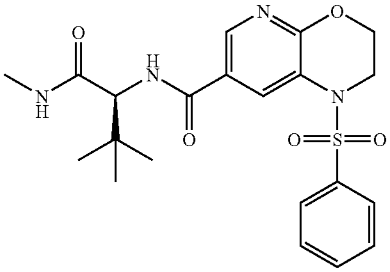 | (S)-N-(3,3-dimethyl-1-(methylamino)-1-oxobutan-2-yl)-1-(phenyl-sulfonyl)-2,3-dihydro-1H-pyrido[2,3-b][1,4]oxazine-7-carboxamide | $[M + H]^+ = 447.1$ |
| 7 | 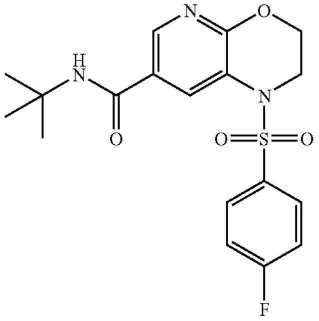 | N-tert-butyl-1-(4-fluoro-phenylsulfonyl)-2,3-dihydro-1H-pyrido[2,3-b][1,4]oxazine-7-carboxamide | $[M + H]^+ = 394.1$ |
| 8 | 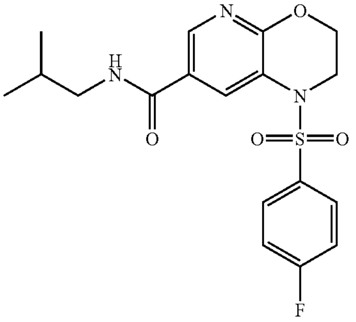 | 1-(4-fluorophenyl-sulfonyl)-N-isobutyl-2,3-dihydro-1H-pyrido[2,3-b][1,4]oxazine-7-carboxamide | $[M + H]^+ = 394.0$ |

TABLE 4-continued

| Example | Compound | Name | LCMS |
|---|---|---|---|
| 9 | 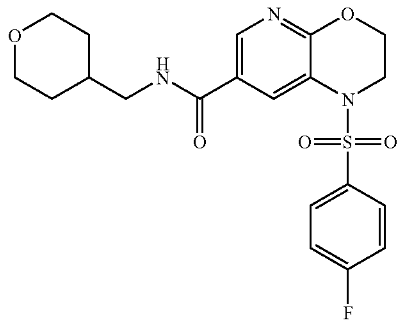 | 1-(4-fluorophenyl-sulfonyl)-N-((tetrahydro-2H-pyran-4-yl)methyl)-2,3-dihydro-1H-pyrido[2,3-b][1,4]oxazine-7-carboxamide | $[M + H]^+ = 436.0$ |
| 10 | 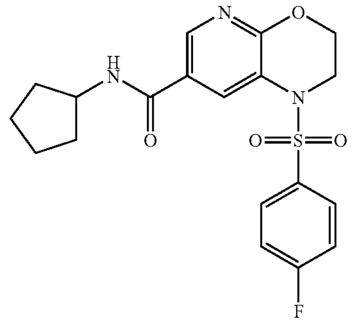 | 1-(4-fluorophenyl-sulfonyl)-N-neopentyl-2,3-dihydro-1H-pyrido[2,3-b][1,4]oxazine-7-carboxamide | $[M + H]^+ = 406.0$ |
| 11 | 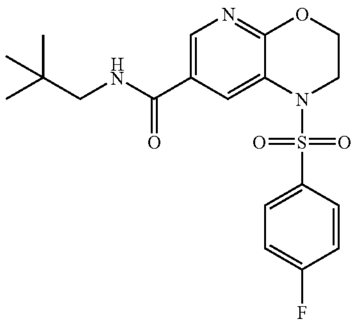 | 1-(4-fluorophenyl-sulfonyl)-N-(3-methoxypropyl)-2,3-dihydro-1H-pyrido[2,3-b][1,4]oxazine-7-carboxamide | $[M + H]^+ = 408.0$ |
| 12 | 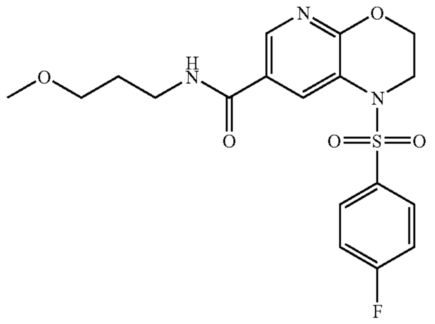 | N-cyclopentyl-1-(4-fluorophenyl-sulfonyl)-2,3-dihydro-1H-pyrido[2,3-b][1,4]oxazine-7-carboxamide | $[M + H]^+ = 410.0$ |

TABLE 4-continued

| Example | Compound | Name | LCMS |
|---|---|---|---|
| 13 | 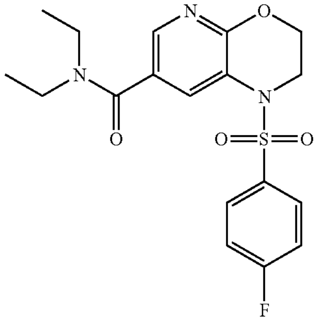 | N,N-diethyl-1-(4-fluorophenylsulfonyl)2,3-dihydro-1H-pyrido[2,3-b][1,4]oxazine-7-carboxamide | $[M + H]^+ = 394.2$ |
| 14 | 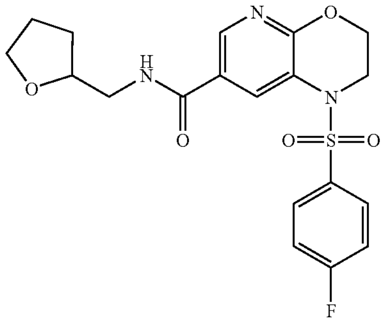 | 1-(4-fluorophenyl-sulfonyl)-N-((tetra-hydrofuran-2-yl) methyl)-2,3-dihydro-1H-pyrido [2,3-b][1,4]oxazine-7-carboxamide | $[M + H]^+ = 422.18$ |
| 15 | 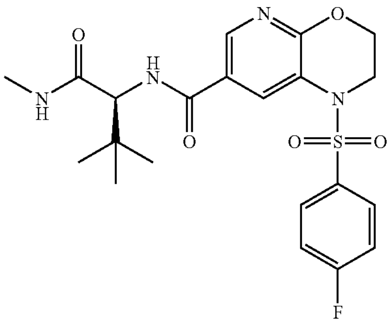 | (S)-N-(3,3-dimethyl-1-(methylamino)-1-oxobutan-2-yl)-1-(4-fluorophenyl-sulfonyl)-2,3-dihydro-1H-pyrido [2,3-b][1,4]oxazine-7-carboxamide | $[M + H]^+ = 465.1$ |
| 16 | 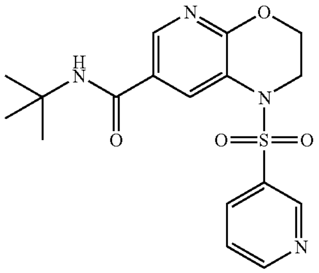 | N-tert-butyl-1-(pyridin-3-ylsulfonyl)-2,3-dihydro-1H-pyrido[2,3-b][1,4]oxazine-7-carboxamide | $[M + H]^+ = 377.2$ |
| 17 | 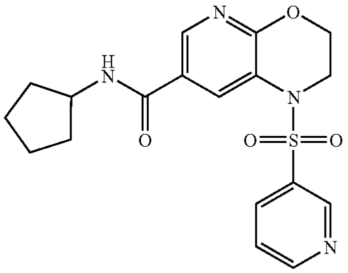 | N-cyclopentyl-1-(pyridin-3-ylsulfonyl)-2,3-dihydro-1H-pyrido[2,3-b][1,4]oxazine-7-carboxamide | $[M + H]^+ = 389.3$ |

TABLE 4-continued

| Example | Compound | Name | LCMS |
|---|---|---|---|
| 18 | 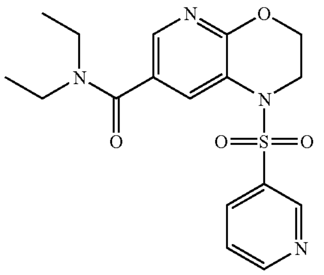 | N,N-diethyl-1-(pyridin-3-ylsulfonyl)-2,3-dihydro-1H-pyrido[2,3-b][1,4]oxazine-7-carboxamide | $[M + H]^+ = 377.2$ |
| 19 | 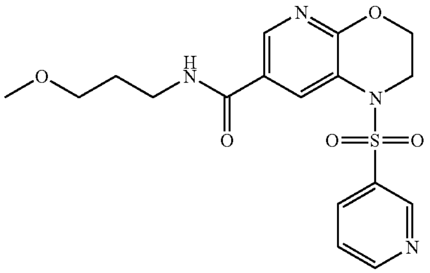 | N-(3-methoxypropyl)-1-(pyridin-3-ylsulfonyl)-2,3-dihydro-1H-pyrido[2,3-b][1,4]oxazine-7-carboxamide | $[M + H]^+ = 393.0$ |
| 20 | 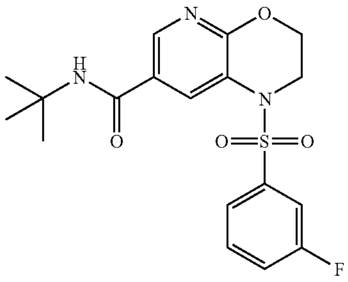 | N-tert-butyl-1-(3-fluorophenylsulfonyl)-2,3-dihydro-1H-pyrido[2,3-b][1,4]oxazine-7-carboxamide | $[M + H]^+ = 394.1$ |
| 21 | 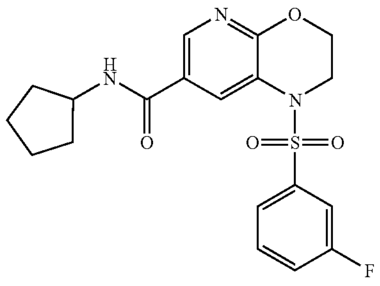 | N-cyclopentyl-1-(3-fluorophenylsulfonyl)-2,3-dihydro-1H-pyrido[2,3-b][1,4]oxazine-7-carboxamide | $[M + H]^+ = 406.1$ |
| 22 | 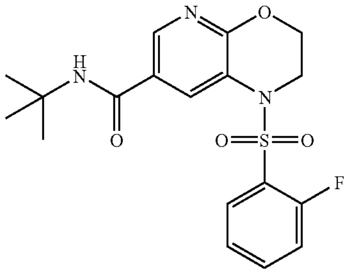 | N-tert-butyl-1-(2-fluorophenylsulfonyl)-2,3-dihydro-1H-pyrido[2,3-b][1,4]oxazine-7-carboxamide | $[M + H]^+ = 394.1$ |

TABLE 4-continued

| Example | Compound | Name | LCMS |
| --- | --- | --- | --- |
| 23 | 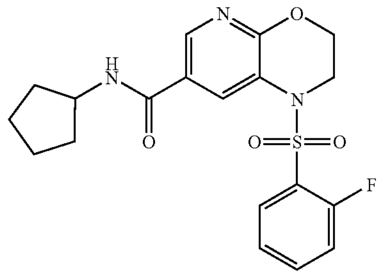 | N-cyclopentyl-1-(2-fluorophenylsulfonyl)-2,3-dihydro-1H-pyrido[2,3-b][1,4]oxazine-7-carboxamide | $[M + H]^+ = 406.1$ |
| 24 | 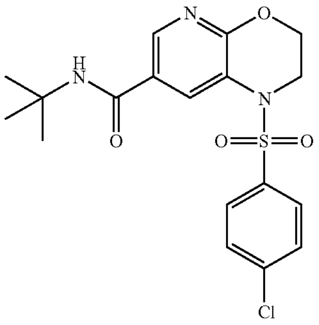 | N-tert-butyl-1-(4-chlorophenylsulfonyl)-2,3-dihydro-1H-pyrido[2,3-b][1,4]oxazine-7-carboxamide | $[M + H]^+ = 410.1$ |
| 25 | 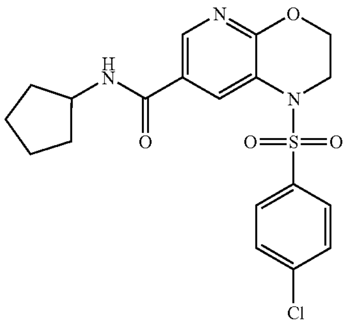 | 1-(4-chlorophenyl-sulfonyl)-N-cyclopentyl-2,3-dihydro-1H-pyrido[2,3-b][1,4]oxazine-7-carboxamide | $[M + H]^+ = 422.0$ |
| 26 | 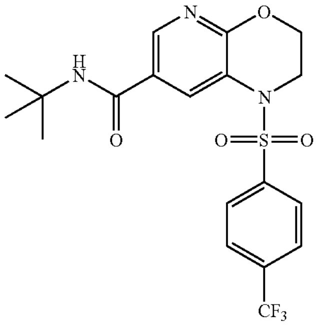 | N-tert-butyl-1-(4-(trifluoromethyl)phenylsulfonyl)-2,3-dihydro-1H-pyrido[2,3-b][1,4]oxazine-7-carboxamide | $[M + H]^+ = 444.1$ |
| 27 | 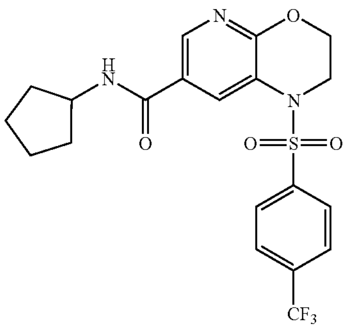 | N-cyclopentyl-1-(4-(trifluoromethyl)phenylsulfonyl)-2,3-dihydro-1H-pyrido[2,3-b][1,4]oxazine-7-carboxamide | $[M + H]^+ = 456.1$ |

TABLE 4-continued

| Example | Compound | Name | LCMS |
|---|---|---|---|
| 28 | 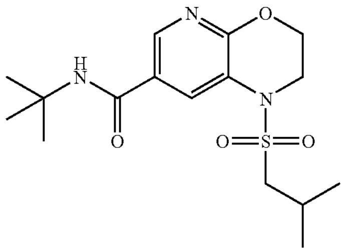 | N-tert-butyl-1-(isobutylsulfonyl)-2,3-dihydro-1H-pyrido[2,3-b][1,4]oxazine-7-carboxamide | $[M + H]^+ = 356.1$ |
| 29 | 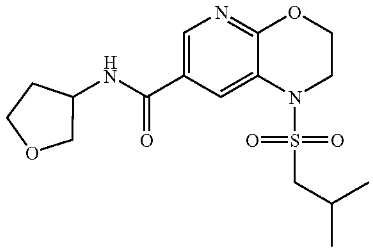 | N-cyclopentyl-1-(isobutylsulfonyl)-2,3-dihydro-1H-pyrido[2,3-b][1,4]oxazine-7-carboxamide | $[M + H]^+ = 368.1$ |
| 30 | 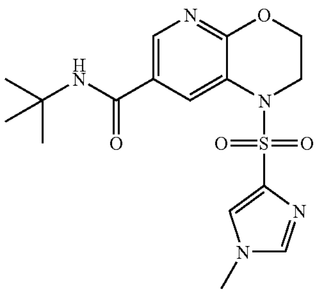 | N-tert-butyl-1-(1-methyl-1H-imidazol-4-ylsulfonyl)-2,3-dihydro-1H-pyrido-[2,3-b][1,4]oxazine-7-carboxamide | $[M + H]^+ = 380.2$ |
| 31 | 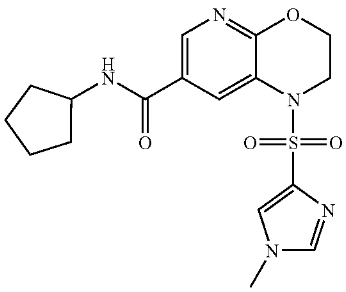 | N-cyclopentyl-1-(1-methyl-1H-imidazol-4-ylsulfonyl)-2,3-dihydro-1H-pyrido[2,3-b][1,4] oxazine-7-carboxamide | $[M + H]^+ = 392.3$ |
| 32 | 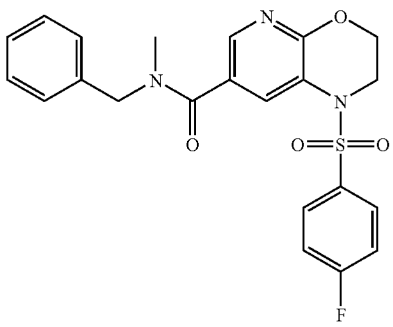 | N-benzyl-1-(4-fluorophenylsulfonyl)-N-methyl-2,3-dihydro-1H-pyrido[2,3-b][1,4]oxazine-7-carboxamide | $[M + H]^+ = 442.1$ |

TABLE 4-continued

| Example | Compound | Name | LCMS |
|---|---|---|---|
| 33 | 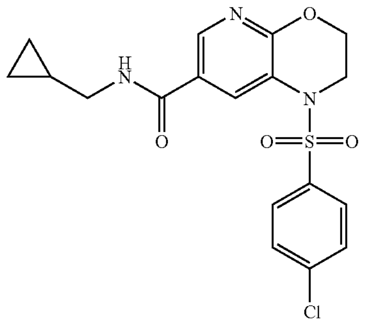 | 1-(4-chlorophenyl-sulfonyl)-N-(cyclopropyl-methyl)-2,3-dihydro-1H-pyrido[2,3-b][1,4]oxazine-7-carboxamide | $[M + H]^+ = 408.0$ |
| 34 | 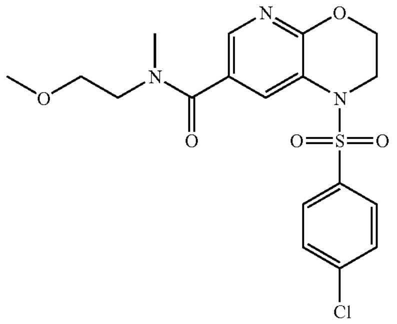 | 1-(4-chlorophenyl-sulfonyl)-N-(2-methoxy-ethyl)-N-methyl-2,3-dihydro-1H-pyrido[2,3-b][1,4]oxazine-7-carboxamide | $[M + H]^+ = 426.1$ |
| 35 | 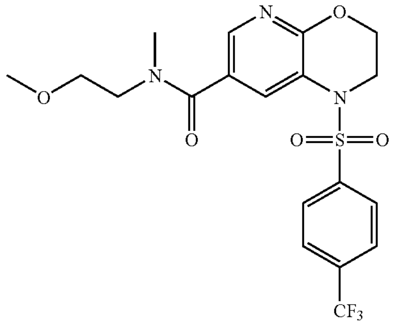 | N-(2-methoxyethyl)-N-methyl-1-(4-(trifluoro-methyl)phenylsulfonyl)-2,3-dihydro-1H-pyrido-[2,3-b][1,4]oxazine-7-carboxamide | $[M + H]^+ = 460.1$ |
| 36 | 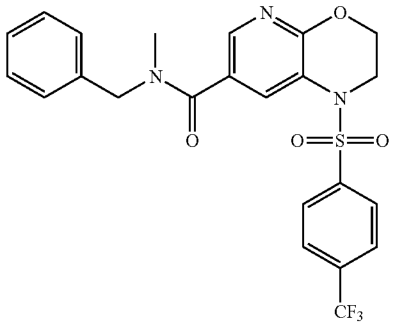 | N-benzyl-N-methyl-1-(4-(trifluoromethyl)phenylsulf-onyl)-2,3-dihydro-1H-pyrido[2,3-b][1,4]oxazine-7-carboxamide | $[M + H]^+ = 492.1$ |

TABLE 4-continued

| Example | Compound | Name | LCMS |
|---|---|---|---|
| 37 | 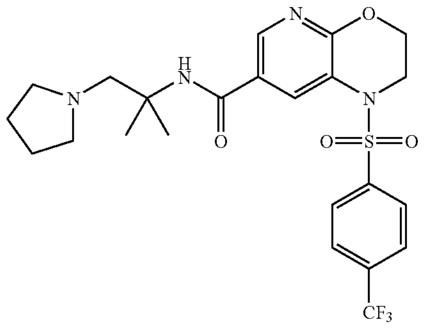 | N-(2-methyl-1-(pyrrolidin-1-yl)propan-2-yl)-1-(4-(trifluoromethyl)phenylsulfonyl)-2,3-dihydro-1H-pyrido[2,3-b][1,4]oxazine-7-carboxamide | $[M + H]^+ = 513.2$ |
| 38 | 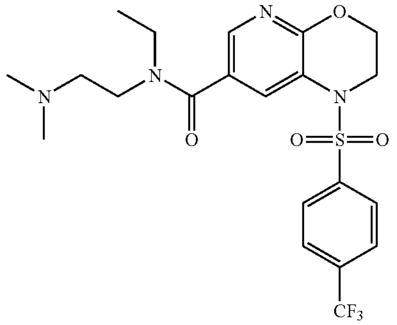 | N-(2-(dimethylamino)-ethyl)-N-ethyl-1-(4-(trifluoromethyl)phenylsulfonyl)-2,3-dihydro-1H-pyrido[2,3-b][1,4]oxazine-7-carboxamide | $[M + H]^+ = 487.1$ |
| 39 | 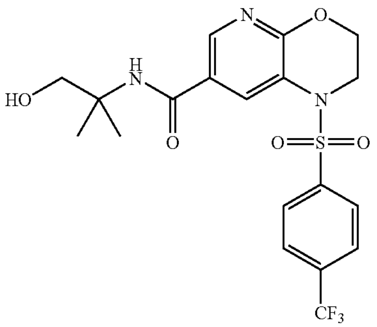 | N-(1-hydroxy-2-methyl-propan-2-yl)-1-(4-(trifluoromethyl)phenylsulfonyl)-2,3-dihydro-1H-pyrido[2,3-b][1,4]oxazine-7-carboxamide | $[M + H]^+ = 460.1$ |
| 40 | 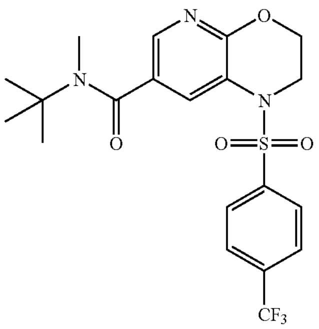 | N-tert-butyl-N-methyl-1-(4-(trifluoromethyl)-phenylsulfonyl)-2,3-dihydro-1H-pyrido[2,3-b][1,4]oxazine-7-carboxamide | $[M + H]^+ = 458.1$ |

TABLE 4-continued

| Example | Compound | Name | LCMS |
| --- | --- | --- | --- |
| 41 | 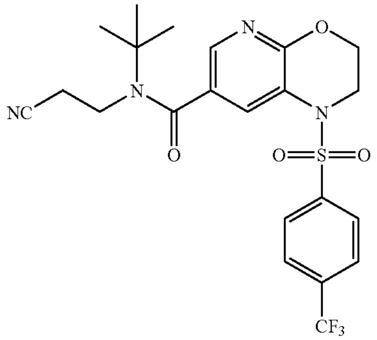 | N-tert-butyl-N-(2-cyanoethyl)-1-(4-(trifluoromethyl)phenylsulfonyl)-2,3-dihydro-1H-pyrido[2,3-b][1,4]oxazine-7-carboxamide | $[M + H]^+ = 497.1$ |
| 42 | 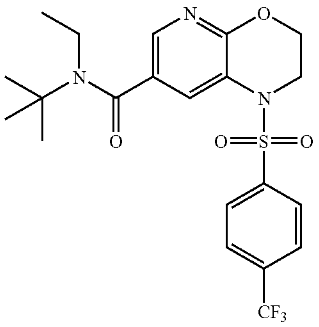 | N-tert-butyl-N-ethyl-1-(4-(trifluoromethyl)phenylsulfonyl)-2,3-dihydro-1H-pyrido[2,3-b][1,4]oxazine-7-carboxamide | $[M + H]^+ = 472.1$ |
| 43 | 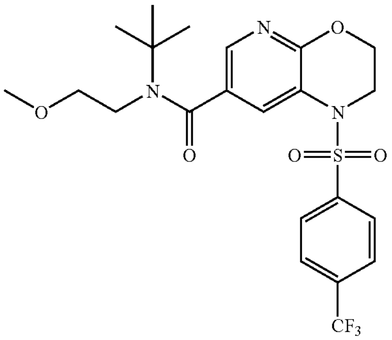 | N-tert-butyl-N-(2-methoxyethyl)-1-(4-(trifluoromethyl)phenylsulfonyl)-2,3-dihydro-1H-pyrido[2,3-b][1,4]oxazine-7-carboxamide | $[M + H]^+ = 502.1$ |
| 44 | 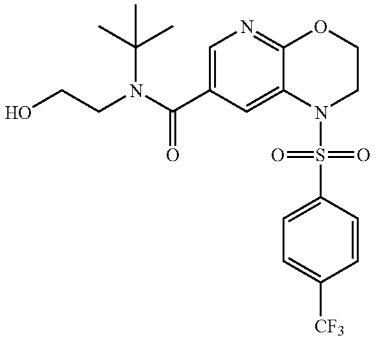 | N-tert-butyl-N-(2-hydroxyethyl)-1-(4-(trifluoromethyl)phenylsulfonyl)-2,3-dihydro-1H-pyrido[2,3-b][1,4]oxazine-7-carboxamide | $[M + H]^+ = 488.1$ |

TABLE 4-continued

| Example | Compound | Name | LCMS |
|---|---|---|---|
| 45 | 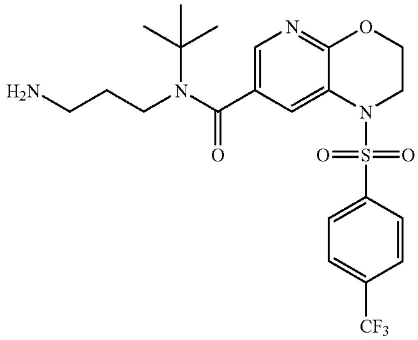 | N-(3-aminopropyl)-N-tert-butyl-1-(4-(trifluoromethyl)phenylsulfonyl)-2,3-dihydro-1H-pyrido[2,3-b][1,4]oxazine-7-carboxamide | $[M + H]^+ = 501.2$ |
| 46 | 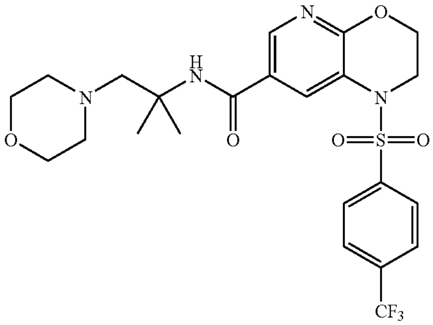 | N-(2-methyl-1-morpholinopropan-2-yl)-1-(4-(trifluoromethyl) phenylsulfonyl)-2,3-dihydro-1H-pyrido[2,3-b][1,4]oxazine-7-carboxamide | $[M + H]^+ = 529.2$ |
| 47 | 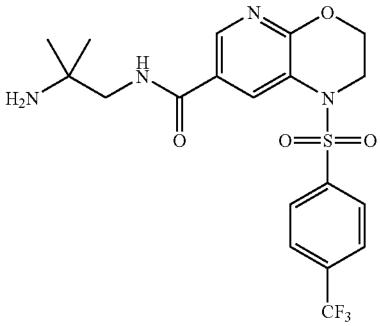 | N-(2-amino-2-methylpropyl)-1-(4-(trifluoromethyl)phenylsulfonyl)-2,3-dihydro-1H-pyrido[2,3-b][1,4]oxazine-7-carboxamide | $[M + H]^+ = 459.1$ |
| 48 | 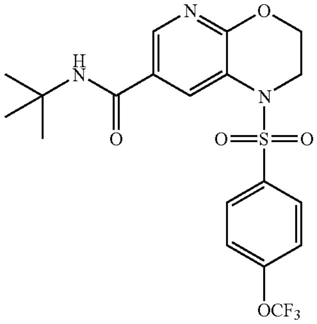 | N-tert-butyl-1-(4-(trifluoromethoxy)phenylsulfonyl)-2,3-dihydro-1H-pyrido[2,3-b][1,4]oxazine-7-carboxamide | $[M + H]^+ = 460.1$ |

TABLE 4-continued

| Example | Compound | Name | LCMS |
| --- | --- | --- | --- |
| 49 | 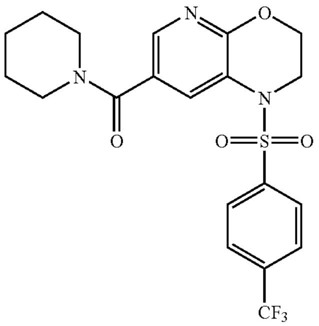 | piperidin-1-yl(1-(4-(trifluoromethyl)phenylsulfonyl)-2,3-dihydro-1H-pyrido[2,3-b][1,4]oxazin-7-yl)methanone | $[M+H]^+ = 456.1$ |
| 50 | 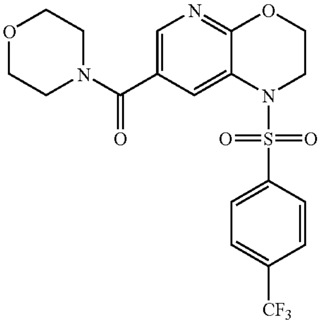 | morpholino(1-(4-(trifluoromethyl)phenylsulfonyl)-2,3-dihydro-1H-pyrido[2,3-b][1,4]oxazin-7-yl)methanone | $[M+H]^+ = 458.1$ |
| 51 | 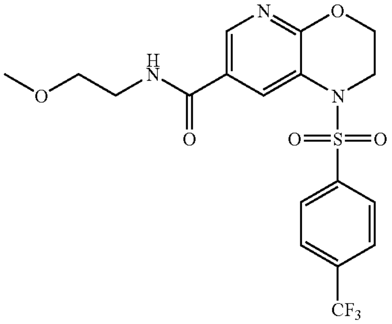 | N-(2-methoxyethyl)-1-(4-(trifluoromethyl)phenysulfonyl)-2,3-dihydro-1H-pyrido[2,3-b][1,4]oxazine-7-carboxamide | $[M+H]^+ = 446.1$ |
| 52 | 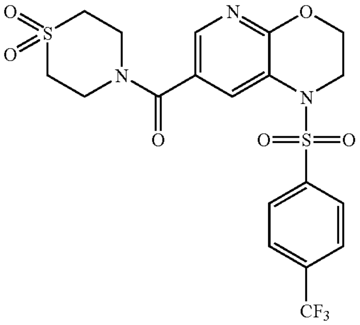 | 1',1'-dioxide-thiomorpholino(1-(4-(trifluoromethyl)phenylsulfonyl)-2,3-dihydro-1H-pyrido[2,3-b][1,4]oxazin-7-yl)methanone | $[M+H]^+ = 506.1$ |
| 53 | 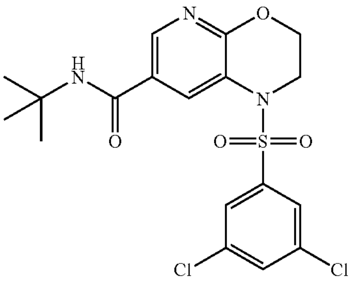 | N-tert-butyl-1-(3,5-dichlorophenylsulfonyl)-2,3-dihydro-1H-pyrido[2,3-b][1,4]oxazine-7-carboxamide | $[M+H]^+ = 444.1$ |

TABLE 4-continued

| Example | Compound | Name | LCMS |
| --- | --- | --- | --- |
| 54 | 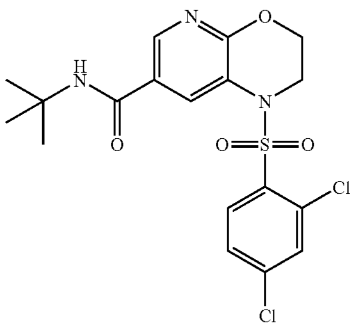 | N-tert-butyl-1-(2,4-dichlorophenylsulfonyl)-2,3-dihydro-1H-pyrido[2,3-b][1,4]oxazine-7-carboxamide | $[M + H]^+ = 444.1$ |
| 55 | 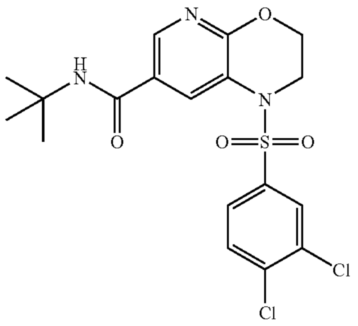 | N-tert-butyl-1-(3,4-dichlorophenylsulfonyl)-2,3-dihydro-1H-pyrido[2,3-b][1,4]oxazine-7-carboxamide | $[M + H]^+ = 444.1$ |
| 56 | 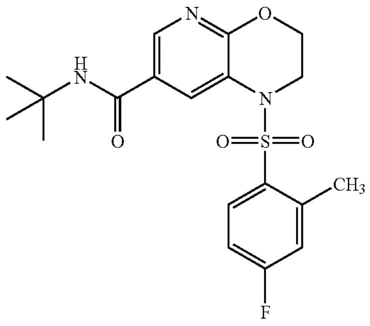 | N-tert-butyl-1-(4-fluoro-2-methylphenylsulfonyl)-2,3-dihydro-1H-pyrido[2,3-b][1,4]oxazine-7-carboxamide | $[M + H]^+ = 408.1$ |
| 57 | 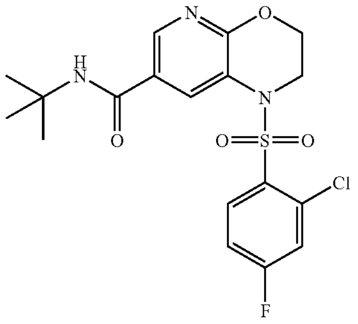 | N-tert-butyl-1-(2-chloro-4-fluorophenylsulfonyl)-2,3-dihydro-1H-pyrido[2,3-b][1,4]oxazine-7-carboxamide | $[M + H]^+ = 428.1$ |

TABLE 4-continued

| Example | Compound | Name | LCMS |
|---|---|---|---|
| 58 | 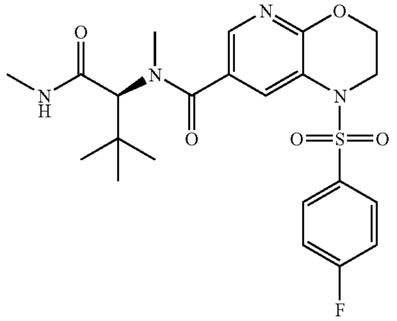 | (S)-N-(3,3-dimethyl-1-(methylamino)-1-oxobutan-2-yl)-1-(4-fluorophenylsulfonyl)-N-methyl-2,3-dihydro-1H-pyrido[2,3-b][1,4]oxazine-7-carboxamide | $[M + H]^+ = 479.1$ |
| 59 | 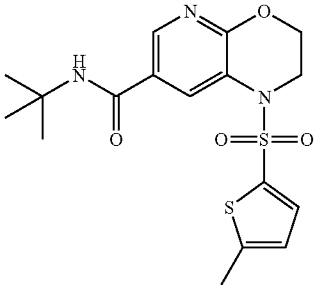 | N-tert-butyl-1-(5-methylthiophen-2-ylsulfonyl)-2,3-dihydro-1H-pyrido[2,3-b][1,4]oxazine-7-carboxamide | $[M + H]^+ = 396.1$ |
| 60 | 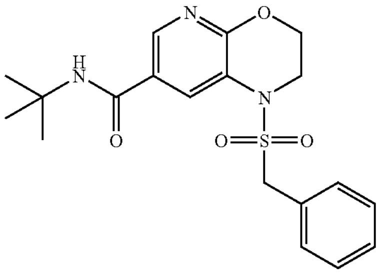 | 1-(benzylsulfonyl)-N-tert-butyl-2,3-dihydro-1H-pyrido[2,3-b][1,4]oxazine-7-carboxamide | $[M + H]^+ = 390.1$ |
| 61 | 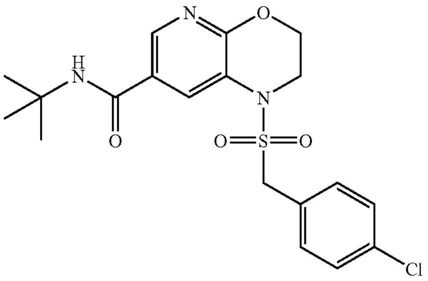 | N-tert-butyl-1-(4-chlorobenzylsulfonyl)-2,3-dihydro-1H-pyrido[2,3-b][1,4]oxazine-7-carboxamide | $[M + H]^+ = 424.1$ |
| 62 | 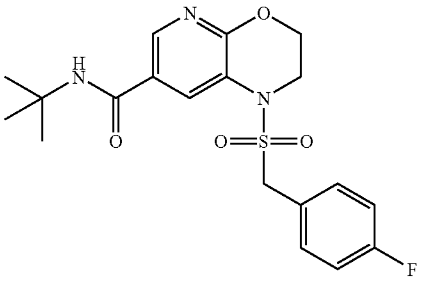 | N-tert-butyl-1-(4-fluorobenzylsulfonyl)-2,3-dihydro-1H-pyrido[2,3-b][1,4]oxazine-7-carboxamide | $[M + H]^+ = 408.1$ |

TABLE 4-continued

| Example | Compound | Name | LCMS |
|---|---|---|---|
| 63 | 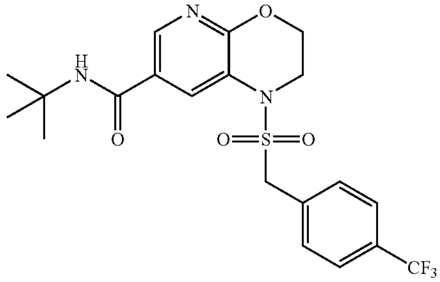 | N-tert-butyl-1-(4-(trifluoromethyl)benzylsulfonyl)-2,3-dihydro-1H-pyrido[2,3-b][1,4]oxazine-7-carboxamide | $[M + H]^+ = 458.1$ |
| 64 | 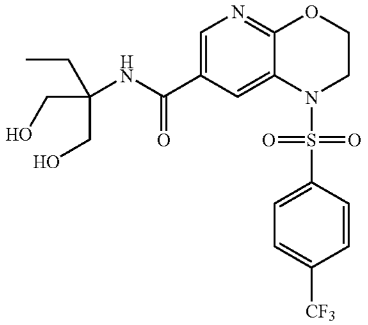 | N-(1-hydroxy-2-(hydroxymethyl)butan-2-yl)-1-(4-(trifluoromethyl)phenylsulfonyl)-2,3-dihydro-1H-pyrido[2,3-b][1,4]oxazine-7-carboxamide | $[M + H]^+ = 490.1$ |
| 65 | 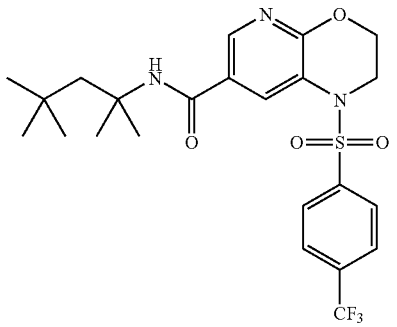 | 1-(4-(trifluoromethyl)-phenylsulfonyl)-N-(2,4,4-trimethylpentan-2-yl)-2,3-dihydro-1H-pyrido[2,3-b][1,4]oxazine-7-carboxamide | $[M + H]^+ = 500.1$ |
| 66 | 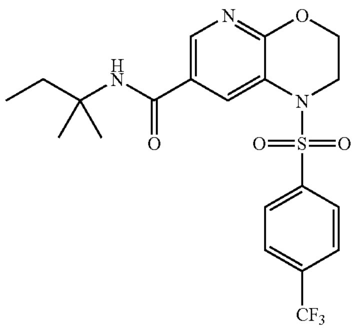 | N-tert-pentyl-1-(4-(trifluoromethyl)phenylsulfonyl)-2,3-dihydro-1H-pyrido[2,3-b][1,4]oxazine-7-carboxamide | $[M + H]^+ = 458.1$ |

TABLE 4-continued

| Example | Compound | Name | LCMS |
|---|---|---|---|
| 67 | 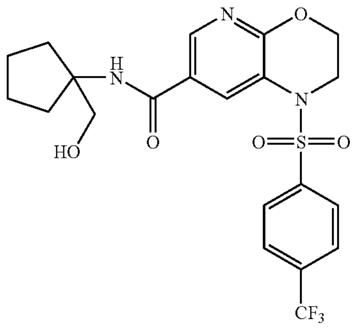 | N-(1-(hydroxymethyl)-cyclopentyl)-1-(4-(trifluoromethyl)phenylsulfonyl)-2,3-dihydro-1H-pyrido[2,3-b][1,4]oxazine-7-carboxamide | $[M + H]^+ = 486.1$ |
| 68 | 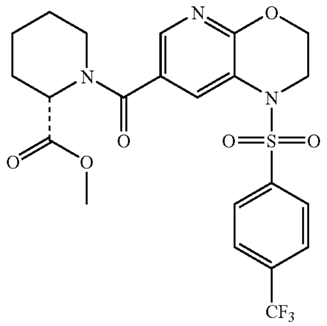 | (S)-methyl 1-(1-(4-(trifluoromethyl)phenylsulfonyl)-2,3-dihydro-1H-pyrido[2,3-b][1,4]oxazine-7-carbonyl)piperidine-2-carboxylate | $[M + H]^+ = 514.1$ |
| 69 | 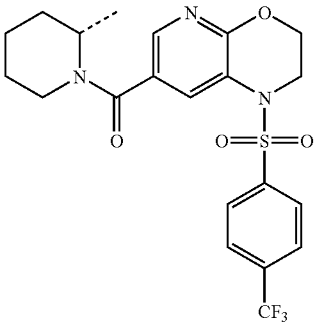 | (S)-(2-methylpiperidin-1-yl)(1-(4-(trifluoromethyl)-phenylsulfonyl)-2,3-dihydro-1H-pyrido[2,3-b][1,4]oxazin-7-yl)-methanone | $[M + H]^+ = 470.1$ |
| 70 | 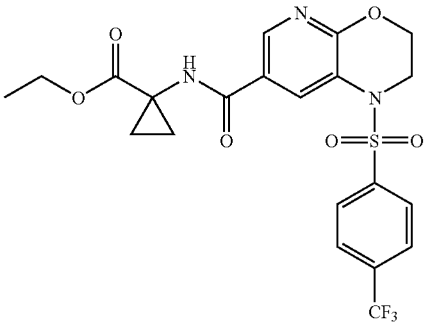 | ethyl 1-(1-(4-(trifluoromethyl)phenylsulfonyl)-2,3-dihydro-1H-pyrido[2,3-b][1,4]oxazine-7-carboxamido)-cyclopropanecarboxylate | $[M + H]^+ = 500.1$ |

TABLE 4-continued

| Example | Compound | Name | LCMS |
| --- | --- | --- | --- |
| 71 | 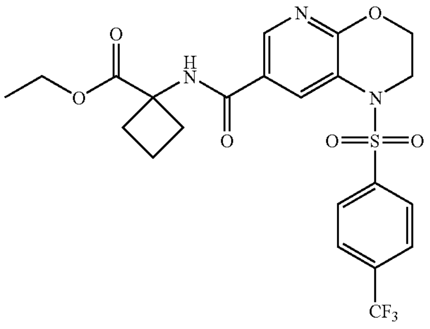 | ethyl 1-(1-(4-(trifluoro-methyl)phenylsulfonyl)-2,3-dihydro-1H-pyrido-[2,3-b][1,4]oxazine-7-carboxamido)cyclo-butanecarboxylate | $[M + H]^+ = 514.1$ |
| 72 | 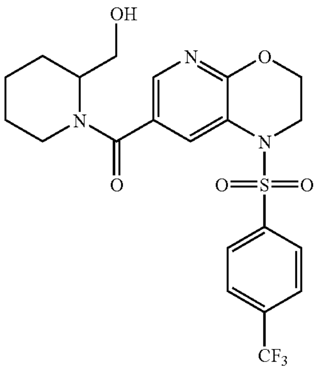 | +/− (2-(hydroxymethyl)piperidin-1-yl)(1-(4-(trifluoro-methyl)phenylsulfonyl)-2,3-dihydro-1H-pyrido[2,3-b][1,4]oxazin-7-yl)methanone | $[M + H]^+ = 486.1$ |
| 73 | 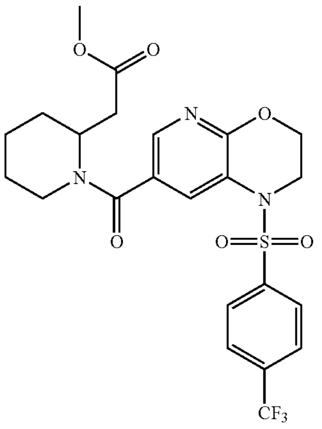 | +/− methyl 2-(1-(1-(4-(trifluoromethyl)phenylsulf-onyl)-2,3-dihydro-1H-pyrido[2,3-b][1,4]oxazine-7-carbonyl)piperidin-2-yl)acetate | $[M + H]^+ = 530.1$ |
| 74 | 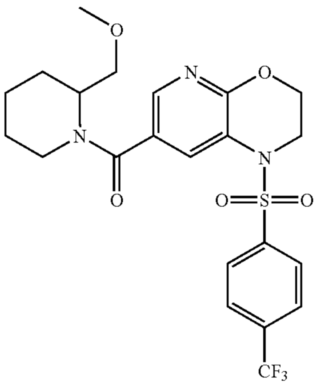 | +/− (2-(methoxymethyl)-piperidin-1-yl)(1-(4-(trifluoromethyl)phenylsulf-onyl)-2,3-dihydro-1H-pyrido[2,3-b][1,4]oxazin-7-yl)methanone | $[M + H]^+ = 500.1$ |

TABLE 4-continued

| Example | Compound | Name | LCMS |
|---|---|---|---|
| 75 | 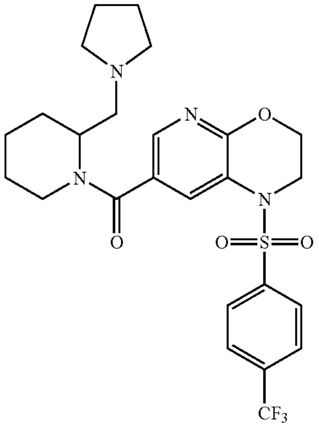 | +/− (2-(pyrrolidin-1-ylmethyl)piperidin-1-yl)(1-(4-(trifluoromethyl)-phenylsulfonyl)-2,3-dihydro-1H-pyrido[2,3-b][1,4]oxazin-7-yl)-methanone | $[M + H]^+ = 539.1$ |
| 76 | 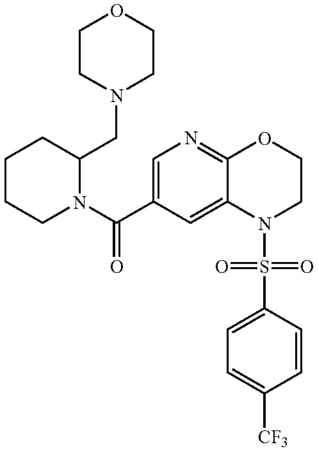 | +/− (2-(morpholino-methyl)piperidin-1-yl)(1-(4-(trifluoromethyl)-phenylsulfonyl)-2,3-dihydro-1H-pyrido[2,3-b][1,4]oxazin-7-yl)methanone | $[M + H]^+ = 555.1$ |
| 77 | 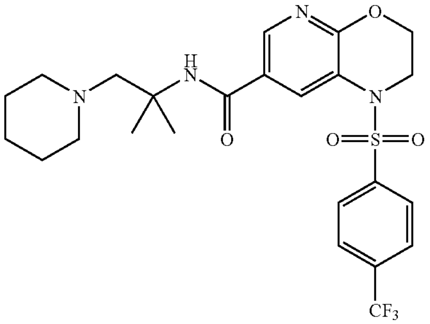 | N-(2-methyl-1-(piperidin-1-yl)propan-2-yl)-1-(4-(trifluoromethyl)phenylsulfonyl)-2,3-dihydro-1H-pyrido[2,3-b][1,4]oxazine-7-carboxamide | $[M + H]^+ = 527.1$ |
| 78 | 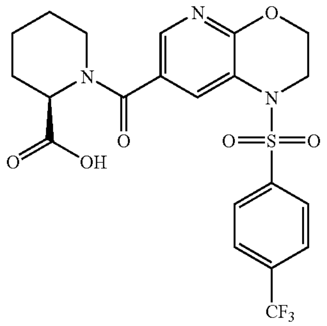 | (R)-1-(1-(4-(trifluoromethyl)phenylsulfonyl)-2,3-dihydro-1H-pyrido-[2,3-b][1,4]oxazine-7-carbonyl)piperidine-2-carboxylic acid | $[M + H]^+ = 500.1$ |

TABLE 4-continued

| Example | Compound | Name | LCMS |
| --- | --- | --- | --- |
| 79 | 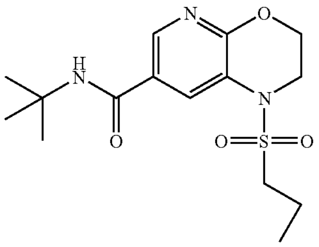 | N-tert-butyl-1-(propylsulfonyl)-2,3-dihydro-1H-pyrido[2,3-b][1,4]oxazine-7-carboxamide | $[M+H]^+ = 342.1$ |
| 80 | 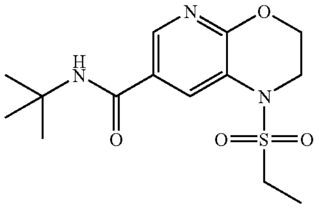 | N-tert-butyl-1-(ethylsulfonyl)-2,3-dihydro-1H-pyrido[2,3-b][1,4]oxazine-7-carboxamide | $[M+H]^+ = 328.1$ |
| 81 | 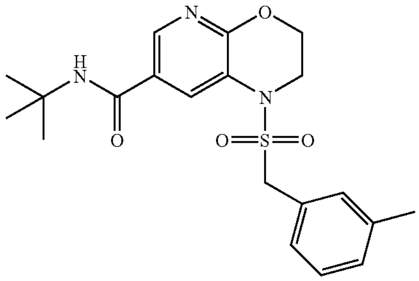 | N-tert-butyl-1-(3-methylbenzylsulfonyl)-2,3-dihydro-1H-pyrido[2,3-b][1,4]oxazine-7-carboxamide | $[M+H]^+ = 404.1$ |
| 82 | 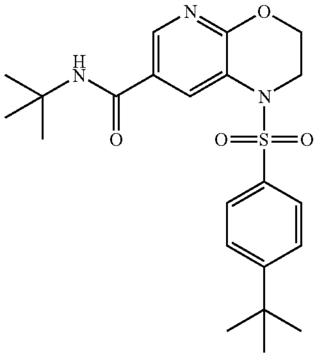 | N-tert-butyl-1-(4-tert-butylphenylsulfonyl)-2,3-dihydro-1H-pyrido[2,3-b][1,4]oxazine-7-carboxamide | $[M+H]^+ = 432.1$ |
| 83 | 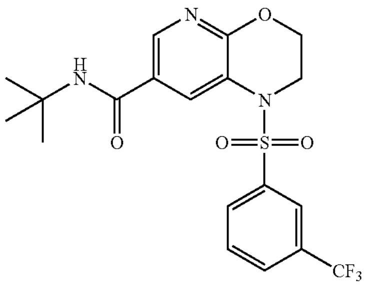 | N-tert-butyl-1-(3-(trifluoromethyl)phenylsulfonyl)-2,3-dihydro-1H-pyrido[2,3-b][1,4]oxazine-7-carboxamide | $[M+H]^+ = 444.1$ |

TABLE 4-continued

| Example | Compound | Name | LCMS |
|---|---|---|---|
| 84 | 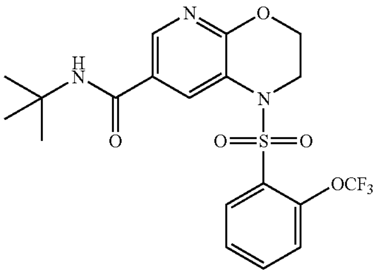 | N-tert-butyl-1-(2-(trifluoromethoxy)phenyl-sulfonyl)-2,3-dihydro-1H-pyrido[2,3-b][1,4]oxazine-7-carboxamide | $[M + H]^+ = 460.1$ |
| 85 | 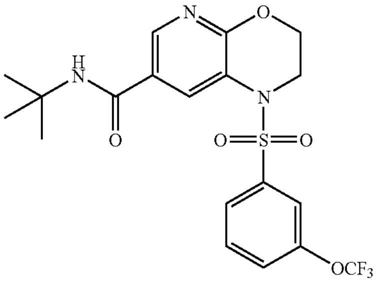 | N-tert-butyl-1-(3-(trifluoromethoxy)phenyl-sulfonyl)-2,3-dihydro-1H-pyrido[2,3-b][1,4]oxazine-7-carboxamide | $[M + H]^+ = 460.1$ |
| 86 | 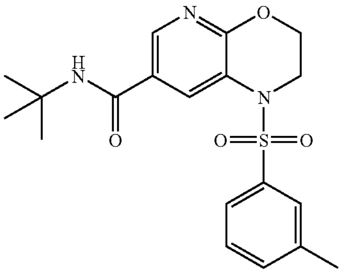 | N-tert-butyl-1-(m-tolylsulfonyl)-2,3-dihydro-1H-pyrido[2,3-b][1,4]oxazine-7-carboxamide | $[M + H]^+ = 390.1$ |
| 87 | 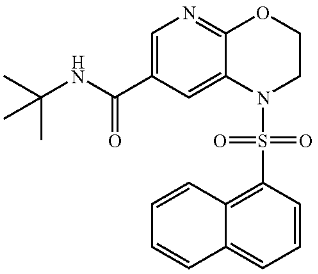 | N-tert-butyl-1-(naphthalen-1-ylsulfonyl)-2,3-dihydro-1H-pyrido[2,3-b][1,4]oxazine-7-carboxamide | $[M + H]^+ = 426.1$ |
| 88 | 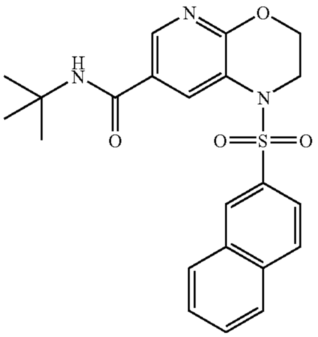 | N-tert-butyl-1-(naphthalen-2-ylsulfonyl)-2,3-dihydro-1H-pyrido[2,3-b][1,4]oxazine-7-carboxamide | $[M + H]^+ = 426.1$ |

TABLE 4-continued

| Example | Compound | Name | LCMS |
| --- | --- | --- | --- |
| 89 | 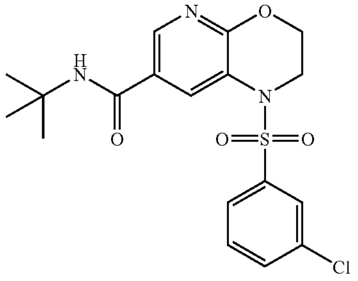 | N-tert-butyl-1-(3-chlorophenylsulfonyl)-2,3-dihydro-1H-pyrido[2,3-b][1,4]oxazine-7-carboxamide | $[M + H]^+ = 410.1$ |
| 90 | 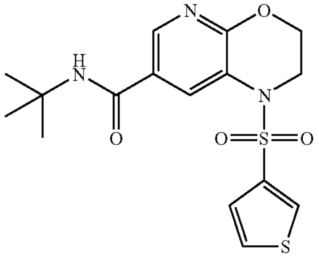 | N-tert-butyl-1-(thiophen-3-ylsulfonyl)-2,3-dihydro-1H-pyrido[2,3-b][1,4]oxazine-7-carboxamide | $[M + H]^+ = 382.1$ |
| 91 | 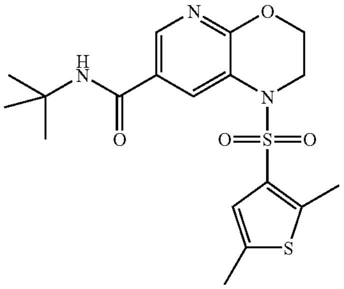 | N-tert-butyl-1-(2,5-dimethylthiophen-3-ylsulfonyl)-2,3-dihydro-1H-pyrido[2,3-b][1,4]oxazine-7-carboxamide | $[M + H]^+ = 410.1$ |
| 92 | 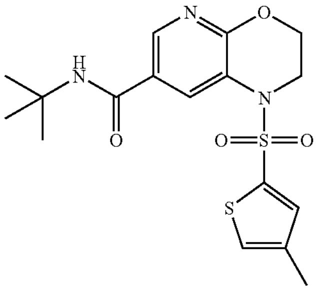 | N-tert-butyl-1-(4-methylthiophen-2-ylsulfonyl)-2,3-dihydro-1H-pyrido[2,3-b][1,4]oxazine-7-carboxamide | $[M + H]^+ = 396.1$ |
| 93 | 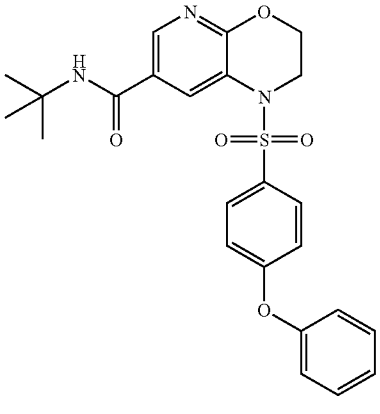 | N-tert-butyl-1-(4-phenoxyphenylsulfonyl)-2,3-dihydro-1H-pyrido[2,3-b][1,4]oxazine-7-carboxamide | $[M + H]^+ = 468.1$ |

TABLE 4-continued

| Example | Compound | Name | LCMS |
|---|---|---|---|
| 94 | 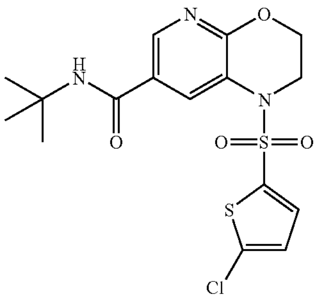 | N-tert-butyl-1-(5-chlorothiophen-2-ylsulfonyl)-2,3-dihydro-1H-pyrido[2,3-b][1,4]oxazine-7-carboxamide | $[M + H]^+ = 415.9$ |
| 95 | 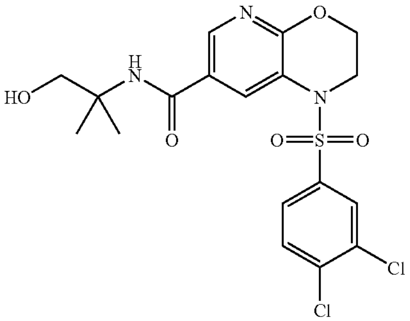 | 1-(3,4-dichlorophenylsulfonyl)-N-(1-hydroxy-2-methylpropan-2-yl)-2,3-dihydro-1H-pyrido[2,3-b][1,4]oxazine-7-carboxamide | $[M + H]^+ = 459.9$ |
| 96 | 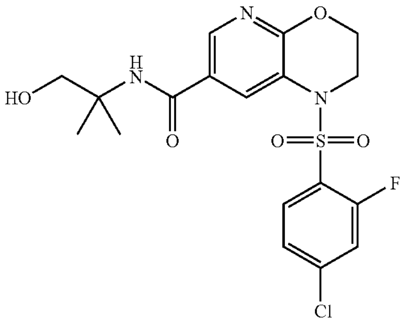 | 1-(4-chloro-2-fluorophenylsulfonyl)-N-(1-hydroxy-2-methylpropan-2-yl)-2,3-dihydro-1H-pyrido[2,3-b][1,4]oxazine-7-carboxamide | $[M + H]^+ = 444.1$ |
| 97 | 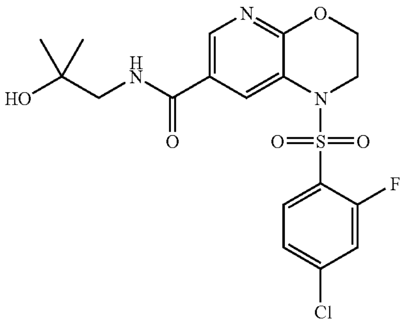 | 1-(4-chloro-2-fluorophenylsulfonyl)-N-(2-hydroxy-2-methylpropyl)-2,3-dihydro-1H-pyrido[2,3-b][1,4]oxazine-7-carboxamide | $[M + H]^+ = 444.1$ |
| 98 | 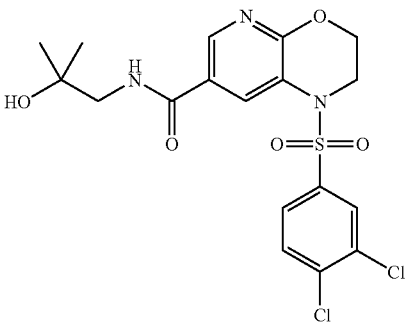 | 1-(3,4-dichlorophenylsulfonyl)-N-(2-hydroxy-2-methylpropyl)-2,3-dihydro-1H-pyrido[2,3-b][1,4]oxazine-7-carboxamide | $[M + H]^+ = 460.1$ |

TABLE 4-continued

| Example | Compound | Name | LCMS |
|---|---|---|---|
| 99 | 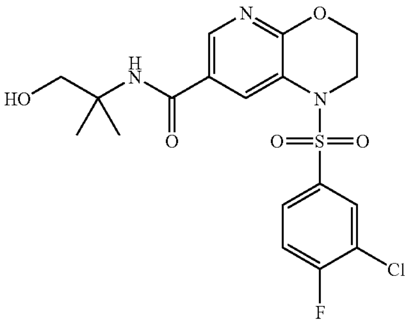 | 1-(3-chloro-4-fluorophenylsulfonyl)-N-(1-hydroxy-2-methylpropan-2-yl)-2,3-dihydro-1H-pyrido[2,3-b][1,4]oxazine-7-carboxamide | $[M + H]^+ = 444.1$ |
| 100 | 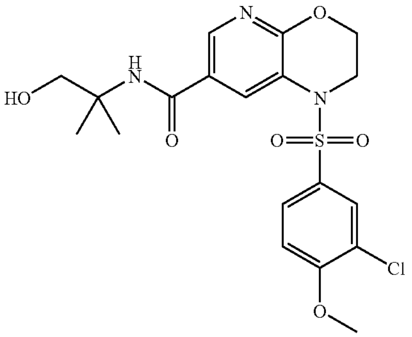 | 1-(3-chloro-4-methoxyphenylsulfonyl)-N-(1-hydroxy-2-methylpropan-2-yl)-2,3-dihydro-1H-pyrido[2,3-b][1,4]oxazine-7-carboxamide | $[M + H]^+ = 456.1$ |
| 101 | 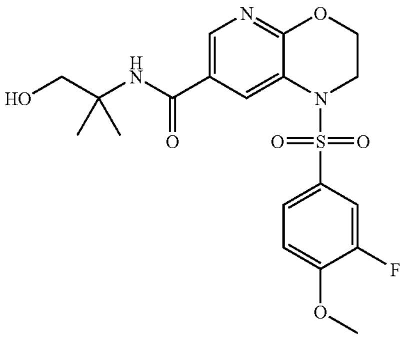 | 1-(3-fluoro-4-methoxyphenylsulfonyl)-N-(1-hydroxy-2-methylpropan-2-yl)-2,3-dihydro-1H-pyrido[2,3-b][1,4]oxazine-7-carboxamide | $[M + H]^+ = 440.1$ |
| 102 | 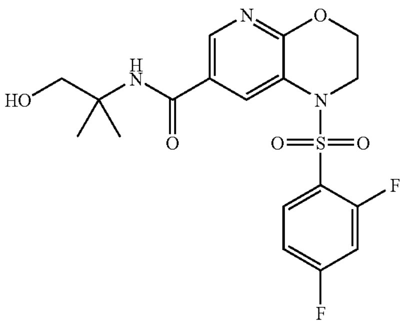 | 1-(2,4-difluorophenylsulfonyl)-N-(1-hydroxy-2-methylpropan-2-yl)-2,3-dihydro-1H-pyrido[2,3-b][1,4]oxazine-7-carboxamide | $[M + H]^+ = 428.1$ |

TABLE 4-continued

| Example | Compound | Name | LCMS |
| --- | --- | --- | --- |
| 103 | 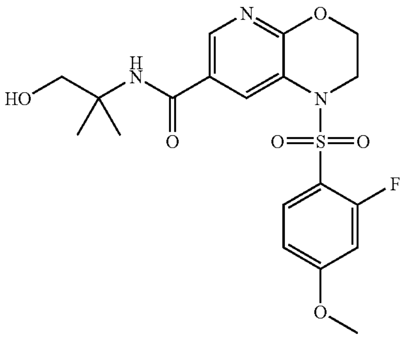 | 1-(2-fluoro-4-methoxyphenylsulfonyl)-N-(1-hydroxy-2-methylpropan-2-yl)-2,3-dihydro-1H-pyrido[2,3-b][1,4]oxazine-7-carboxamide | $[M + H]^+ = 440.1$ |
| 104 | 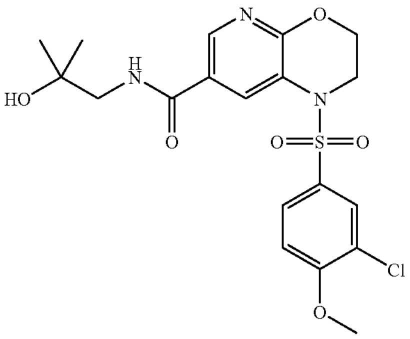 | 1-(3-chloro-4-methoxyphenylsulfonyl)-N-(2-hydroxy-2-methylpropyl)-2,3-dihydro-1H-pyrido[2,3-b][1,4]oxazine-7-carboxamide | $[M + H]^+ = 456.1$ |
| 105 | 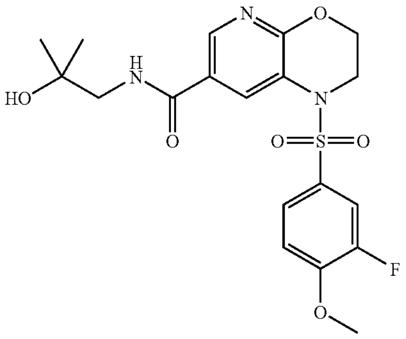 | 1-(3-fluoro-4-methoxyphenylsulfonyl)-N-(2-hydroxy-2-methylpropyl)-2,3-dihydro-1H-pyrido[2,3-b][1,4]oxazine-7-carboxamide | $[M + H]^+ = 440.1$ |
| 106 | 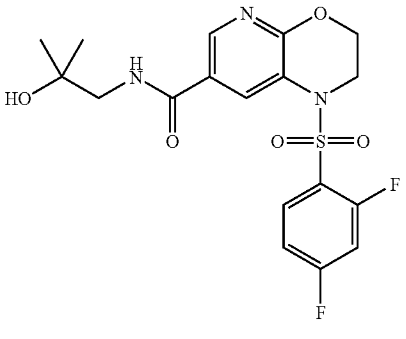 | 1-(2,4-difluorophenylsulfonyl)-N-(2-hydroxy-2-methylpropyl)-2,3-dihydro-1H-pyrido[2,3-b][1,4]oxazine-7-carboxamide | $[M + H]^+ = 428.1$ |

TABLE 4-continued

| Example | Compound | Name | LCMS |
|---|---|---|---|
| 107 | 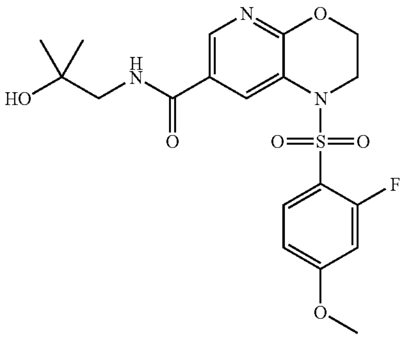 | 1-(2-fluoro-4-methoxyphenylsulfonyl)-N-(2-hydroxy-2-methylpropyl)-2,3-dihydro-1H-pyrido[2,3-b][1,4]oxazine-7-carboxamide | $[M+H]^+ = 440.1$ |
| 108 | 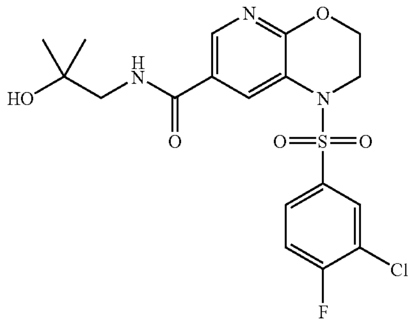 | 1-(3-chloro-4-fluorophenylsulfonyl)-N-(2-hydroxy-2-methylpropyl)-2,3-dihydro-1H-pyrido[2,3-b][1,4]oxazine-7-carboxamide | $[M+H]^+ = 444.1$ |
| 109 | 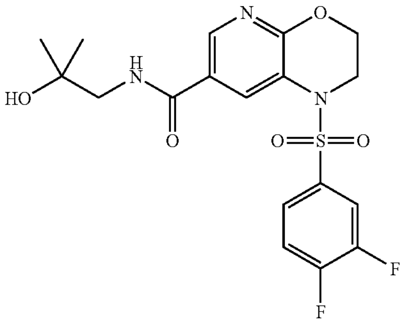 | 1-(3,4-difluorophenylsulfonyl)-N-(2-hydroxy-2-methylpropyl)-2,3-dihydro-1H-pyrido[2,3-b][1,4]oxazine-7-carboxamide | $[M+H]^+ = 428.1$ |
| 110 | 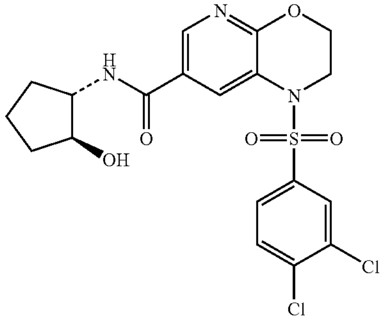 | 1-(3,4-dichlorophenylsulfonyl)-N-((1S,2S)-2-hydroxycyclopentyl)-2,3-dihydro-1H-pyrido[2,3-b][1,4]oxazine-7-carboxamide | $[M+H]^+ = 472.0$ |

TABLE 4-continued

| Example | Compound | Name | LCMS |
|---|---|---|---|
| 111 | 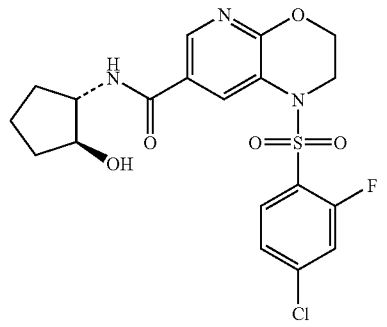 | 1-(4-chloro-2-fluorophenylsulfonyl)-N-((1S,2S)-2-hydroxycyclopentyl)-2,3-dihydro-1H-pyrido[2,3-b][1,4]oxazine-7-carboxamide | $[M + H]^+ = 456.1$ |
| 112 | 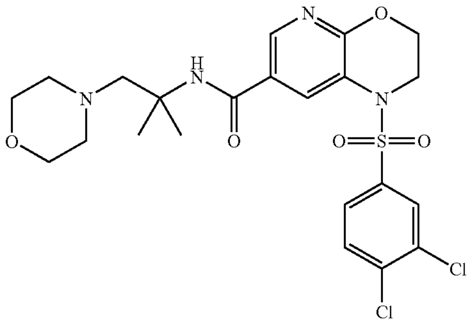 | 1-(3,4-dichlorophenylsulfonyl)-N-(2-methyl-1-morpholinopropan-2-yl)-2,3-dihydro-1H-pyrido[2,3-b][1,4]oxazine-7-carboxamide | $[M + H]^+ = 529.1$ |
| 113 | 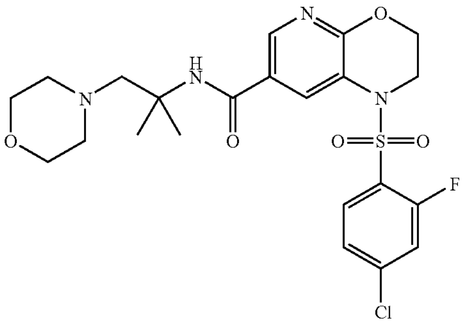 | 1-(4-chloro-2-fluorophenylsulfonyl)-N-(2-methyl-1-morpholinopropan-2-yl)-2,3-dihydro-1H-pyrido[2,3-b][1,4]oxazine-7-carboxamide | $[M + H]^+ = 513.1$ |
| 114 | 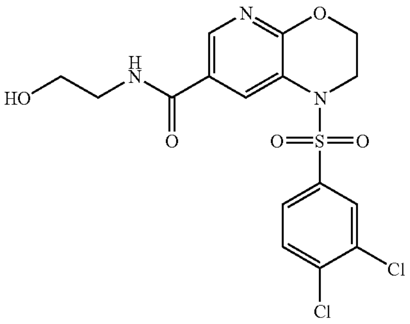 | 1-(3,4-dichlorophenyl-sulfonyl)-N-(2-hydroxyethyl)-2,3-dihydro-1H-pyrido[2,3-b][1,4]oxazine-7-carboxamide | $[M + H]^+ = 432.1$ |

TABLE 4-continued

| Example | Compound | Name | LCMS |
| --- | --- | --- | --- |
| 115 | 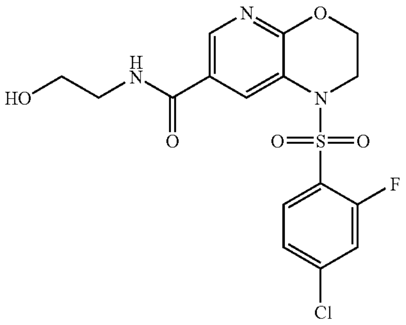 | 1-(4-chloro-2-fluorophenylsulfonyl)-N-(2-hydroxyethyl)-2,3-dihydro-1H-pyrido[2,3-b][1,4]oxazine-7-carboxamide | $[M + H]^+ = 416.1$ |
| 116 | 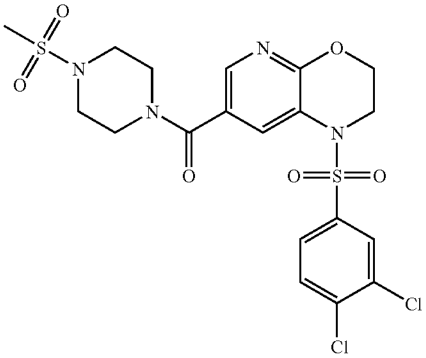 | (1-(3,4-dichloro-phenylsulfonyl)-2,3-dihydro-1H-pyrido[2,3-b][1,4]oxazin-7-yl)(4-(methylsulfonyl)piperazin-1-yl)methanone | $[M + H]^+ = 535.0$ |
| 117 | 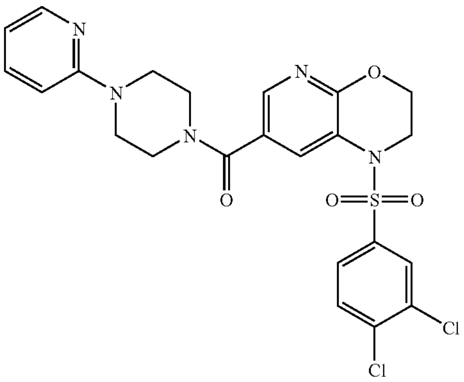 | (1-(3,4-dichlorophenyl-sulfonyl)-2,3-dihydro-1H-pyrido[2,3-b][1,4]oxazin-7-yl)(4-(pyridin-2-ylsulfonyl)piperazin-1-yl)methanone | $[M + H]^+ = 534.1$ |
| 118 | 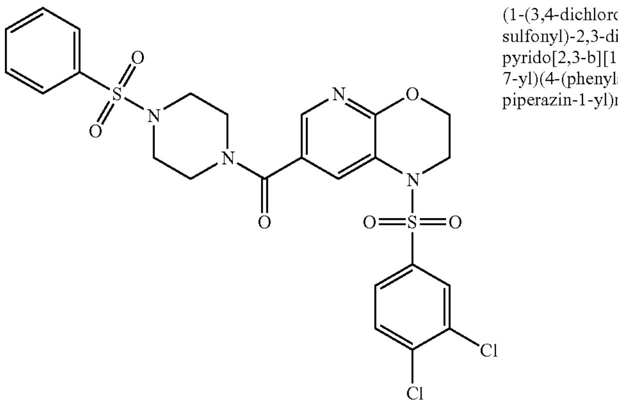 | (1-(3,4-dichlorophenyl-sulfonyl)-2,3-dihydro-1H-pyrido[2,3-b][1,4]oxazin-7-yl)(4-(phenylsulfonyl) piperazin-1-yl)methanone | $[M + H]^+ = 597.0$ |

TABLE 4-continued

| Example | Compound | Name | LCMS |
|---|---|---|---|
| 119 | 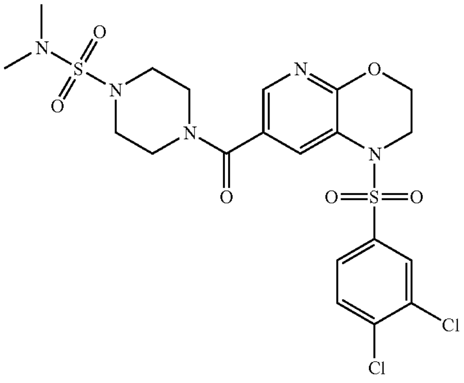 | 4-(1-(3,4-dichlorophenylsulfonyl)-2,3-dihydro-1H-pyrido [2,3-b][1,4]oxazine-7-carbonyl)-N,N-dimethyl piperazine-1-sulfonamide | $[M + H]^+ = 564.1$ |
| 120 | 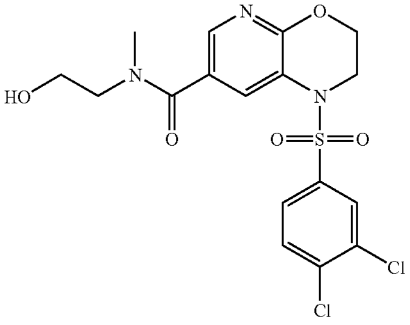 | 1-(3,4-dichlorophenyl-sulfonyl)-N-(2-hydroxy-ethyl)-N-methyl-2,3-dihydro-1H-pyrido[2,3-b][1,4]oxazine-7-carboxamide | $[M + H]^+ = 446.0$ |
| 121 | 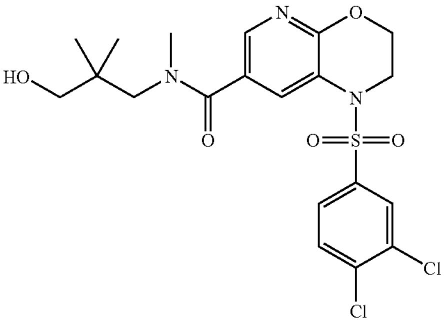 | 1-(3,4-dichlorophenyl sulfonyl)-N-(3-hydroxy-2,2-dimethylpropyl)-N-methyl-2,3-dihydro-1H-pyrido[2,3-b][1,4]oxazine-7-carboxamide | $[M + H]^+ = 488.1$ |
| 122 | 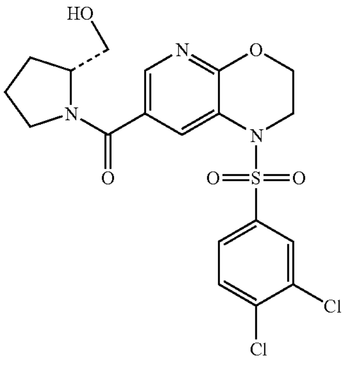 | (R)-(1-(3,4-dichlorophenyl-sulfonyl)-2,3-dihydro-1H-pyrido[2,3-b][1,4]oxazin-7-yl)(2-(hydroxymethyl) pyrrolidin-1-yl)methanone | $[M + H]^+ = 472.0$ |

TABLE 4-continued

| Example | Compound | Name | LCMS |
| --- | --- | --- | --- |
| 123 | 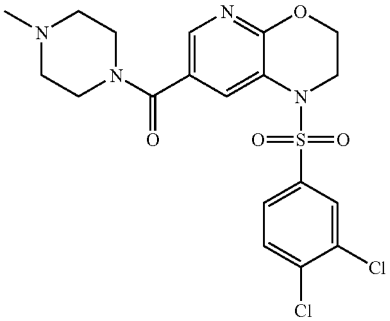 | (1-(3,4-dichlorophenyl-sulfonyl)-2,3-dihydro-1H-pyrido [2,3-b][1,4]oxazin-7-yl)(4-methylpiperazin-1-yl)methanone | $[M + H]^+ = 471.0$ |
| 124 | 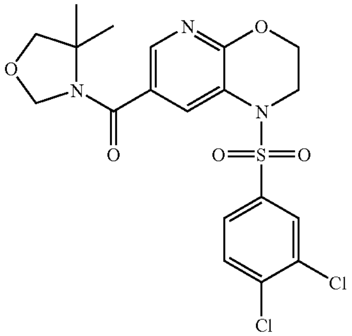 | (1-(3,4-dichlorophenyl-sulfonyl)-2,3-dihydro-1H-pyrido[2,3-b][1,4]oxazin-7-yl)(4,4-dimethyl-oxazolidin-3-yl)methanone | $[M + H]^+ = 472.0$ |
| 125 | 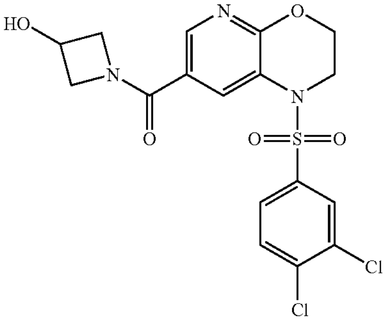 | (1-(3,4-dichlorophenyl-sulfonyl)-2,3-dihydro-1H-pyrido[2,3-b][1,4]oxazin-7-yl)(3-hydroxyazetidin-1-yl)methanone | $[M + H]^+ = 444.0$ |
| 126 | 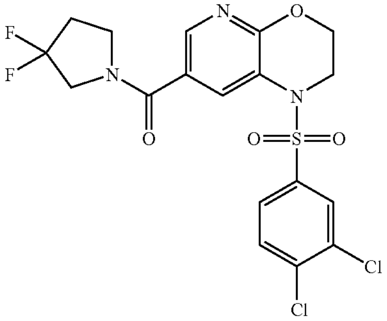 | (1-(3,4-dichlorophenyl-sulfonyl)-2,3-dihydro-1H-pyrido[2,3-b][1,4]oxazin-7-yl)(3,3-difluoro-pyrrolidin-1-yl)methanone | $[M + H]^+ = 478.0$ |

TABLE 4-continued

| Example | Compound | Name | LCMS |
| --- | --- | --- | --- |
| 127 | 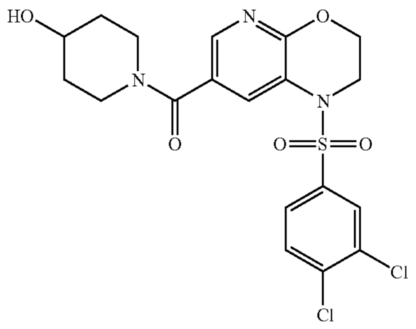 | (1-(3,4-dichlorophenyl-sulfonyl)-2,3-dihydro-1H-pyrido[2,3-b][1,4]oxazin-7-yl)(4-hydroxypiperidin-1-yl)methanone | $[M + H]^+ = 472.0$ |
| 128 | 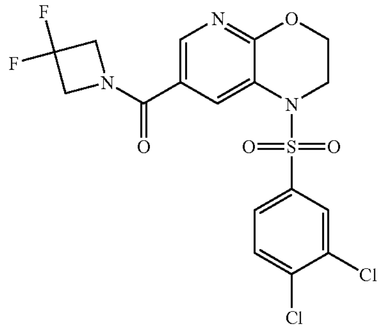 | (1-(3,4-dichlorophenyl-sulfonyl)-2,3-dihydro-1H-pyrido[2,3-b][1,4]oxazin-7-yl)(3,3-difluoroazetidin-1-yl)methanone | $[M + H]^+ = 464.0$ |
| 129 | 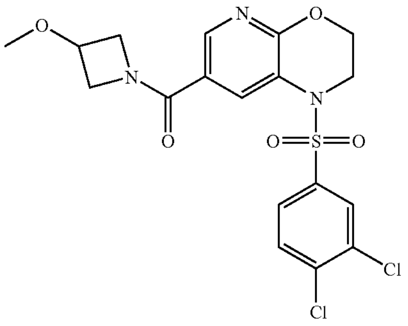 | (1-(3,4-dichlorophenyl-sulfonyl)-2,3-dihydro-1H-pyrido[2,3-b][1,4]oxazin-7-yl)(3-methoxyazetidin-1-yl)methanone | $[M + H]^+ = 458.0$ |
| 130 | 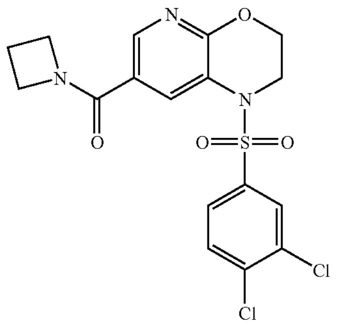 | azetidin-1-yl(1-(3,4-dichlorophenylsulfonyl)-2,3-dihydro-1H-pyrido[2,3-b][1,4]oxazin-7-yl)methanone | $[M + H]^+ = 428.0$ |

TABLE 4-continued

| Example | Compound | Name | LCMS |
| --- | --- | --- | --- |
| 131 | 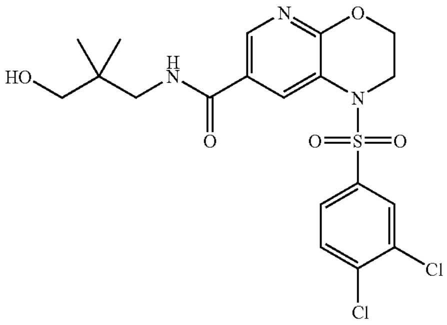 | 1-(3,4-dichlorophenyl-sulfonyl)-N-(3-hydroxy-2,2-dimethylpropyl)-2,3-dihydro-1H-pyrido[2,3-b][1,4]oxazine-7-carboxamide | $[M + H]^+ = 474.1$ |
| 132 | 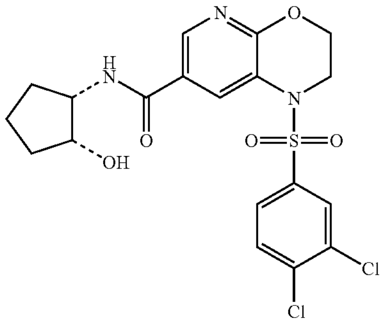 | 1-(3,4-dichlorophenyl-sulfonyl)-N-((1S,2R)-2-hydroxycyclopentyl)-2,3-dihydro-1H-pyrido[2,3-b][1,4]oxazine-7-carboxamide | $[M + H]^+ = 472.0$ |
| 133 | 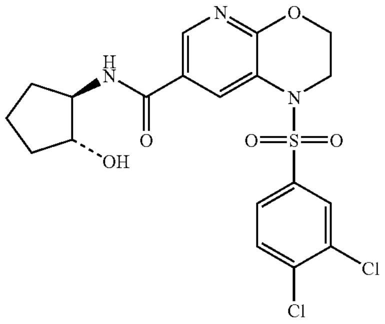 | 1-(3,4-dichlorophenyl-sulfonyl)-N-((1R,2R)-2-hydroxycyclopentyl)-2,3-dihydro-1H-pyrido[2,3-b][1,4]oxazine-7-carboxamide | $[M + H]^+ = 472.1$ |
| 134 | 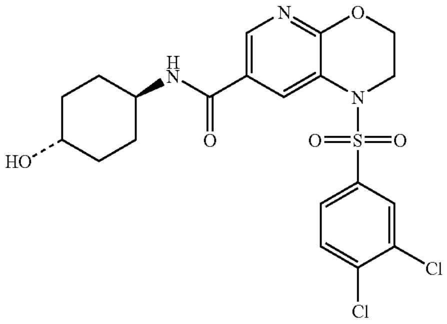 | 1-(3,4-dichlorophenyl-sulfonyl)-N-(trans-4-hydroxycyclohexyl)-2,3-dihydro-1H-pyrido[2,3-b][1,4]oxazine-7-carboxamide | $[M + H]^+ = 486.1$ |

TABLE 4-continued

| Example | Compound | Name | LCMS |
|---|---|---|---|
| 135 | 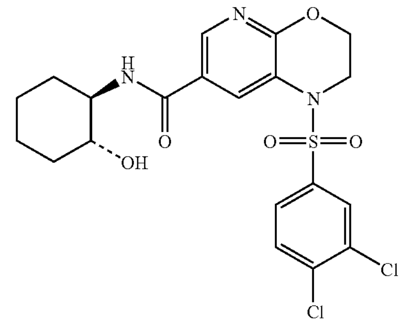 | 1-(3,4-dichlorophenyl-sulfonyl)-N-((1R,2R)-2-hydroxycyclohexyl)-2,3-dihydro-1H-pyrido[2,3-b][1,4]oxazine-7-carboxamide | $[M + H]^+ = 486.1$ |
| 136 | 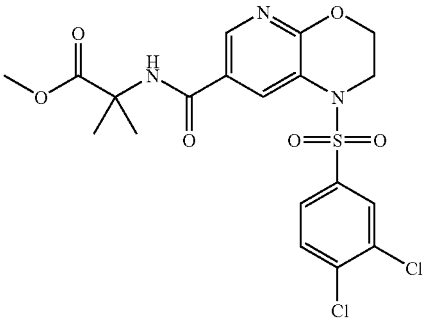 | methyl 2-(1-(3,4-dichlorophenylsulfonyl)-2,3-dihydro-1H-pyrido[2,3-b][1,4]oxazine-7-carboxamido)-2-methylpropanoate | $[M + H]^+ = 488.0$ |
| 137 | 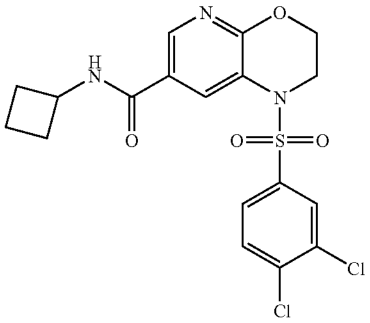 | N-cyclobutyl-1-(3,4-dichlorophenylsulfonyl)-2,3-dihydro-1H-pyrido[2,3-b][1,4]oxazine-7-carboxamide | $[M + H]^+ = 442.0$ |
| 138 | 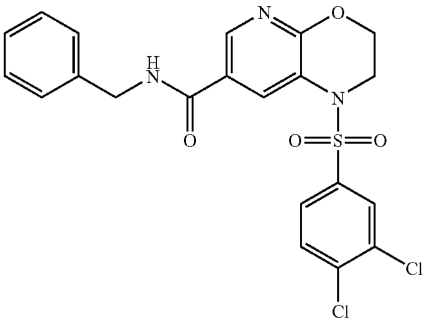 | N-benzyl-1-(3,4-dichlorophenylsulfonyl)-2,3-dihydro-1H-pyrido[2,3-b][1,4]oxazine-7-carboxamide | $[M + H]^+ = 478.0$ |

TABLE 4-continued

| Example | Compound | Name | LCMS |
|---|---|---|---|
| 139 | 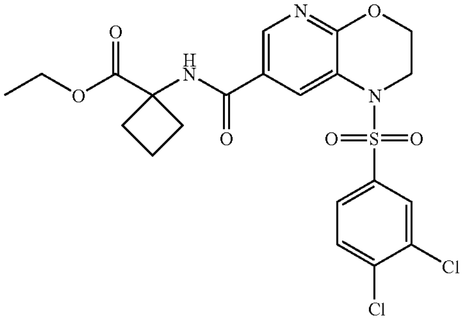 | ethyl 1-(1-(3,4-dichloro-phenylsulfonyl)-2,3-dihydro-1H-pyrido[2,3-b][1,4]oxazine-7-carboxamido)cyclobutane-carboxylate | $[M+H]^+ = 513.9$ |
| 140 | 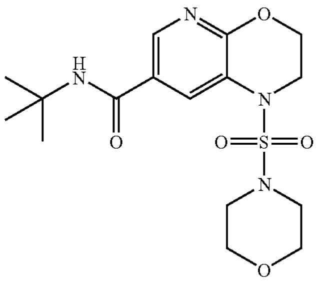 | N-tert-butyl-1-(morpholinosulfonyl)-2,3-dihydro-1H-pyrido[2,3-b][1,4]oxazine-7-carboxamide | $[M+H]^+ = 385.2$ |
| 141 | 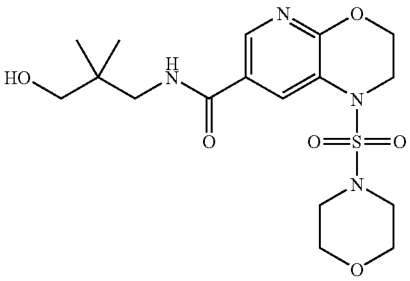 | N-(3-hydroxy-2,2-dimethylpropyl)-1-(morpholinosulfonyl)-2,3-dihydro-1H-pyrido[2,3-b][1,4]oxazine-7-carboxamide | $[M+H]^+ = 415.2$ |
| 142 | 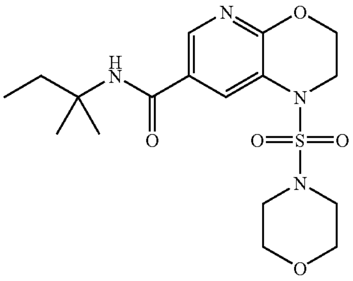 | 1-(morpholinosulfonyl)-N-tert-pentyl-2,3-dihydro-1H-pyrido[2,3-b][1,4]oxazine-7-carboxamide | $[M+H]^+ = 399.2$ |
| 143 | 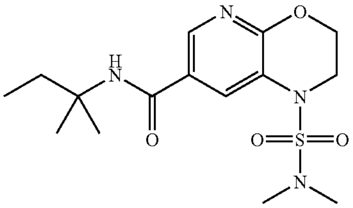 | 1-(N,N-dimethyl-sulfamoyl)-N-tert-pentyl-2,3-dihydro-1H-pyrido[2,3-b][1,4]oxazine-7-carboxamide | $[M+H]^+ = 357.1$ |

TABLE 4-continued

| Example | Compound | Name | LCMS |
|---|---|---|---|
| 144 | 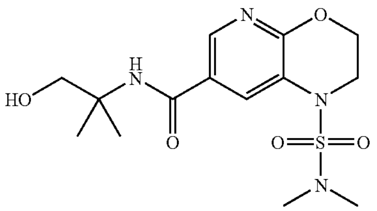 | 1-(N,N-dimethyl-sulfamoyl)-N-(1-hydroxy-2-methylpropan-2-yl)-2,3-dihydro-1H-pyrido[2,3-b][1,4]oxazine-7-carboxamide | $[M + H]^+ = 359.1$ |
| 145 | 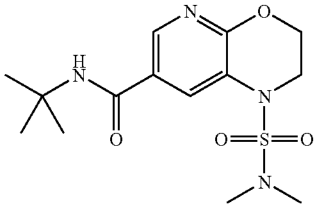 | N-tert-butyl-1-(N,N-dimethylsulfamoyl)-2,3-dihydro-1H-pyrido[2,3-b][1,4]oxazine-7-carboxamide | $[M + H]^+ = 343.1$ |
| 146 | 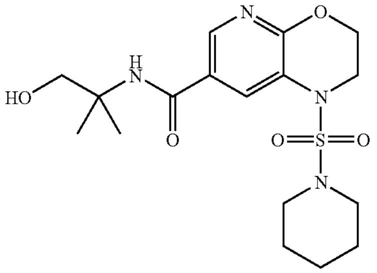 | N-(1-hydroxy-2-methylpropan-2-yl)-1-(piperidin-1-ylsulfonyl)-2,3-dihydro-1H-pyrido[2,3-b][1,4]oxazine-7-carboxamide | $[M + H]^+ = 399.2$ |
| 147 | 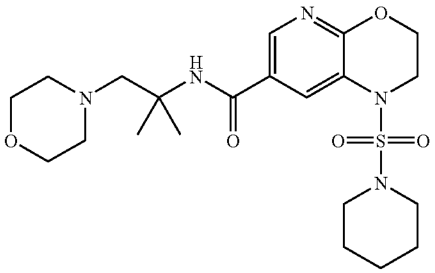 | N-(2-methyl-1-morpholinopropan-2-yl)-1-(piperidin-1-ylsulfonyl)-2,3-dihydro-1H-pyrido[2,3-b][1,4]oxazine-7-carboxamide | $[M + H]^+ = 468.2$ |
| 148 | 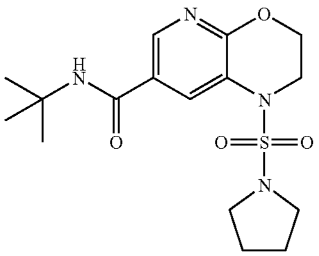 | N-tert-butyl-1-(pyrrolidin-1-ylsulfonyl)-2,3-dihydro-1H-pyrido[2,3-b][1,4]oxazine-7-carboxamide | $[M + H]^+ = 369.2$ |
| 149 | 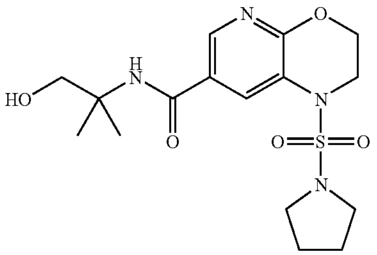 | N-(1-hydroxy-2-methylpropan-2-yl)-1-(pyrrolidin-1-ylsulfonyl)-2,3-dihydro-1H-pyrido[2,3-b][1,4]oxazine-7-carboxamide | $[M + H]^+ = 385.1$ |

TABLE 4-continued

| Example | Compound | Name | LCMS |
| --- | --- | --- | --- |
| 150 | 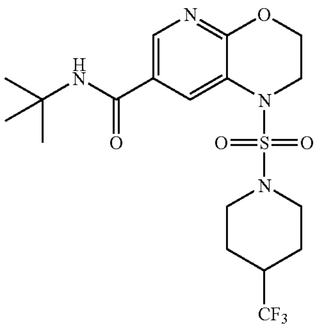 | N-tert-butyl-1-(4-(trifluoromethyl)piperidin-1-ylsulfonyl)-2,3-dihydro-1H-pyrido[2,3-b][1,4]oxazine-7-carboxamide | $[M+H]^+ = 451.1$ |
| 151 | 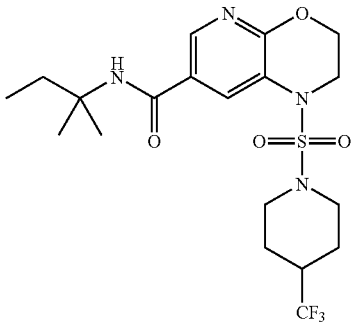 | N-tert-pentyl-1-(4-(trifluoromethyl)piperidin-1-ylsulfonyl)-2,3-dihydro-1H-pyrido[2,3-b][1,4]oxazine-7-carboxamide | $[M+H]^+ = 465.1$ |
| 152 | 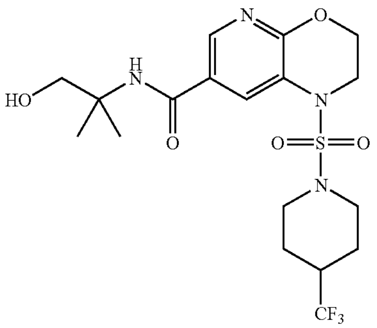 | N-(1-hydroxy-2-methylpropan-2-yl)-1-(4-(trifluoromethyl)piperidin-1-ylsulfonyl)-2,3-dihydro-1H-pyrido[2,3-b][1,4]oxazine-7-carboxamide | $[M+H]^+ = 467.1$ |
| 153 | 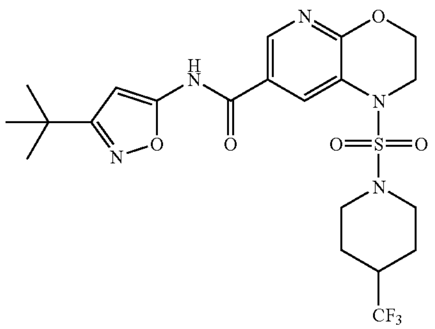 | N-(3-tert-butylisoxazol-5-yl)-1-(4-(trifluoromethyl) piperidin-1-ylsulfonyl)-2,3-dihydro-1H-pyrido[2,3-b][1,4]oxazine-7-carboxamide | $[M+H]^+ = 518.1$ |

TABLE 4-continued

| Example | Compound | Name | LCMS |
|---|---|---|---|
| 154 | 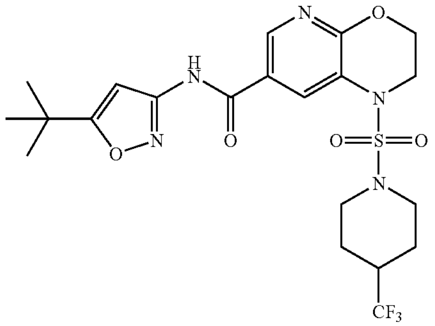 | N-(5-tert-butylisoxazol-3-yl)-1-(4-(trifluoromethyl)piperidin-1-ylsulfonyl)-2,3-dihydro-1H-pyrido[2,3-b][1,4]oxazine-7-carboxamide | $[M + H]^+ = 518.1$ |
| 155 | 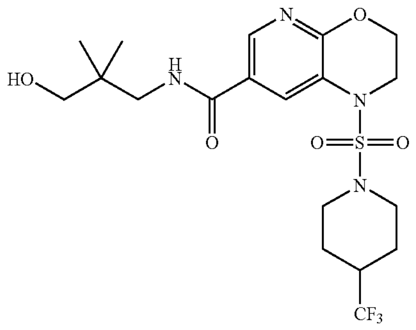 | N-(3-hydroxy-2,2-dimethylpropyl)-1-(4-(trifluoromethyl)piperidin-1-ylsulfonyl)-2,3-dihydro-1H-pyrido[2,3-b][1,4]oxazine-7-carboxamide | $[M + H]^+ = 481.1$ |
| 156 | 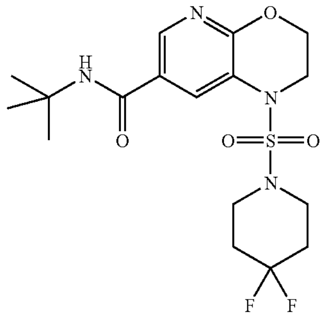 | N-tert-butyl-1-(4,4-difluoropiperidin-1-ylsulfonyl)-2,3-dihydro-1H-pyrido[2,3-b][1,4]oxazine-7-carboxamide | $[M + H]^+ = 419.1$ |
| 157 | 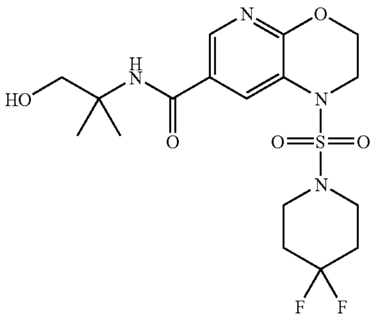 | 1-(4,4-difluoropiperidin-1-ylsulfonyl)-N-(1-hydroxy-2-methylpropan-2-yl)-2,3-dihydro-1H-pyrido[2,3-b][1,4]oxazine-7-carboxamide | $[M + H]^+ = 435.1$ |

TABLE 4-continued

| Example | Compound | Name | LCMS |
| --- | --- | --- | --- |
| 158 | 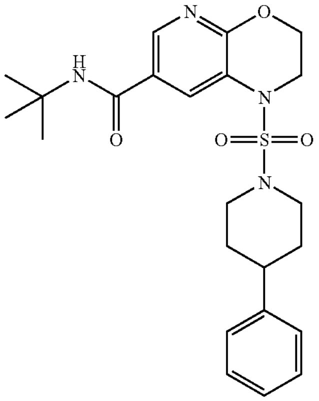 | N-tert-butyl-1-(4-phenylpiperidin-1-ylsulfonyl)-2,3-dihydro-1H-pyrido[2,3-b][1,4]oxazine-7-carboxamide | $[M + H]^+ = 459.2$ |
| 159 | 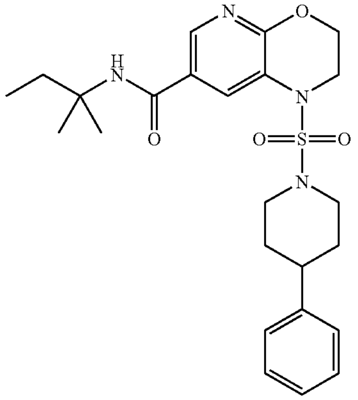 | N-tert-pentyl-1-(4-phenylpiperidin-1-ylsulfonyl)-2,3-dihydro-1H-pyrido[2,3-b][1,4]oxazine-7-carboxamide | $[M + H]^+ = 473.3$ |
| 160 | 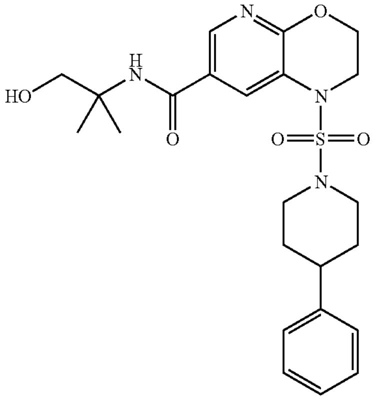 | N-(1-hydroxy-2-methylpropan-2-yl)-1-(4-phenylpiperidin-1-ylsulfonyl)-2,3-dihydro-1H-pyrido[2,3-b][1,4]oxazine-7-carboxamide | $[M + H]^+ = 475.2$ |
| 161 | 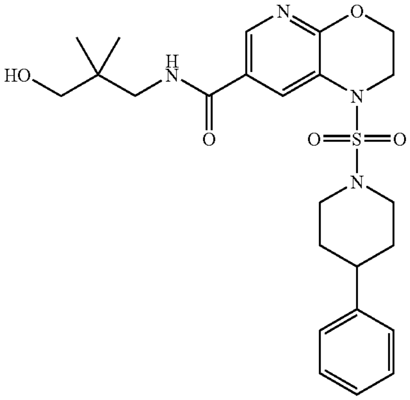 | N-(3-hydroxy-2,2-dimethylpropyl)-1-(4-phenylpiperidin-1-ylsulfonyl)-2,3-dihydro-1H-pyrido[2,3-b][1,4]oxazine-7-carboxamide | $[M + H]^+ = 489.3$ |

TABLE 4-continued

| Example | Compound | Name | LCMS |
|---|---|---|---|
| 162 | 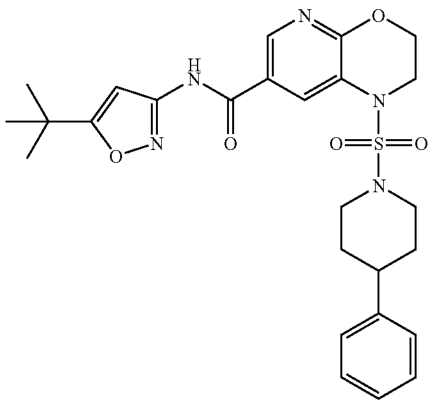 | N-(5-tert-butylisoxazol-3-yl)-1-(4-phenylpiperidin-1-ylsulfonyl)-2,3-dihydro-1H-pyrido[2,3-b][1,4]oxazine-7-carboxamide | $[M + H]^+ = 526.2$ |
| 163 | 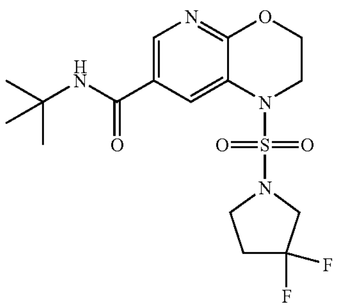 | N-tert-butyl-1-(3,3-difluoropyrrolidin-1-ylsulfonyl)-2,3-dihydro-1H-pyrido[2,3-b][1,4]oxazine-7-carboxamide | $[M + H]^+ = 405.2$ |
| 164 | 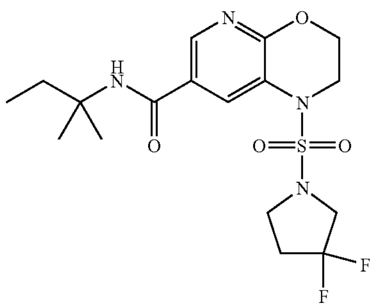 | 1-(3,3-difluoropyrrolidin-1-ylsulfonyl)-N-tert-pentyl-2,3-dihydro-1H-pyrido[2,3-b][1,4]oxazine-7-carboxamide | $[M + H]^+ = 419.3$ |
| 165 | 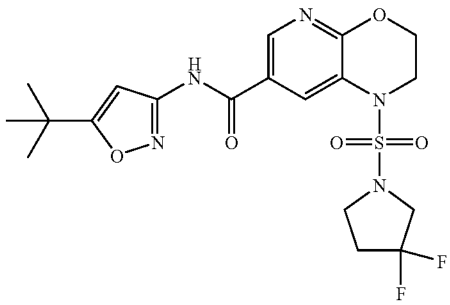 | N-(5-tert-butylisoxazol-3-yl)-1-(3,3-difluoro-pyrrolidin-1-ylsulfonyl)-2,3-dihydro-1H-pyrido-[2,3-b][1,4]oxazine-7-carboxamide | $[M + H]^+ = 472.2$ |

TABLE 4-continued

| Example | Compound | Name | LCMS |
|---|---|---|---|
| 166 | 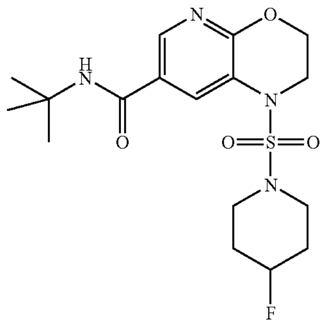 | N-tert-butyl-1-(4-fluoropiperidin-1-ylsulfonyl)-2,3-dihydro-1H-pyrido[2,3-b][1,4]oxazine-7-carboxamide | $[M + H]^+ = 401.2$ |
| 167 | 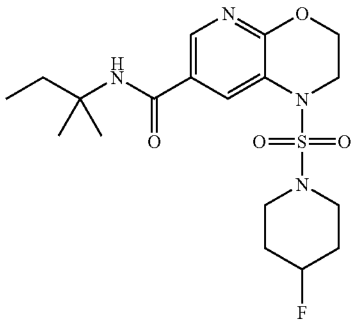 | 1-(4-fluoropiperidin-1-ylsulfonyl)-N-tert-pentyl-2,3-dihydro-1H-pyrido[2,3-b][1,4 ]oxazine-7-carboxamide | $[M + H]^+ = 415.2$ |
| 168 | 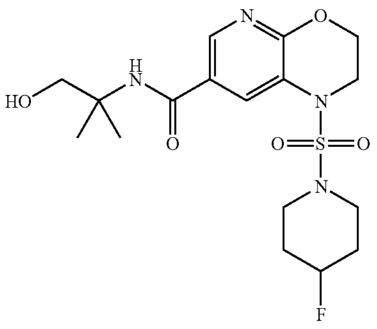 | 1-(4-fluoropiperidin-1-ylsulfonyl)-N-(1-hydroxy-2-methylpropan-2-yl)-2,3-dihydro-1H-pyrido[2,3-b][1,4]oxazine-7-carboxamide | $[M + H]^+ = 417.2$ |
| 169 | 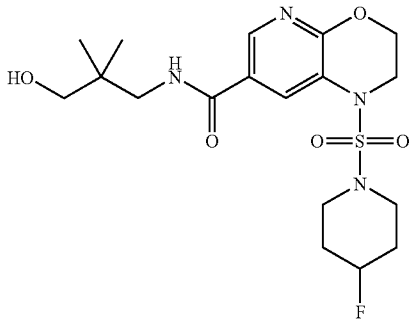 | 1-(4-fluoropiperidin-1-ylsulfonyl)-N-(3-hydroxy-2,2-dimethylpropyl)-2,3-dihydro-1H-pyrido[2,3-b][1,4]oxazine-7-carboxamide | $[M + H]^+ = 431.3$ |

TABLE 4-continued

| Example | Compound | Name | LCMS |
|---|---|---|---|
| 170 | 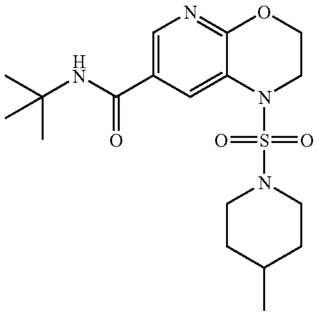 | N-tert-butyl-1-(4-methylpiperidin-1-ylsulfonyl)-2,3-dihydro-1H-pyrido[2,3-b][1,4]oxazine-7-carboxamide | $[M + H]^+ = 397.3$ |
| 171 | 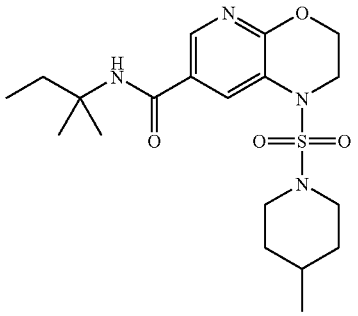 | 1-(4-methylpiperidin-1-ylsulfonyl)-N-tert-pentyl-2,3-dihydro-1H-pyrido[2,3-b][1,4]oxazine-7-carboxamide | $[M + H]^+ = 411.3$ |
| 172 | 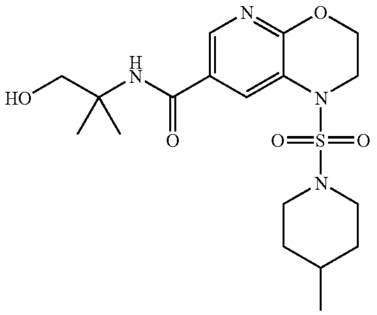 | N-(1-hydroxy-2-methylpropan-2-yl)-1-(4-methylpiperidin-1-ylsulfonyl)-2,3-dihydro-1H-pyrido[2,3-b][1,4]oxazine-7-carboxamide | $[M + H]^+ = 413.3$ |
| 173 | 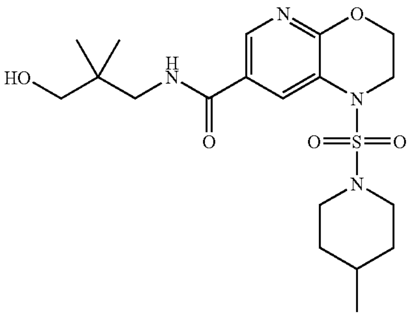 | N-(3-hydroxy-2,2-dimethylpropyl)-1-(4-methylpiperidin-1-ylsulfonyl)-2,3-dihydro-1H-pyrido[2,3-b][1,4] oxazine-7-carboxamide | $[M + H]^+ = 427.3$ |
| 174 | 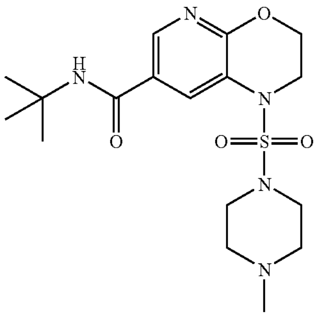 | N-tert-butyl-1-(4-methylpiperazin-1-ylsulfonyl)-2,3-dihydro-1H-pyrido[2,3-b][1,4] oxazine-7-carboxamide | $[M + H]^+ = 398.3$ |

TABLE 4-continued

| Example | Compound | Name | LCMS |
|---|---|---|---|
| 175 | 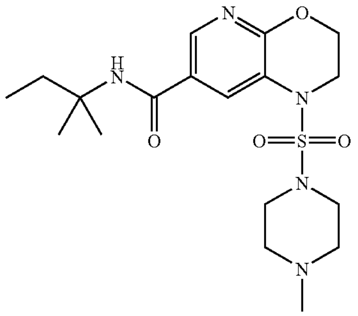 | 1-(4-methylpiperazin-1-ylsulfonyl)-N-tert-pentyl-2,3-dihydro-1H-pyrido[2,3-b][1,4]oxazine-7-carboxamide | $[M + H]^+ = 412.3$ |
| 176 | 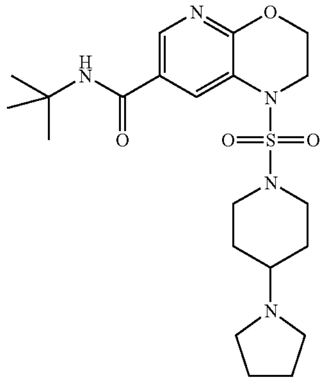 | N-tert-butyl-1-(4-(pyrrolidin-1-yl)piperidin-1-ylsulfonyl)-2,3-dihydro-1H-pyrido[2,3-b][1,4]oxazine-7-carboxamide | $[M + H]^+ = 452.3$ |
| 177 | 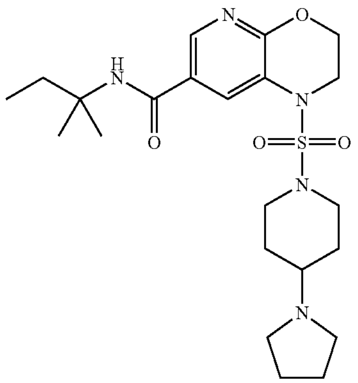 | N-tert-pentyl-1-(4-(pyrrolidin-1-yl)piperidin-1-ylsulfonyl)-2,3-dihydro-1H-pyrido[2,3-b][1,4]oxazine-7-carboxamide | $[M + H]^+ = 466.4$ |
| 178 | 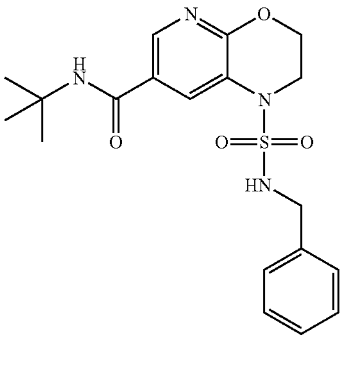 | 1-(N-benzylsulfamoyl)-N-tert-butyl-2,3-dihydro-1H-pyrido[2,3-b][1,4]oxazine-7-carboxamide | $[M + H]^+ = 405.3$ |

TABLE 4-continued

| Example | Compound | Name | LCMS |
|---|---|---|---|
| 179 | 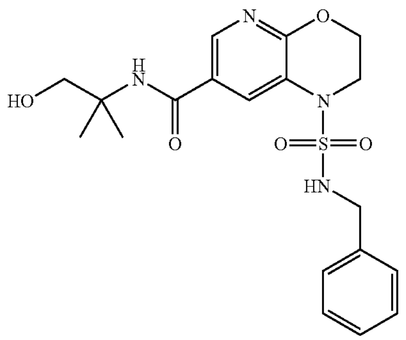 | 1-(N-benzylsulfamoyl)-N-(1-hydroxy-2-methylpropan-2-yl)-2,3-dihydro-1H-pyrido[2,3-b][1,4]oxazine-7-carboxamide | $[M + H]^+ = 421.2$ |
| 180 | 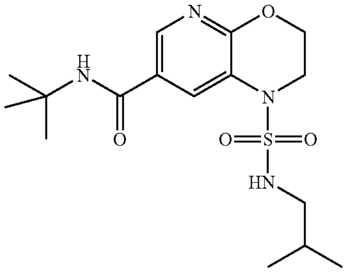 | N-tert-butyl-1-(N-isobutylsulfamoyl)-2,3-dihydro-1H-pyrido[2,3-b][1,4]oxazine-7-carboxamide | $[M + H]^+ = 371.3$ |
| 181 | 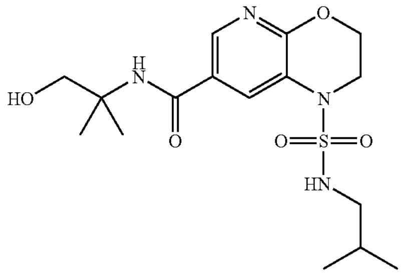 | N-(1-hydroxy-2-methylpropan-2-yl)-1-(N-isobutylsulfamoyl)-2,3-dihydro-1H-pyrido[2,3-b][1,4]oxazine-7-carboxamide | $[M + H]^+ = 387.3$ |
| 182 | 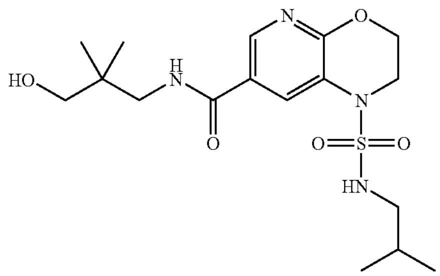 | N-(3-hydroxy-2,2-dimethylpropyl)-1-(N-isobutylsulfamoyl)-2,3-dihydro-1H-pyrido[2,3-b][1,4]oxazine-7-carboxamide | $[M + H]^+ = 401.3$ |
| 183 | 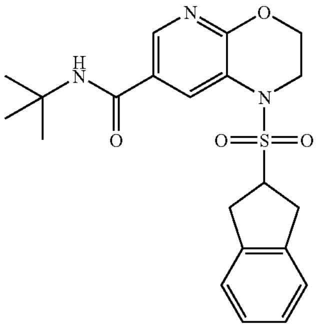 | N-tert-butyl-1-(isoindolin-2-ylsulfonyl)-2,3-dihydro-1H-pyrido[2,3-b][1,4]oxazine-7-carboxamide | $[M + H]^+ = 417.2$ |

TABLE 4-continued

| Example | Compound | Name | LCMS |
|---|---|---|---|
| 184 | 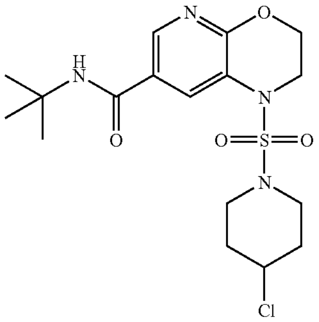 | N-tert-butyl-1-(4-chloropiperidin-1-ylsulfonyl)-2,3-dihydro-1H-pyrido[2,3-b][1,4]oxazine-7-carboxamide | $[M + H]^+ = 417.2$ |
| 185 | 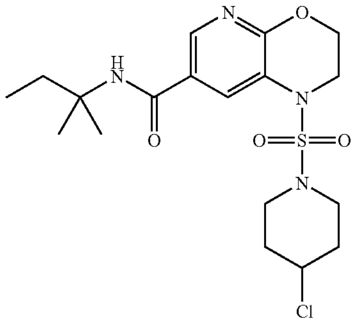 | 1-(4-chloropiperidin-1-ylsulfonyl)-N-tert-pentyl-2,3-dihydro-1H-pyrido[2,3-b][1,4]oxazine-7-carboxamide | $[M + H]^+ = 431.2$ |
| 186 | 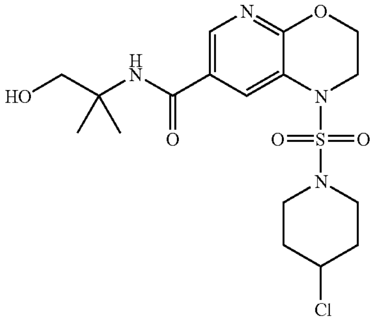 | 1-(4-chloropiperidin-1-ylsulfonyl)-N-(1-hydroxy-2-methylpropan-2-yl)-2,3-dihydro-1H-pyrido[2,3-b][1,4]oxazine-7-carboxamide | $[M + H]^+ = 433.2$ |
| 187 | 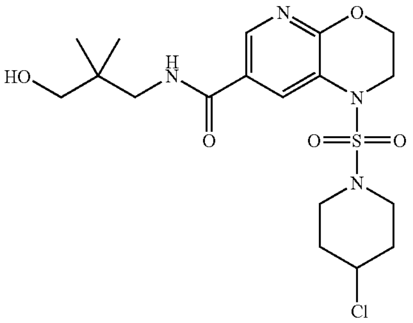 | 1-(4-chloropiperidin-1-ylsulfonyl)-N-(3-hydroxy-2,2-dimethylpropyl)-2,3-dihydro-1H-pyrido[2,3-b][1,4]oxazine-7-carboxamide | $[M + H]^+ = 447.2$ |

TABLE 4-continued

| Example | Compound | Name | LCMS |
|---|---|---|---|
| 188 | 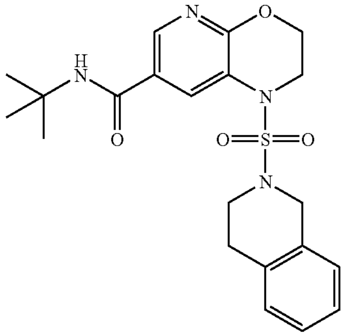 | N-tert-butyl-1-(3,4-dihydroisoquinolin-2(1H)-ylsulfonyl)-2,3-dihydro-1H-pyrido[2,3-b][1,4]oxazine-7-carboxamide | $[M + H]^+ = 431.3$ |
| 189 | 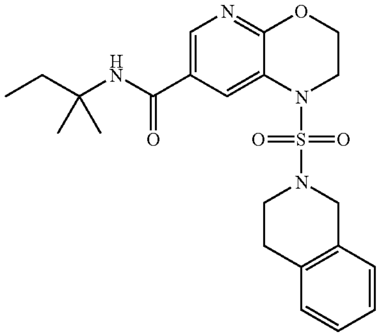 | 1-(3,4-dihydroisoquinolin-2(1H)-ylsulfonyl)-N-tert-pentyl-2,3-dihydro-1H-pyrido[2,3-b][1,4]oxazine-7-carboxamide | $[M + H]^+ = 445.3$ |
| 190 | 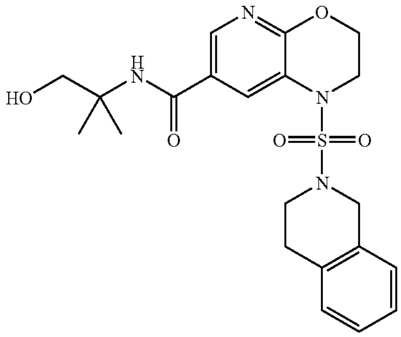 | 1-(3,4-dihydroisoquinolin-2(1H)-ylsulfonyl)-N-(1-hydroxy-2-methylpropan-2-yl)-2,3-dihydro-1H-pyrido[2,3-b][1,4]oxazine-7-carboxamide | $[M + H]^+ = 447.3$ |
| 191 | 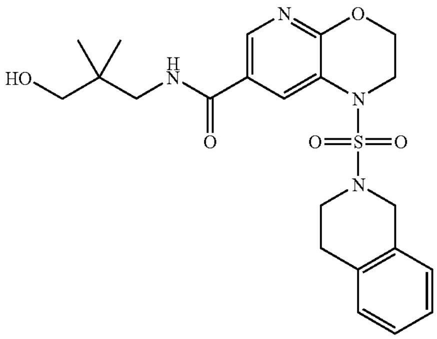 | 1-(3,4-dihydroisoquinolin-2(1H)-ylsulfonyl)-N-(3-hydroxy-2,2-dimethyl propyl)-2,3-dihydro-1H pyrido[2,3-b][1,4]oxazine-7-carboxamide | $[M + H]^+ = 461.3$ |

TABLE 4-continued

| Example | Compound | Name | LCMS |
|---|---|---|---|
| 192 | 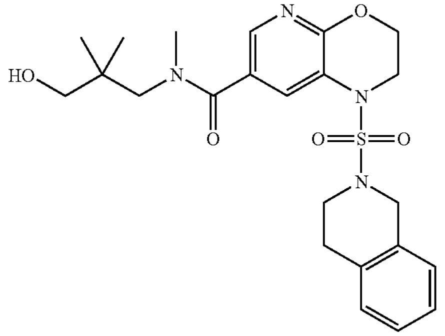 | 1-(3,4-dihydroisoquinolin-2(1H)-ylsulfonyl)-N-(3-hydroxy-2,2-dimethyl-propyl)-N-methyl-2,3-dihydro-1H-pyrido[2,3-b][1,4]oxazine-7-carboxamide | $[M + H]^+ = 475.3$ |
| 193 | 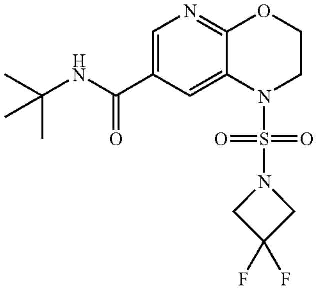 | N-tert-butyl-1-(3,3-difluoroazetidin-1-ylsulfonyl)-2,3-dihydro-1H-pyrido[2,3-b][1,4]oxazine-7-carboxamide | $[M + H]^+ = 391.3$ |
| 194 | 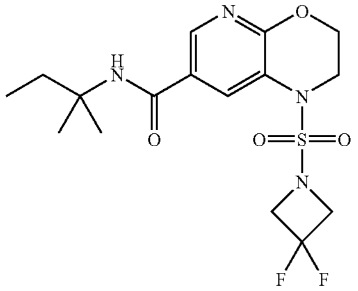 | 1-(3,3-difluoroazetidin-1-ylsulfonyl)-N-tert-pentyl-2,3-dihydro-1H-pyrido[2,3-b][1,4]oxazine-7-carboxamide | $[M + H]^+ = 405.2$ |
| 195 | 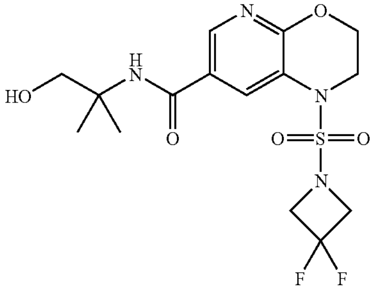 | 1-(3,3-difluoroazetidin-1-ylsulfonyl)-N-(1-hydroxy-2-methylpropan-2-yl)-2,3-dihydro-1H-pyrido[2,3-b][1,4]oxazine-7-carboxamide | $[M + H]^+ = 407.2$ |
| 196 | 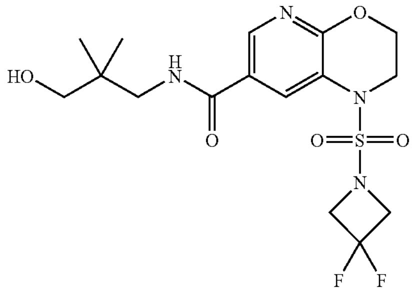 | 1-(3,3-difluoroazetidin-1-ylsulfonyl)-N-(3-hydroxy-2,2-dimethylpropyl)-2,3-dihydro-1H-pyrido[2,3-b][1,4]oxazine-7-carboxamide | $[M + H]^+ = 421.2$ |

TABLE 4-continued

| Example | Compound | Name | LCMS |
|---|---|---|---|
| 197 | 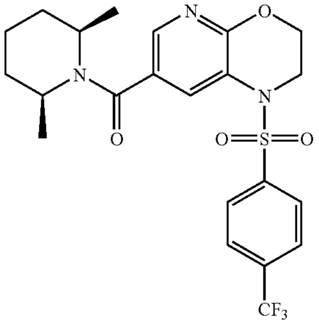 | (cis-2,6-dimethylpiperidin-1-yl)(1-(4-(trifluoromethyl)phenylsulfonyl)-2,3-dihydro-1H-pyrido[2,3-b][1,4]oxazin-7-yl)methanone | $[M + H]^+ = 484.1$ |
| 198 | 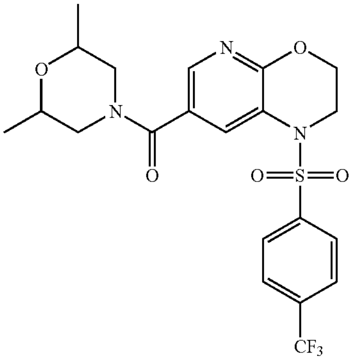 Fast Eluting Isomer (cis or trans) | (2,6-dimethylmorpholino)(1-(4-(trifluoromethyl)phenylsulfonyl)-2,3-dihydro-1H-pyrido[2,3-b][1,4]oxazin-7-yl)methanone | $[M + H]^+ = 486.1$ |
| 199 | 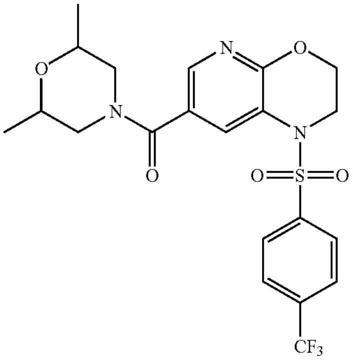 Slow Eluting Isomer (cis or trans) | (2,6-dimethylmorpholino)(1-(4-(trifluoromethyl)phenylsulfonyl)-2,3-dihydro-1H-pyrido[2,3-b][1,4]oxazin-7-yl)methanone | $[M + H]^+ = 486.1$ |
| 200 | 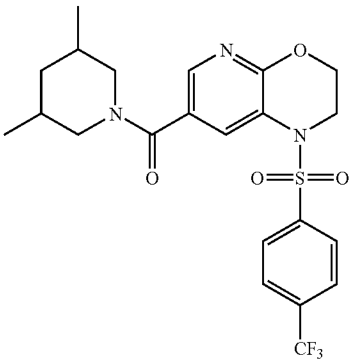 | (3,5-dimethylpiperidin-1-yl)(1-(4-(trifluoromethyl)phenylsulfonyl)-2,3-dihydro-1H-pyrido[2,3-b][1,4]oxazin-7-yl)methanone | $[M + H]^+ = 484.1$ |

TABLE 4-continued

| Example | Compound | Name | LCMS |
|---|---|---|---|
| 201 | 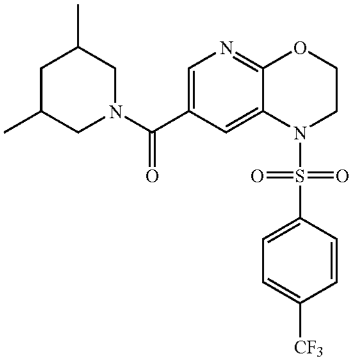 | (3,5-dimethylpiperidin-1-yl)(1-(4-(trifluoromethyl)phenylsulfonyl)-2,3-dihydro-1H-pyrido[2,3-b][1,4]oxazin-7-yl)methanone | $[M+H]^+ = 484.1$ |

The compounds listed in Table 5, Examples 202, 203 and 204 were isolated as byproducts from the preparations described in Examples 72, 120 and 121 respectively.

TABLE 5

| Example | Compound | Name | LCMS |
|---|---|---|---|
| 202 | 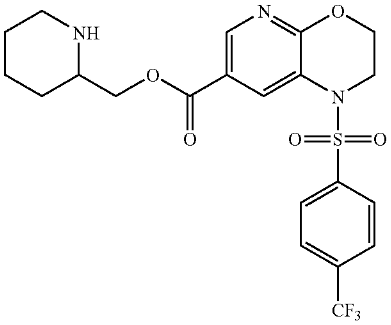 | piperidin-2-ylmethyl 1-(4-(trifluoromethyl)phenylsulfonyl)-2,3-dihydro-1H-pyrido[2,3-b][1,4]oxazine-7-carboxylate | $[M+H]^+ =$ 486.0 |
| 203 | 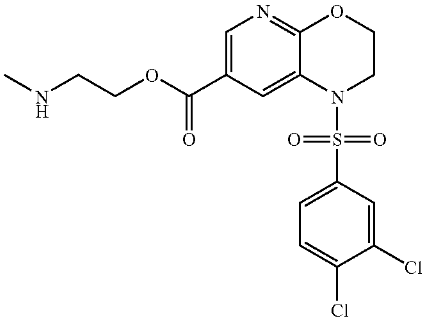 | 2-(methylamino)ethyl 1-(3,4-dichlorophenylsulfonyl)-2,3-dihydro-1H-pyrido[2,3-b][1,4]oxazine-7-carboxylate | $[M+H]^+ =$ 446.0 |
| 204 | 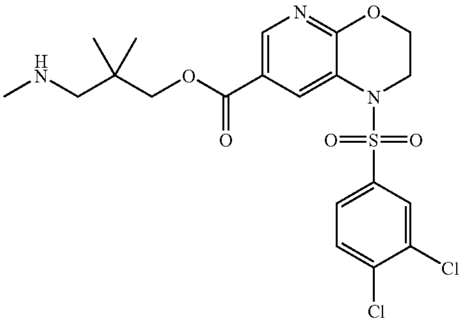 | 2,2-dimethyl-3-(methylamino)propyl 1-(3,4-dichlorophenylsulfonyl)-2,3-dihydro-1H-pyrido[2,3-b][1,4]oxazine-7-carboxylate | $[M+H]^+ =$ 488.1 |

Example 205

Preparation of methyl 4-(1-(3,4-dichlorophenylsulfonyl)-2,3-dihydro-1H-pyrido[2,3-b][1,4]oxazine-7-carboxamido)tetrahydro-2H-pyran-4-carboxylate

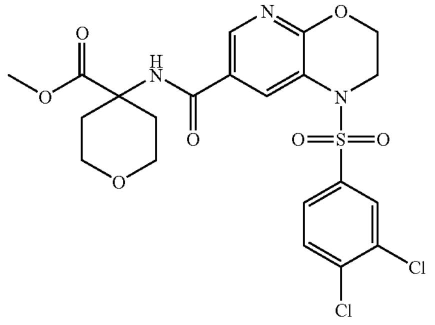

To a suspension of 4-amino-tetrahydro-pyran-4-carboxylic acid hydrochloride (53.5 mg, 0.294 mmol) in $Et_2O$ (1 mL) was added TMS-diazomethane (0.392 mL, 0.785 mmol) and water (200 μL). Upon addition of water, a vigorous evolution of gas occurred. The reaction was allowed to stir for 10 min at which time the reaction turned clear. The excess TMS-diazomethane was quenched by addition of AcOH until the solution turned colorless. The reaction mixture was concentrated in vacuo to provide an aqueous solution. The aqueous solution was added to a biphasic mixture of 1-(3,4-dichloro-phenylsulfonyl)-2,3-dihydro-1H-pyrido[2,3-b][1,4]oxazine-7-carbonyl chloride (80 mg, 0.196 mmol, prepared from Intermediate O by analogy with Example 1) in DCM (4 mL) and saturated aqueous $NaHCO_3$ (4 mL). The reaction was allowed to stir for 16 h. The biphasic mixture was extracted with DCM (3×5 mL). The combined organics were dried over $Na_2SO_4$ and concentrated in vacuo. The resulting solid was purified by flash column chromatography using a gradient elution of hexanes with 10-70% EtOAc to provide methyl 4-(1-(3,4-dichlorophenylsulfonyl)-2,3-dihydro-1H-pyrido[2,3-b][1,4]oxazine-7-carboxamido)tetrahydro-2H-pyran-4-carboxylate (36.5 mg, 0.065 mmol, 33.3% yield) as a white solid. LCMS (+ESI) m/z=530.0 $[M+H]^+$; $^1H$-NMR ($CDCl_3$) δ 8.53 (s, 1H), 8.50 (br s, 1H), 7.83, (d, 1H), 7.59 (d, 1H), 7.49 (dd, 1H), 6.34 (br s, 1H), 4.10 (m, 2H), 3.89 (m, 4H), 3.80 (s, 3H), 3.75 (m, 2H), 2.35 (m, 2H), 2.10 (m, 1H), 2.07 (m 1H).

Example 206

Preparation of 1-(1-(4-(trifluoromethyl)phenylsulfonyl)-2,3-dihydro-1H-pyrido[2,3-b][1,4]oxazine-7-carboxamido)cyclopropanecarboxylic acid

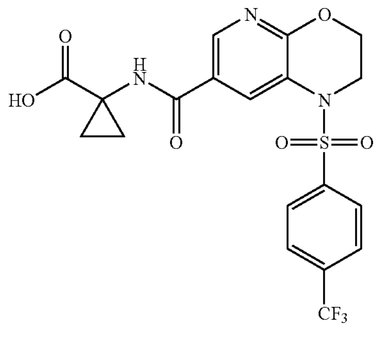

To a suspension of the compound produced in Example 70 (37.0 mg, 0.074 mmol) MeOH (1 mL) and water (1 mL) was added lithium hydroxide (17.72 mg, 0.740 mmol). The reaction was stirred at room temperature for 16 h. The reaction mixture was concentrated in vacuo. The acid was purified by HPLC to provide 1-(1-(4-(trifluoro-methyl)phenylsulfonyl)-2,3-dihydro-1H-pyrido[2,3-b][1,4]oxazine-7-carboxamido)cyclopropanecarboxylic acid (5.4 mg, 0.011 mmol, 15.5% yield). LCMS (+ESI) m/z=472.0 $[M+H]^+$.

Example 207

Preparation of 2-(1-(1-(4-(trifluoromethyl)phenylsulfonyl)-2,3-dihydro-1H-pyrido[2,3-b][1,4]oxazine-7-carbonyl)piperidin-2-yl)acetic acid

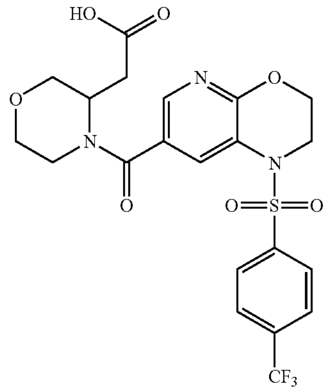

The title compound was prepare using the procedure outlined in Example 206 with substitution of the compound of Example 73 for the compound of Example 70 LCMS (+ESI) m/z=516.0 $[M+H]^+$.

Example 208

Preparation of 1-(1-(4-(trifluoromethyl)phenylsulfonyl)-2,3-dihydro-1H-pyrido[2,3-b][1,4]oxazine-7-carboxamido)cyclobutanecarboxylic acid

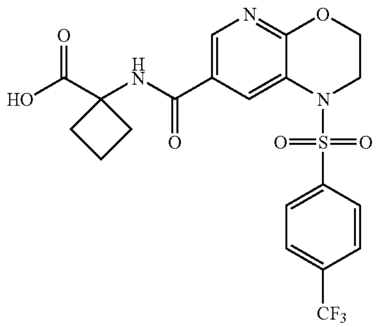

The title compound was prepare using the procedure outlined in Example 206 with substitution of the compound of Example 71 for the compound of Example 70 LCMS (+ESI) m/z=486.0 $[M+H]^+$.

Example 209

Preparation of 1-(3,4-dichlorophenylsulfonyl)-N-(1-(hydroxymethyl)cyclobutyl)-2,3-dihydro-1H-pyrido[2,3-b][1,4]oxazine-7-carboxamide

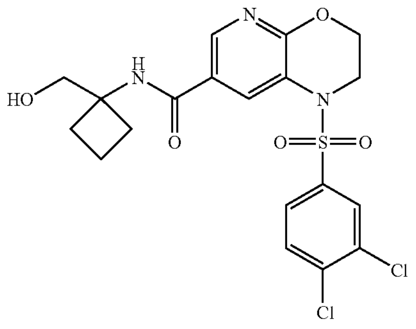

To a solution of the compound of Example 139 (25 mg, 0.049 mmol) in THF (2 mL) at 0° C. was added DIBAL-H (0.146 mL, 0.146 mmol). The reaction was allowed to warm to room temperature over 1 h and then stirred at room temperature for 2 h. LCMS analysis of the reaction mixture identified the starting material as the major component with only a minor amount of the alcohol present. The reaction was cooled to 0° C. and additional DIBAL-H (0.438 mL, 0.438 mmol) was added. The reaction was again warmed to room temperature and stirred for 16 h. The reaction was quenched with 1 N HCl and the biphasic mixture was extracted with EtOAc (3×5 mL). The combined organics were dried over $Na_2SO_4$ and concentrated in vacuo. The resulting solid was purified by flash column chromatography using a gradient elution of hexanes with 20-90% EtOAc to provide 1-(3,4-dichlorophenylsulfonyl)-N-(1-(hydroxymethyl)cyclobutyl)-2,3-dihydro-1H-pyrido[2,3-b][1,4]oxazine-7-carboxamide (6.6 mg, 0.013 mmol, 27.3% yield) as a white solid. LCMS (+ESI) m/z=472.1 $[M+H]^+$.

Example 210

Preparation of 7-(3-ethyl-1,2,4-oxadiazol-5-yl)-1-(phenylsulfonyl)-2,3-dihydro-1H-pyrido[2,3-b][1,4]oxazine

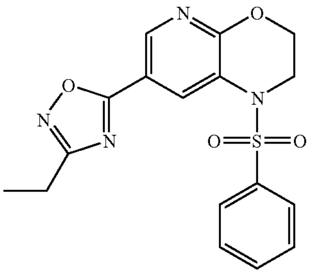

To a solution of 1-(phenylsulfonyl)-2,3-dihydro-1H-pyrido[2,3-b][1,4]oxazine-7-carbonyl chloride (40 mg, 0.118 mmol; Example 1, Step 1) in DCM (2 mL) was added N-hydroxypropionimidamide (20.81 mg, 0.236 mmol) and DIPEA (50 μL, 0.286 mmol). The reaction was stirred at room temperature for 16 hours. LCMS analysis of the reaction mixture indicated consumption of starting material. The reaction mixture was treated with saturated aqueous $NaHCO_3$ (10 mL) and extracted with EtOAc (3×10 mL). The combined organics were dried over anhydrous $Na_2SO_4$ and concentrated in vacuo. The resulting solid was diluted with THF (5 mL) and TBAF in THF (118 μL, 0.118 mmol) was added. The reaction was then stirred overnight. The reaction mixture was concentrated in vacuo and the resulting paste was purified by flash column chromatography using a gradient elution of hexanes with 30-100% EtOAc to provide 7-(3-ethyl-1,2,4-oxadiazol-5-yl)-1-(phenylsulfonyl)-2,3-dihydro-1H-pyrido[2,3-b][1,4]oxazine (29.7 mg, 0.076 mmol, 64.2% yield) as a white solid. LCMS (+ESI) m/z=373.0 $[M+H]^+$; $^1$H-NMR ($CDCl_3$) δ 8.87 (d, 1H), 8.77 (d, 1H), 7.71 (m, 2H), 7.63 (tt, 1H) 7.51 (m, 2H), 4.01 (m, 2H), 3.92 (m, 2H), 2.84 (q, 2H), 1.39 (t, 3H).

Example 211

Preparation of 7-(5-phenyl-1,3,4-oxadiazol-2-yl)-1-(phenylsulfonyl)-2,3-dihydro-1H-pyrido[2,3-b][1,4]oxazine

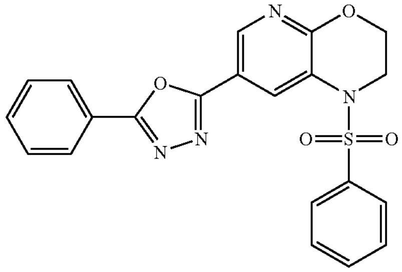

To a solution of 1-(phenylsulfonyl)-2,3-dihydro-1H-pyrido[2,3-b][1,4]oxazine-7-carbonyl chloride (40 mg, 0.118 mmol; Example 1 Step 1) in DCM (1.5 mL) was added benzohydrazide (32.2 mg, 0.236 mmol) and DIPEA (50 μL, 0.286 mmol). The reaction was stirred at room temperature for 16 hours. TLC analysis of the reaction mixture indicated consumption of starting material. The reaction was quenched with saturated aqueous $NaHCO_3$ (2 mL) and was extracted with DCM (3×2 mL). The combined organics were dried over anhydrous $Na_2SO_4$ and concentrated in vacuo. The resulting solid was dissolved in DMF (3 mL) and treated with Burgess reagent (28.1 mg, 0.118 mmol). The reaction mixture was heated to 180° C. by heating under microwave irradiation for 5 minutes. The mixture was concentrated in vacuo. The resulting paste was purified by flash column chromatography using a gradient elution of hexanes with 10-90% EtOAc. The resulting tan solid was triturated with water (2×10 mL) to provide 7-(5-phenyl-1,3,4-oxadiazol-2-yl)-1-(phenylsulfonyl)-2,3-dihydro-1H-pyrido[2,3-b][1,4]oxazine (4.6 mg, 10.39 μmol, 8.80% yield) as a white solid. LCMS (+ESI) m/z=421.0 $[M+H]^+$; $^1$H-NMR ($CDCl_3$) δ 8.90 (d, 1H), 8.84 (d, 1H), 8.17 (m, 2H), 7.74 (m, 2H), 7.65 (tt, 1H), 7.59-7.51 (m, 5H), 4.02 (m, 2H), 3.95 (m, 2H).

Example 212

Preparation of 7-(5-tert-butyl-1,3,4-oxadiazol-2-yl)-1-(4-fluorophenylsulfonyl)-2,3-dihydro-1H-pyrido[2,3-b][1,4]oxazine

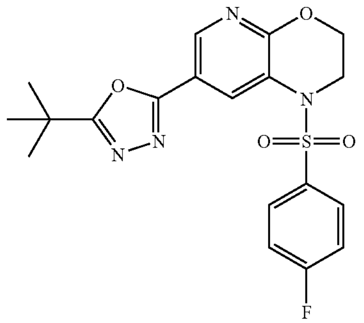

The compound of Example 212 was prepared using the procedure described for the synthesis of the compound of Example 211 with substitution of intermediate D for intermediate C in Example 1 step 1 and substitution of pivalohydrazide for benzohydrazide in Example 211. LCMS (+ESI) m/z=419.0 $[M+H]^+$.

Example 213

Preparation of N-cyclopentyl-5-(1-(4-fluorophenylsulfonyl)-2,3-dihydro-1H-pyrido[2,3-b][1,4]oxazin-7-yl)-1,2,4-oxadiazole-3-carboxamide

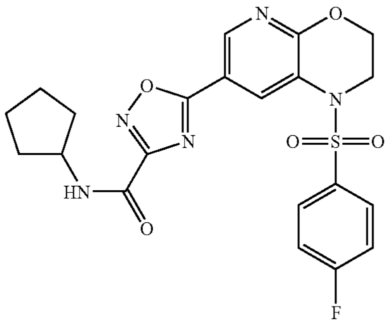

Step 1: Preparation of ethyl 5-(1-(4-fluorophenylsulfonyl)-2,3-dihydro-1H-pyrido[2,3-b][1,4]oxazin-7-yl)-1,2,4-oxadiazole-3-carboxylate

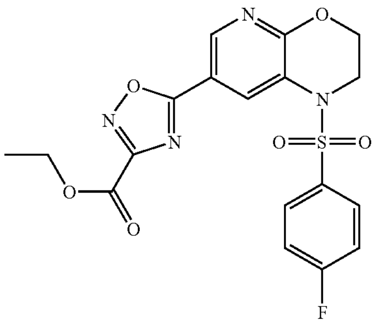

To a solution of 1-(4-fluorophenylsulfonyl)-2,3-dihydro-1H-pyrido[2,3-b][1,4]oxazine-7-carbonyl chloride (200 mg, 0.561 mmol) in DCM (5 mL) and water (1 mL) was added ethyl 2-(hydroxyamino)-2-iminoacetate (143.5 mg, 1.086 mmol) and DIPEA (230 μL, 1.317 mmol) to give a pink suspension. The reaction was stirred at 40° C. for 1.5 hours. LCMS analysis of the reaction mixture indicated complete consumption of starting material. The reaction mixture was extracted with DCM (2×10 mL) dried over anhydrous $Na_2SO_4$ and concentrated in vacuo. The resulting solid was dissolved in THF (6 mL) and treated with TBAF (0.561 mL, 0.561 mmol). The resulting yellow solution was stirred overnight. LCMS analysis of the reaction indicated consumption of the intermediate. The solvent was removed under reduced pressure. The resulting paste was purified by flash column chromatography using a gradient elution of hexanes with 30-100% EtOAc. Ethyl 5-(1-(4-fluorophenylsulfonyl)-2,3-dihydro-1H-pyrido[2,3-b][1,4]oxazin-7-yl)-1,2,4-oxadiazole-3-carboxylate (120 mg, 0.276 mmol, 49.2%) was isolated as an off-white solid. LCMS (+ESI) m/z=435.0 $[M+H]^+$.

Step 2 Preparation of 5-(1-(4-fluorophenylsulfonyl)-2,3-dihydro-1H-pyrido[2,3-b][1,4]oxazin-7-yl)-1,2,4-oxadiazole-3-carbonyl chloride

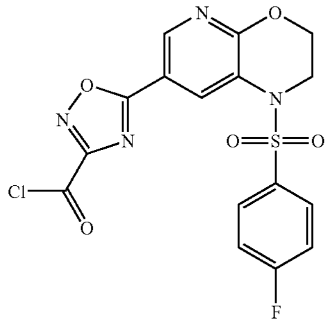

To a solution of ethyl 5-(1-(4-fluorophenylsulfonyl)-2,3-dihydro-1H-pyrido[2,3-b][1,4]oxazin-7-yl)-1,2,4-oxadiazole-3-carboxylate (120 mg, 0.276 mmol) in MeOH (5 mL) and water (2.5 mL) was added lithium hydroxide (119.2 mg, 4.98 mmol). The reaction was allowed to stir over night. LCMS analysis of the reaction mixture indicated consumption of starting material. The organic solvent was removed under reduced pressure and the remaining aqueous mixture was acidified with 1N HCl until a precipitate formed. The precipitate was extracted from the aqueous layer with EtOAc (2×20 mL). The combined organics were dried over anhydrous $Na_2SO_4$ and concentrated in vacuo.

The resulting solid was dissolved in DCE (5 mL) and treated with thionyl chloride (0.180 mL, 2.471 mmol). The white suspension was stirred at 70° C. for 2 hours and then at 80° C. and for an additional 5 hours. LCMS analysis of the reaction mixture indicated consumption of the acid. The reaction mixture was concentrated in vacuo to provide 5-(1-(4-fluorophenylsulfonyl)-2,3-dihydro-1H-pyrido[2,3-b][1,4]oxazin-7-yl)-1,2,4-oxadiazole-3-carboxylic acid (105 mg, 0.247 mmol, 89% yield) as an off-white solid, which was used without further purification. LCMS (methanol adduct i.e. the methyl ester; +ESI) m/z=421.0 $[M+H]^+$.

Step 3 Preparation of N-cyclopentyl-5-(1-(4-fluorophenylsulfonyl)-2,3-dihydro-1H-pyrido[2,3-b][1,4]oxazin-7-yl)-1,2,4-oxadiazole-3-carboxamide To a suspension of 5-(1-(4-fluorophenylsulfonyl)-2,3-dihydro-1H-pyrido[2,3-b][1,4]oxazin-7-yl)-1,2,4-oxadiazole- 3-carbonyl chloride (21 mg, 0.049 mmol) in DCE (5 mL) was added DIPEA (21 μL, 120 μmol) to form a clear solution. To that solution was added cyclopentyl amine (40 μL, 0.099 mmol) and saturated aqueous $NaHCO_3$ (1 mL). The reaction was stirred for 72 hours. LCMS analysis of the reaction mixture indicated consumption of starting material. The reaction was extracted with DCM (3×2 mL). The combined organics were dried over anhydrous $Na_2SO_4$ and concentrated in vacuo. The resulting solid was purified by flash column chromatography to provide N-cyclopentyl-5-(1-(4-fluorophenylsulfonyl)-2,3-dihydro-1H-pyrido[2,3-b][1,4]oxazin-7-yl)-1,2,4-oxadiazole-3-carboxamide (7.7 mg, 0.016 mmol, 32.2%) as a white solid. LCMS (+ESI) m/z=474.1 $[M+H]^+$; $^1$H-NMR ($CDCl_3$) δ 8.90 (d, 1H), 8.87 (d, 1H), 7.75 (m, 2H), 7.21 (m, 2H), 6.97 (m, 1H), 4.47 (m, 1H), 4.09 (dd, 2H), 3.92 (dd, 2H), 2.13 (m, 2H), 1.82-1.52 (m, 6H).

The compounds listed in Table 6 were prepared using the procedure described in the synthesis of the compound of Example 213 above, with substitution of an amine in step 3. For instance, the compounds of Examples 214, 215, and 216 were prepared by substituting tert-butyl amine, morpholine and 3-methoxypropan-1-ylamine respectively for cyclopentyl amine in step 3 described in Example 213.

TABLE 6

| Example | Compound | Name | MS |
|---|---|---|---|
| 214 | 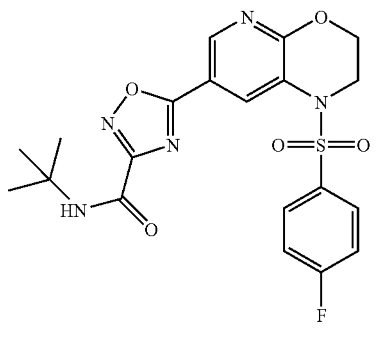 | N-tert-butyl-5-(1-(4-fluorophenyl sulfonyl)-2,3-dihydro-1H-pyrido[2,3-b][1,4]oxazin-7-yl)-1,2,4-oxadiazole-3-carboxamide | $[M + H]^+ = 462.2$ |
| 215 | 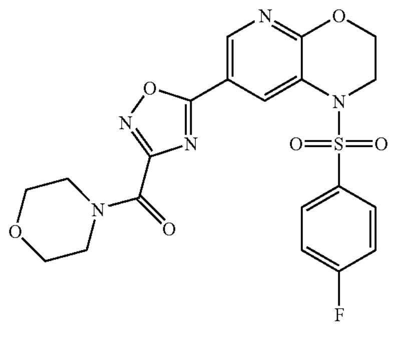 | (5-(1-(4-fluorophenylsulfonyl)-2,3-dihydro-1H-pyrido[2,3-b][1,4]oxazin-7-yl)-1,2,4-oxadiazol-3-yl)(morpholino)methanone | $[M + H]^+ = 476.0$ |
| 216 | 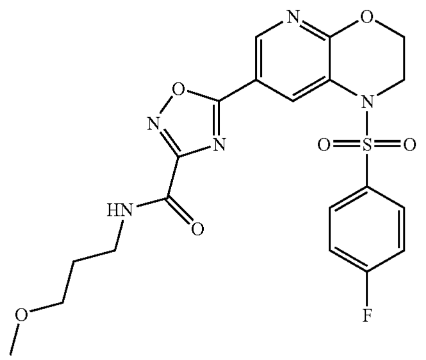 | 5-(1-(4-fluorophenylsulfonyl)-2,3-dihydro-1H-pyrido[2,3-b][1,4]oxazin-7-yl)-N-(3-methoxypropyl)-1,2,4-oxadiazole-3-carboxamide | $[M + H]^+ = 478.1$ |

Example 217

Preparation of 7-(oxazolo[4,5-b]pyridin-2-yl)-1-(phenylsulfonyl)-2,3-dihydro-1H-pyrido[2,3-b][1,4] oxazine

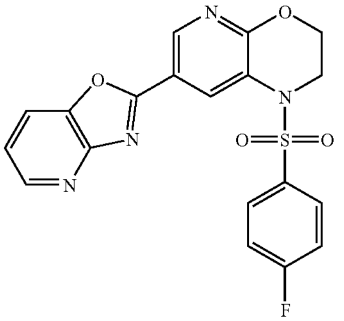

1-(4-fluorophenylsulfonyl)-2,3-dihydro-1H-pyrido[2,3-b][1,4]oxazine-7-carbonyl chloride (25 mg, 70 μmol) was dissolved in THF (0.5 mL) and placed in a 2 mL microwave vial. To this solution was added 2-aminopyridin-3-ol (8.5 mg, 77 μmol), DIPEA (26 μL, 150 μmol) and a magnetic stirrer bar and the reaction was capped. After stirring at room temperature for 1 hour, conversion to the amide was complete as shown by LCMS. To the crude reaction mixture was added Burgess reagent (83 mg, 350 μmol) and the reaction was heated for 5 minutes at 150° C. on a Biotage Initiator. The reaction mixture was diluted with DCM (3 mL) and saturated aqueous sodium bicarbonate (3 mL). The organic layer was removed and the aqueous layer extracted with DCM (2 mL). The organic layers were combined, dried with sodium sulfate, filtered and evaporated to produce a brown oil that was purified by flash column chromatography on an ISCO HPLC using a 4 gram $SiO_2$ cartridge and a gradient of 25-100% hexanes in EtOAc. This yielded 15 mg (52%) of a yellow oil. LCMS (+ESI) m/z=413.0 $[M+H]^+$; $^1$H-NMR ($CDCl_3$) δ 9.05 (dd, 2H), 8.60 (d, 1H), 7.95 (dd, 1H), 7.82 (d, 1H), 7.78 (d, 1H), 7.35 (dd, 1H), 7.20 (dd, 2H), 4.12 (t, 2H), 3.96 (t, 2H).

Example 218

Preparation of N-tert-butyl-1-(4-fluorobenzyl)-2-oxo-2,3-dihydro-1H-pyrido[2,3-b][1,4]oxazine-7-carboxamide

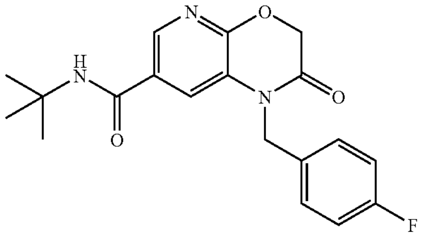

1-(4-fluorobenzyl)-2-oxo-2,3-dihydro-1H-pyrido[2,3-b][1,4]oxazine-7-carboxylic acid (36 mg, 120 μmol) was suspended in DCE (2 mL) in a 20 mL screw-capped vial. To this suspension were added thionyl chloride (88 μL, 1.2 mmol) and a few drops of DMF. Upon addition of the DMF, a gas evolved and the reaction mixture turned a deep yellow. The reaction was capped and shaken for one hour at 80° C. The volatiles were evaporated on a rotary evaporator. The brown, oily residue was used without further purification.

The brown oil was dissolved in DCM (2 mL) in a 20 mL screw-capped vial. To this solution was added 2 mL of saturated aqueous sodium bicarbonate, tert-butylamine (44 mg, 600 μmol) and a stirbar. The reaction mixture fumed slightly upon the addition of the amine and turned a light yellow. The reaction was stirred overnight. The organic layer was transferred to a fresh vial. The aqueous layer was extracted with DCM (2 mL). The organic layers were combined, dried over anhydrous $Na_2SO_4$, filtered and evaporated. The resulting a yellow oil was purified by normal phase flash column chromatography a gradient of 25-100% hexanes in EtOAc to provide 15 mg (36%) the desired product as a white solid. LCMS (+ESI) m/z=358.1 $[M+H]^+$; $^1$H-NMR ($CDCl_3$) δ 8.12 (d, 1H), 7.75 (d, 1H), 7.30 (t, 2H), 7.05 (t, 2H), 5.85 (s, 1H), 5.15 (s, 2H), 5.00 (s, 2H), 1.45 (s, 9H).

The compounds listed in Table 7 were prepared using the procedure described in Example 218. These compounds were prepared using an intermediate chosen from intermediates AS to AU and treating the intermediate under the above-described conditions, with a primary or secondary amine in Step 2. For instance, the compounds of Examples 219 and 220 were prepared by substituting Intermediate AT for Intermediate AS and treating the resulting acid chloride with cyclopentyl amine and tert-butyl amine, respectively.

TABLE 7

| Example | Compound | Name | MS |
|---|---|---|---|
| 219 | 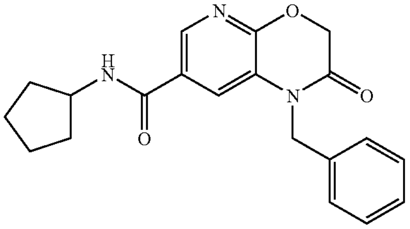 | 1-benzyl-N-cyclopentyl-2-oxo-2,3-dihydro-1H-pyrido[2,3-b][1,4]oxazine-7-carboxamide | $[M + H]^+ = 352.1$ |

TABLE 7-continued

| Example | Compound | Name | MS |
|---|---|---|---|
| 220 | 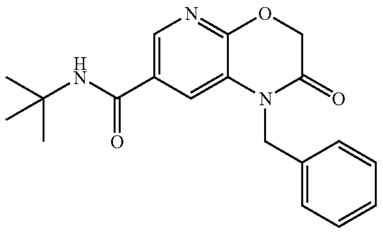 | 1-benzyl-N-tert-butyl-2-oxo-2,3-dihydro-1H-pyrido[2,3-b][1,4]oxazine-7-carboxamide | $[M + H]^+ = 340.1$ |
| 221 | 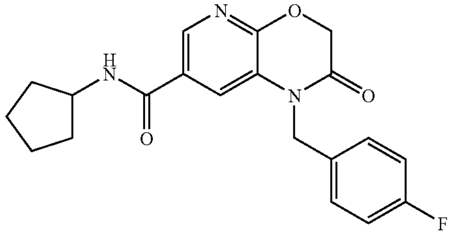 | N-cyclopentyl-1-(4-fluorobenzyl)-2-oxo-2,3-dihydro-1H-pyrido[2,3-b][1,4]oxazine-7-carboxamide | $[M + H]^+ = 370.1$ |
| 222 | 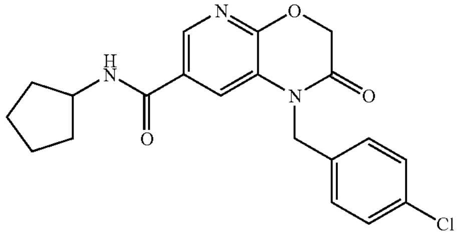 | 1-(4-chlorobenzyl)-N-cyclopentyl-2-oxo-2,3-dihydro-1H-pyrido[2,3-b][1,4]oxazine-7-carboxamide | $[M + H]^+ = 386.1$ |

Example 223

Preparation of 7-(5,5-dimethyl-2,5-dihydro-1,2,4-oxadiazol-3-yl)-1-(4-(trifluoromethyl)phenylsulfonyl)-2,3-dihydro-1H-pyrido[2,3-b][1,4]oxazine

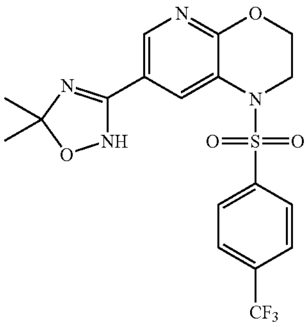

Step 1: Preparation of 1-(4-(trifluoromethyl)phenylsulfonyl)-2,3-dihydro-1H-pyrido[2,3-b][1,4]oxazine-7-carboxamide

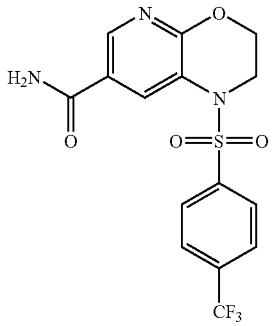

A solution of methyl 1-(4-(trifluoromethyl)phenylsulfonyl)-2,3-dihydro-1H-pyrido[2,3-b][1,4]oxazine-7-carboxylate (500 mg, 1.243 mmol) in 7 M $NH_3$ in MeOH (10 mL) was heated to 60° C. and stirred at that temperature for 72 h. The solvent was removed under reduced pressure to provide 1-(4-

(trifluoromethyl)phenylsulfonyl)-2,3-dihydro-1H-pyrido[2,3-b][1,4]oxazine-7-carboxamide (481 mg, 1.243 mmol, 100% yield) as a white solid. LCMS (+ESI) m/z=388.1 $[M+H]^+$.

Step 2: Preparation of 1-(4-(trifluoromethyl)phenylsulfonyl)-2,3-dihydro-1H-pyrido[2,3-b][1,4]oxazine-7-carbonitrile

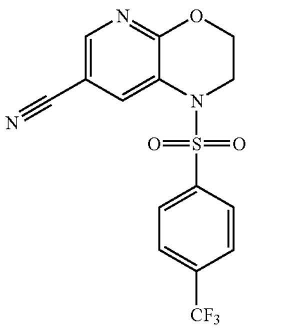

To a solution of 1-(4-(trifluoromethyl)phenylsulfonyl)-2,3-dihydro-1H-pyrido[2,3-b][1,4]oxazine-7-carboxamide (481 mg, 1.243 mmol) in toluene (10 mL) was added phosphorous oxychloride (0.579 mL, 6.22 mmol). The reaction was heated to 80° C. and stirred at that temperature for 6 h. The reaction mixture was poured over ice water (30 mL) and allowed to stir for 30 min. The biphasic mixture was treated with saturated aqueous $NaHCO_3$ and extracted with EtOAc (3×50 mL). The combined organics were dried over anhydrous $Na_2SO_4$ and concentrated in vacuo to provide 1-(4-(trifluoro-ethyl)phenylsulfonyl)-2,3-dihydro-1H-pyrido[2,3-b][1,4]oxazine-7-carbonitrile (450 mg, 1.218 mmol, 98% yield) as a white solid. LCMS (+ESI) m/z=370.0 $[M+H]^+$.

Step 3: Preparation of N-hydroxy-1-(4-(trifluoromethyl)phenylsulfonyl)-2,3-dihydro-1H-pyrido[2,3-b][1,4]oxazine-7-carboximidamide

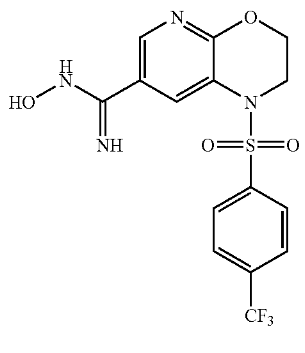

To a suspension of 1-(4-(trifluoromethyl)phenylsulfonyl)-2,3-dihydro-1H-pyrido[2,3-b][1,4]oxazine-7-carbonitrile (75 mg, 0.203 mmol) in ethanol (2 mL) and water (0.5 mL) was added hydroxylamine hydrochloride (42.3 mg, 0.609 mmol) and sodium carbonate (108 mg, 1.015 mmol). The reaction was heated to 80° C. and stirred at that temperature for 16 h. The reaction mixture was concentrated in vacuo. The resulting paste was suspended in water (10 mL) and extracted with EtOAc (2×20 mL). The combined organics were dried over anhydrous $Na_2SO_4$ and concentrated in vacuo to provide N-hydroxy-1-(4-(trifluoromethyl)phenylsulfonyl)-2,3-dihydro-1H-pyrido[2,3-b][1,4]oxazine-7-carboximidamide (80 mg, 0.199 mmol, 98% yield) as a white solid, which was used without further purification. LCMS (+ESI) m/z=403.1 $[M+H]^+$.

Step 4: Preparation of 7-(5,5-dimethyl-2,5-dihydro-1,2,4-oxadiazol-3-yl)-1-(4-(trifluoromethyl)phenylsulfonyl)-2,3-dihydro-1H-pyrido[2,3-b][1,4]oxazine To a solution of N-hydroxy-1-(4-(trifluoromethyl)phenylsulfonyl)-2,3-dihydro-1H-pyrido[2,3-b][1,4]oxazine-7-carboximidamide (25 mg, 0.062 mmol) in acetone (2 mL) was added acetic acid (500 μL, 8.73 mmol). The reaction was heated to 80° C. and stirred at that temperature for 48 h. The reaction mixture was concentrated under reduced pressure. The resulting paste was purified by flash column chromatography using a gradient elution of hexanes with 20-100% EtOAc to provide 7-(5,5-dimethyl-2,5-dihydro-1,2,4-oxadiazol-3-yl)-1-(4-(trifluoromethyl)phenylsulfonyl)-2,3-dihydro-1H-pyrido[2,3-b][1,4]oxazine (12.3 mg, 0.028 mmol, 44.7% yield) as a white solid. LCMS (+ESI) m/z=443.1 $[M+H]^+$; $^1H$-NMR ($CDCl_3$) δ 8.45 (d, 1H), 8.38 (br s, 1H), 7.84 (d, 2H), 7.78 (d, 2H), 4.55 (br s, 1H), 4.02 (dd, 2H), 3.91 (dd, 2H), 1.63 (s, 6H).

Example 224

Preparation of 7-(4,4-dimethyl-4,5-dihydro-1H-imidazol-2-yl)-1-(4-(trifluoromethyl)phenylsulfonyl)-2,3-dihydro-1H-pyrido[2,3-b][1,4]oxazine

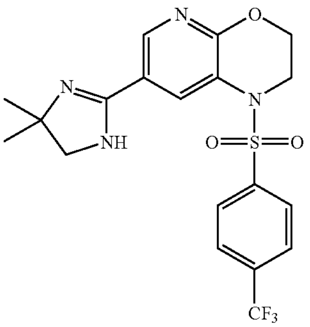

To a suspension of 1-(4-(trifluoromethyl)phenylsulfonyl)-2,3-dihydro-1H-pyrido[2,3-b][1,4]oxazine-7-carbonitrile (30 mg, 0.081 mmol) in toluene (2 mL) was added 1,2-diamino-2-methylpropane (200 μL, 1.908 mmol) and sulfur (20.84 mg, 0.081 mmol). The reaction was heated to 95° C. and stirred at that temperature for 2 h. The reaction mixture was load directly onto a silica gel column and was purified by flash column chromatography using a gradient elution of hexanes with 20-100% EtOAc to provide 7-(4,4-dimethyl-4,5-dihydro-1H-imidazol-2-yl)-1-(4-(trifluoromethyl)phenylsulfonyl)-2,3-dihydro-1H-pyrido[2,3-b][1,4]oxazine (12 mg, 0.026 mmol, 31.9% yield) as an off white solid. LCMS (+ESI) m/z=441.1 $[M+H]^+$; $^1H$-NMR ($CDCl_3$) δ 8.54 (d, 1H), 8.50 (d, 1H), 7.81 (d, 2H), 7.76 (d, 2H), 3.94 (dd, 2H), 3.87 (dd, 2H), 3.57 (br s, 2H), 1.37 (s, 6H).

Example 225

Preparation of 7-(5,5-dimethyl-1,4,5,6-tetrahydropyrimidin-2-yl)-1-(4-(trifluoromethyl)phenylsulfonyl)-2,3-dihydro-1H-pyrido[2,3-b][1,4]oxazine

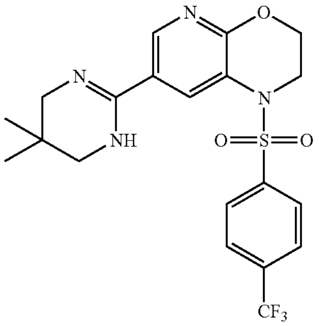

To a solution of 1-(4-(trifluoromethyl)phenylsulfonyl)-2,3-dihydro-1H-pyrido[2,3-b][1,4]oxazine-7-carbonitrile (30 mg, 0.081 mmol) in EtOH (2 mL) was added 2,2-dimethylpropane-1,3-diamine (41.5 mg, 0.406 mmol) and sulfur (41.7 mg, 0.162 mmol). The reaction was heated to 80° C. and stirred at that temperature for 6 h. LCMS analysis identified the product as the predominant component of the reaction mixture. The reaction mixture was concentrated in vacuo and the resulting paste was purified by flash column chromatography using a gradient elution of hexanes with 20-100% EtOAc to provide 7-(5,5-dimethyl-1,4,5,6-tetrahydropyrimidin-2-yl)-1-(4-(trifluoromethyl)phenylsulfonyl)-2,3-dihydro-1H-pyrido[2,3-b][1,4]oxazine (18.7 mg, 0.039 mmol, 48.1% yield) as an off white solid. LCMS (+ESI) m/z=455.1 $[M+H]^+$; $^1$H-NMR ($CD_3OD$) δ 8.51 (d, 1H), 8.26 (d, 1H), 8.01 (d, 2H), 7.90 (d, 2H), 3.98 (s, 4H), 3.15 (s, 4H), 1.05 (s, 6H).

Example 226

Preparation of 7-(5-phenyl-1H-imidazol-2-yl)-1-(4-(trifluoromethyl)phenylsulfonyl)-2,3-dihydro-1H-pyrido[2,3-b][1,4]oxazine

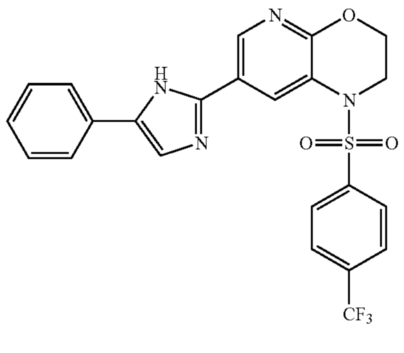

Step 1: Preparation of N-(2-oxo-2-phenylethyl)-1-(4-(trifluoromethyl)phenylsulfonyl)-2,3-dihydro-1H-pyrido[2,3-b][1,4]oxazine-7-carboxamide

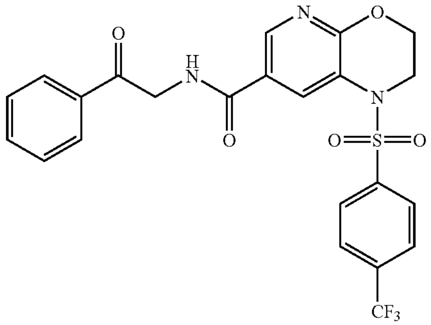

To a solution of 1-(4-(trifluoromethyl)phenylsulfonyl)-2,3-dihydro-1H-pyrido[2,3-b][1,4]oxazine-7-carbonyl chloride (100 mg, 0.246 mmol), in THF (5 mL) was added 2-amino-1-phenylethanone (34.9 mg, 0.258 mmol), and DIPEA (0.086 mL, 0.492 mmol). The reaction was stirred for 2 hours at room temperature. The reaction mixture was diluted with EtOAc (10 mL) and washed with saturated aqueous $NaHCO_3$ (5 mL). The aqueous layer was back extracted with EtOAc (2×5 mL). Combined the organic layers were dried over $Na_2SO_4$, filtered and concentrated in vacuo to provide N-(2-oxo-2-phenylethyl)-1-(4-(trifluoromethyl)phenylsulfonyl)-2,3-dihydro-1H-pyrido[2,3-b][1,4]oxazine-7-carboxamide (115 mg, 0.246 mmol, 93%) as a light brown oil. The material was used without further purification. LCMS (+ESI) m/z=506.1 $[M+H]^+$.

Step 2; Preparation of 7-(5-phenyl-1H-imidazol-2-yl)-1-(4-(trifluoromethyl)phenyl-sulfonyl-2,3-dihydro-1H-pyrido[2,3-b][1,4]oxazines To a solution of N-(2-oxo-2-phenylethyl)-1-(4-(trifluoromethyl)phenylsulfonyl)-2,3-dihydro-1H-pyrido[2,3-b][1,4]oxazine-7-carboxamide (40 mg, 0.079 mmol) in DMF (1 mL) was added ammonium acetate (61 mg, 0.791 mmol). The reaction was subjected to microwave irradiation (150° C., 30 min). The reaction mixture was treated with saturated aqueous $NaHCO_3$ (1 mL) and extracted with EtOAc (2×1 mL). The combined organic layers were dried with sodium sulfate, filtered and evaporated. The residue was purified by flash column chromatography using a gradient elution of hexanes with 25-100% EtOAc Providing 7-(5-phenyl-1H-imidazol-2-yl)-1-(4-(trifluoromethyl)phenylsulfonyl)-2,3-dihydro-1H-pyrido[2,3-b][1,4]oxazine (33 mg, 0.68 mmol, 86% yield) as a white/brown solid. LCMS (+ESI) m/z=487.0 $[M+H]^+$; $^1$H-NMR ($CDCl_3$) δ 8.69-8.67 (m, 2H), 7.82 (d, 2H), 7.75 (d, 2H), 7.72 (d, 2H), 7.42 (s, 1H), 7.36 (t, 2H) 7.26 (m, 2H) 3.95 (m, 2H), 3.84 (m, 2H).

Example 227

Preparation of 7-(5-phenyloxazol-2-yl)-1-(4-(trifluoromethyl)phenyl-sulfonyl)-2,3-dihydro-1H-pyrido[2,3-b][1,4]oxazine

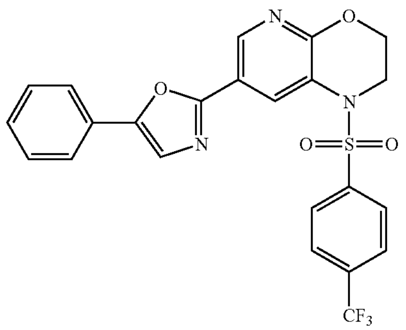

To a solution of N-(2-oxo-2-phenylethyl)-1-(4-(trifluoromethyl)phenylsulfonyl)-2,3-dihydro-1H-pyrido[2,3-b][1,4]oxazine-7-carboxamide (35 mg, 0.069 mmol) in THF was added Burgess reagent (33 mg, 0.138 mmol). The reaction was subjected to microwave irradiation (150° C., 5 min). Starting material was still present in the reaction mixture so additional Burgess reagent (33 mg, 0.138 mmol) was added. The reaction was resubjected to microwave irradiation (150° C., 5 min). The mixture was treated with saturated aqueous sodium bicarbonate (1 mL) and extracted with EtOAc (2×1 mL). The combined organic layers were dried over $Na_2SO_4$ and concentrated in vacuo. The residue was purified by flash column chromatography using a gradient elution of hexanes with 25-100% EtOAc, providing N-(2-oxo-2-phenylethyl)-1-(4-(trifluoromethyl)phenylsulfonyl)-2,3-dihydro-1H-pyrido[2,3-b][1,4]oxazine-7-carboxamide (25 mg, 0.051 mmol, 74% yield) as a white/brown solid. LCMS (+ESI) m/z=488.0 $[M+H]^+$.

Example 228

Determination of $EC_{50}$ values against the human CB2, rat CB2 and human CB1 receptors for the compounds of Examples 1-227

Screening Methods

Agonist or inverse agonist activity of each of the compounds at the human CB2 and CB1 receptors (hCB2, hCB1, respectively) and at the rat CB2 receptor (rCB2) was determined by measuring the change in intracellular cAMP level after exposure to the compound. Chinese Hamster Ovary (CHO-K1) cell lines stably expressing hCB2 (Genebank: X74328) or hCB1 (Genebank: X54937) were purchased from Euroscreen (Gosselies, Belgium). The rat CB2 receptor was expressed from genomic DNA (provided by M. Abood, California Pacific Medical Center) in CHO-K1 cells from expression plasmid vector, pcDNA3.1.

Cell lines were grown in suspension in EX-CELL 302 CHO Serum-free medium (Sigma, cat #14324C) supplemented with 1% Fetal Bovine Serum, glutamine and non-essential amino-acids under 0.4 mg/mL G418 selection. Receptor mediated responses were determined by measuring changes in intracellular cAMP using LANCE cAMP detection kit (cat #AD0264, PerkinElmer, Wellesley, Mass.) based on time-resolved fluorescence resonance energy transfer (TR-FRET). Changes in cAMP were determined in cells pre-incubated with IBMX (isobutyl methylxanthine) and pre-stimulated with NKH-477 (a water soluble forskolin derivative, cat #1603, Tocris, Ellisville, Mo.) to increase basal cAMP levels as detailed below.

On the day of the experiment, cells were spun at low speed for 5 min at room temperature. The supernatant was removed and cells were resuspended in stimulation buffer (Hanks Buffered Salt Solution/5 mM HEPES, containing 0.5 mM IBMX (cat # 17018, Sigma) and 0.02% BSA (PerkinElmer, cat #CR84-100). Cell clumps were removed by filtering through cell strainer 40 μm (BD Falcon, Discovery Labware, Bedford, Mass.) and diluted to $2\times10^5$ cells/mL. Antibody supplied with the LANCE cAMP immunoassay kit was then added according to the manufacturer's instructions. An aliquot of cells was taken for un-induced controls. To the remaining cells was added NKH-477 (a water soluble forskolin derivative, Tocris cat #1603) to a final concentration of 2-8 μM. Cells were then incubated for 30 min at room temperature prior to adding to Proxiplates containing test compounds (final DMSO concentration was less than 0.5%) with a Multidrop bulk dispenser, followed by a sixty minute incubation at room temperature. The response was stopped by addition of the detection mix supplied with the LANCE kit.

The reagents were allowed to equilibrate for three hours prior to reading on an Envision multi-mode detector (PerkinElmer). TR-FRET was measured using a 330-380 nm excitation filter, a 665 nm emission filter, dichroic mirror 380 nm and Z=1 mm.

Cyclic AMP concentrations in each well were back-calculated from a cAMP standard curve run concurrently during each assay. Each plate contained 16 wells of forskolin stimulated cells and 16 wells of forskolin plus CP55,940-treated cells. Cells were treated with 1 μM CP55,940 (Tocris cat. #0949). Concentrations of cAMP were expressed as a percent of the difference of these two groups of wells. Concentration-response data including $EC_{50}$ (the concentration of compound producing 50% of the maximal response) and intrinsic activity (the percent maximal activation compared to full activation by CP55,940) were determined using a four-parameter non-linear regression algorithm (Xlfit equation 251, IDBS).

Tables 8-10 below shows the distribution of $EC_{50}$ values of compounds as determined by the above method against the human CB1 and CB2 receptors and the rat CB2 receptor.

TABLE 8

| Distribution of $EC_{50}$ values for human CB2 receptor | |
|---|---|
| $EC_{50}$ | COMPOUND |
| ≦30 nM | 3, 7, 11, 24, 25, 55, 66, 151, 156, 167, 212, 218 |
| >30 nM-300 nM | 2, 8, 10, 13, 20, 21, 22, 23, 26, 27, 32, 33, 39, 40, 42, 43, 46, 48, 58, 59, 64, 65, 67, 69, 70, 71, 74, 92, 93, 95, 96, 99, 102, 106, 109, 113, 121, 124, 131, 136, 137, 138, 139, 146, 150, 152, 154*, 155, 157, 163, 164, 166, 168, 169, 170, 171, 172, 173, 180, 182, 183, 197, 200, 201, 209, 210, 211, 217, 221, 222, 223 |

TABLE 8-continued

| Distribution of $EC_{50}$ values for human CB2 receptor | |
|---|---|
| $EC_{50}$ | COMPOUND |
| >300 nM-3 μM | 1, 5, 9, 12, 14, 15*, 28, 29, 34, 35, 36, 37, 41, 44, 49, 50, 51, 54, 56, 57, 60, 62, 68, 72, 73, 75, 76, 77, 79, 82, 83, 85, 86, 89, 90, 97, 98, 101, 103, 104, 105, 107, 108, 110, 111, 112, 120, 122, 126, 127, 128, 129, 130, 132, 133, 140, 141, 142, 143, 147, 148, 149, 162*, 175, 178, 179, 181, 198, 204, 205, 213*, 214, 215, 216, 219, 220, 227 |
| >3 μM-30 μM | 16, 17, 47, 61, 100, 114, 123, 144, 145, 176, 199, 202, 203, 225 |
| AR | 4, 6, 18, 19, 30, 31, 38, 45, 52, 53, 63, 78, 80, 81, 84, 87, 88, 91, 94, 115, 116, 117, 118, 119, 125, 134, 135, 153, 158, 159, 160, 161, 165, 174, 177, 184, 185, 186, 187, 188, 189, 190, 191, 192, 193, 194, 195, 196, 206, 207, 208, 224, 226 |

AR: Above assay range, i.e. $EC_{50}$ > 30 μM or <30% efficacy;
Compounds marked with an asterisk (*) are inverse agonists

TABLE 9

| Distribution of $EC_{50}$ values for rat CB2 receptor | |
|---|---|
| $EC_{50}$ | COMPOUND |
| ≦30 nM | 2, 3, 6*, 7, 8, 10, 11, 12, 15*, 20, 21, 22, 23, 24, 25, 26, 27, 33, 39, 40, 42, 43, 46, 48, 55, 58, 59, 64, 65, 66, 67, 68, 69, 70, 71, 74, 83, 89, 90, 92, 95, 96, 97, 98, 99, 102, 103, 104, 109, 110, 111, 112, 113, 121, 124, 131, 132, 133, 135, 136, 137, 138, 139, 140, 142, 146, 148, 149, 150, 151, 152, 153*, 154*, 155, 156, 157, 163, 164, 166, 167, 168, 169, 170, 171, 172, 173, 178, 180, 182, 183, 184, 185, 186, 187, 191, 193, 194, 196, 197, 205, 209, 210, 212, 215, 216, 217, 218, 223, 227 |
| >30 nM-300 nM | 1, 5, 9, 13, 14, 28, 29, 32, 36, 37, 41, 47, 50, 51, 53, 54, 56, 57, 60, 62, 72, 77, 79, 82, 85, 86, 87, 88, 91, 93, 100, 101, 105, 106, 107, 108, 114, 117, 122, 126, 128, 129, 130, 141, 147, 162*, 165*, 179, 181, 188, 189, 190, 195, 200, 201, 202, 204, 211*, 214*, 220, 221, 222 |
| >300 nM-3 μM | 16, 17, 30, 31, 34, 35, 44, 49, 61, 63, 73, 75, 76, 80, 81, 84, 115, 118*, 120, 123, 125, 127, 134, 143, 145, 161, 174, 175, 176, 198, 199, 203, 208, 219, 224, 226* |
| >3 μM-30 μM | 18, 19, 38, 144, 158*, 159*, 213* |
| AR | 4, 45, 52, 78, 94, 116, 119, 160, 177, 192, 206, 207, 225 |

AR: Above assay range, i.e. $EC_{50}$ > 30 μM or <30% efficacy;
Compounds marked with an asterisk (*) are inverse agonists

TABLE 10

| Distribution of $EC_{50}$ values for human CB1 receptor | |
|---|---|
| $EC_{50}$ | COMPOUND |
| ≦300 nM | 153 |
| >300 nM-3 μM | 11, 24, 25, 42, 43*, 67, 117*, 121, 124, 131, 132, 148, 150, 151, 152, 154, 155, 165, 184, 185, 187, 188*, 212, 214, 217, 227 |
| >3 μM-30 μM | 2, 3, 5, 7, 8, 10, 39, 58, 61*, 69, 93*, 101, 102, 109, 110, 111, 112, 130*, 136, 141, 142, 149, 156, 157, 163, 164, 168, 173, 183, 195, 196, 205, 216 |
| AR | 1, 4, 6, 9, 12, 13, 14, 15, 16, 17, 18, 19, 20, 21, 22, 23, 26, 27, 28, 29, 30, 31, 32, 33, 34, 35, 36, 37, 38, 40, 41, 44, 45, 46, 47, 48, 49, 50, 51, 52, 53, 54, 55, 56, 57, 59, 60, 62, 63, 64, 65, 66, 68, 70, 71, 72, 73, 74, 75, 76, 77, 78, 79, 80, 81, 82, 83, 84, 85, 86, 87, 88, 89, 90, 91, 92, 94, 95, 96, 97, 98, 99, 100, 103, 104, 105, 106, 107, 108, 113, 114, 115, 116, 118, 119, 120, 122, 123, 125, 126, 127, 128, 129, 133, 134, 135, 137, 138, 139, 140, 143, 144, 145, 146, 147, 158, 159, 160, 161, 162, 166, 167, 169, 170, 171, 172, 174, 175, 176, 177, 178, 179, 180, 181, 182, 186, 189, 190, 191, 192, 193, 194, 197, 198, 199, 200, 201, 202, 203, 204, 206, 207, 208, 209, 210, 211, 213, 215, 218, 219, 220, 221, 222, 223, 224, 225, 226 |

AR: Above assay range, i.e. $EC_{50}$ > 30 μM or <30% efficacy;
Compounds marked with an asterisk (*) are inverse agonists The texts of the references cited in this specification are herein incorporated by reference in their entireties. In the event that a definition of a term as incorporated by reference differs from the meaning defined herein, then the meaning provided herein is intended. The examples provided herein are for illustration purposes only and are not to be interpreted as limiting the scope of the invention, the full scope of which will be immediately recognized by those of skill in the art.

We claim:

1. A compound of the structure of formula I

I

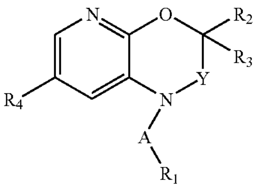

or a stereoisomer, racemate or salt thereof, wherein:

A is selected from the group consisting of $(CH_2)_n$, $CO(CH_2)_n$, and $SO_2(CH_2)_n$;

Y is selected from the group consisting of $CH_2$ and CO;

$R_1$ is selected from the group consisting of $C_1$-$C_6$ alkyl, $C_3$-$C_8$ cycloalkyl, —$NR_5R_6$, aryl, and 4- to 10-membered heterocyclyl, wherein the aryl of $R_1$ is optionally substituted with 1 to 5 substituents independently selected from the group consisting of halogen, $C_1$-$C_6$ alkyl, $C_1$-$C_6$ alkoxy, O-aryl, CN, $NO_2$, $OCF_3$, and $CF_3$; and the 5- to 10-membered heterocyclyl of $R_1$ is optionally substituted with 1 to 3 substituents independently selected from the group consisting of halogen, $C_1$-$C_6$ alkyl, $C_1$-$C_6$ alkoxy, CN, $NO_2$, $OCF_3$, and $CF_3$;

$R_2$ and $R_3$ are each independently selected from the group consisting of H and $C_1$-$C_3$ alkyl;

$R_4$ is $CONR_7R_8$, or

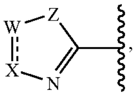

wherein W is selected from the group consisting of N, $NR_{17}$, O, $CR_9R_{10}$, $CR_9R_{10}CR_{11}R_{12}$, and $CR_{13}$; X is selected from the group consisting of N, $NR_{17}$, CO, $CR_{14}$, and $CR_{15}R_{16}$; and Z is selected from the group consisting of $NR_{17}$, O, and S;

$R_5$ and $R_6$ are independently selected from the group consisting of hydrogen, $C_1$-$C_6$ alkyl, $(CH_2)_nC_3$-$C_8$ cycloalkyl, $(CH_2)_n$aryl, $(CH_2)_n$-5- to 10-membered heterocyclyl, wherein the aryl of $(CH_2)_n$aryl and heterocycle of $(CH_2)_n$-5- to 10-membered heterocyclyl of $R_5$ and $R_6$ are each optionally substituted with 1 to 5 substituents independently selected from the group consisting of halogen, $C_1$-$C_6$ alkyl, CN, $OCF_3$, and $CF_3$; alternatively, $R_5$ and $R_6$, taken together with nitrogen atom to which they are bonded, form a 4- to 10-membered heterocyclyl optionally substituted with 1 to 4 substituents independently selected from the group consisting of halogen, $C_1$-$C_3$ alkyl, $CF_3$, aryl, 5- to 6-membered heterocyclyl, and $NR_{28}R_{29}$;

$R_7$ and $R_8$ are independently selected from the group consisting of H, $C_1$-$C_6$ alkyl, $(CH_2)_nC_3$-$C_8$ cycloalkyl, $(CH_2)_n$aryl, $(CH_2)_n$-4- to 10-membered heterocyclyl, and $(CH_2)_qCR_{18}R_{19}R_{20}$, wherein the $(CH_2)_n$aryl, $(CH_2)_n$-linked 4- to 10-membered heterocyclyl of $R_7$ and $R_8$ are each optionally substituted with 1 to 4 substituents independently selected from the group consisting of halogen, CN, $NO_2$, $CF_3$, $OCF_3$, $C_1$-$C_6$ alkyl, and $C_1$-$C_6$ alkoxy; alternatively, $R_7$ and $R_8$, taken together with nitrogen atom to which they are bonded, form a 4- to 10-membered heterocyclyl optionally substituted with 1 to 3 substituents independently selected from the group consisting of halogen, $CF_3$, $OCF_3$, $C_1$-$C_6$ alkyl, $C_1$-$C_6$ alkyl-$OR_{24}$, $COR_{24}$, $OR_{24}$, $(CH_2)_nCOOR_{24}$, $CONR_{24}R_{25}$, $(CH_2)_n$ $NR_{24}R_{25}$, $SO_2R_{24}$, $SO_2NR_{24}R_{25}$, and 5- to 6-membered heterocyclyl;

each instance of $R_9$, $R_{10}$, $R_{11}$, and $R_{12}$ is independently selected from the group consisting of H and $C_1$-$C_6$ alkyl;

$R_{13}$ is selected from the group consisting of H, $C_1$-$C_6$ alkyl, $(CH_2)_n$—$C_3$-$C_8$ cycloalkyl, and aryl;

$R_{14}$ is selected from the group consisting of H, $C_1$-$C_6$ alkyl, $CONR_{26}R_{27}$, and aryl, wherein the aryl of $R_{14}$ is optionally substituted with 1 to 4 substituents independently selected from the group consisting of halogen, $C_1$-$C_6$ alkyl, $C_1$-$C_6$ alkoxy, CN, $OCF_3$, and $CF_3$;

alternatively, $R_{13}$ and $R_{14}$, taken together with atoms to which they are bonded, form a 5- to 6-membered saturated, partially unsaturated, or unsaturated cycloalkyl, or a 5- to 7-membered heterocyclyl, each of which are optionally substituted with 1 to 3 substituents independently selected from the group consisting of halogen and $C_1$-$C_3$ alkyl;

each instance of $R_{15}$, $R_{16}$, and $R_{17}$ is independently selected from the group consisting of H and $C_1$-$C_6$ alkyl $R_{18}$ is selected from the group consisting of H, $C_1$-$C_6$ alkyl, CN, $COR_{21}$, $(CH_2)_mOR_{22}$, $(CH_2)_mNR_{22}R_{23}$, $(CH_2)_nCOOR_{22}$, and $(CH_2)_nCONR_{22}R_{23}$;

$R_{19}$ is selected from the group consisting of H, $C_1$-$C_6$ alkyl, $(CH_2)_nC_3$-$C_8$ cycloalkyl, and $(CH_2)_mOR_{22}$;

$R_{20}$ is selected from the group consisting of H, $C_1$-$C_6$ alkyl, $(CH_2)_nC_3$-$C_8$ cycloalkyl, and aryl;

$R_{21}$ is selected from the group consisting of H, $C_1$-$C_6$ alkyl, $(CH_2)_nC_3$-$C_8$ cycloalkyl, and aryl;

alternatively, (i) $R_{19}$ and $R_{20}$, taken together with the atom to which they are bonded, form a 3- to 6-membered cycloalkyl or 4- to 7-membered heterocyclyl; wherein the 3- to 6-membered cycloalkyl or 4- to 7-membered heterocyclyl are each optionally substituted with 1 to 2 substituents independently selected from the group consisting of halogen, $C_1$-$C_3$ alkyl, and $OR_{22}$; or (ii) $R_{20}$ and $R_{21}$, taken together with atoms to which they are bonded, form a 5- to 7-membered cycloalkyl or 5- to 7-membered heterocyclyl;

$R_{22}$ is selected from the group consisting of H, $C_1$-$C_6$ alkyl, and $(CH_2)_nC_3$-$C_8$ cycloalkyl;

$R_{23}$ is selected from the group consisting of H, $C_1$-$C_6$ alkyl, and $(CO)C_1$-$C_6$ alkyl;

alternatively, $R_{22}$ and $R_{23}$, taken together with the nitrogen atom to which they are bonded, form a 4- to 10-membered heterocyclyl optionally substituted with 1 to 3 substituents independently selected from the group consisting of halogen, $CF_3$, $OCF_3$, $C_1$-$C_6$ alkyl, $C_1$-$C_6$ alkoxy, and $SO_2$—$C_1$-$C_6$ alkyl;

$R_{24}$ is selected from the group consisting of H, $C_1$-$C_6$ alkyl, $(CH_2)_nC_3$-$C_8$ cycloalkyl, aryl, and 4- to 10-membered heterocyclyl, wherein the aryl and 4- to 10-membered heterocyclyl are each optionally substituted with 1 to 3 substituents independently selected from the group consisting of halogen, $CF_3$, $OCF_3$, $C_1$-$C_6$ alkyl, $C_1$-$C_6$ alkoxy;

$R_{25}$ is selected from the group consisting of H, $C_1$-$C_6$ alkyl, and CO—$C_1$-$C_6$ alkyl;

alternatively, $R_{24}$ and $R_{25}$, taken together with the nitrogen atom to which they are bonded, form a 4- to 10-membered heterocyclyl;

$R_{26}$ and $R_{27}$ are independently selected from the group consisting of H, $C_1$-$C_6$ alkyl, $(CH_2)_n$—$C_5$-$C_8$ cycloalkyl, and $C_2$-$C_8$ alkyloxyalkyl, or $R_{26}$ and $R_{27}$, taken together with nitrogen atom to which they are bonded, form a 5- to 9-membered heterocyclyl;

each instance of $R_{28}$ and $R_{29}$ is independently selected from the group consisting of H and $C_1$-$C_6$ alkyl; alternatively, $R_{28}$ and $R_{29}$, taken together with the nitrogen to which they are bonded, form a 4-6 membered heterocyclyl optionally substituted with 1 to 4 substituents independently selected from the group consisting of halogen and $C_1$-$C_6$ alkyl;

each instance of n, m and q is independently selected from 0 and an integer from 1 to 3;

provided that m and q are not both zero; and provided that if A is $SO_2$, $R_1$ is aryl or substituted aryl, and $R_7$ is H, then $R_8$ is not aryl, heteroaryl, substituted aryl, or substituted heteroaryl.

2. The compound according to claim 1, wherein A is $SO_2$.

3. The compound according to claim 1, wherein A is $CH_2$.

4. The compound according to claim 1, wherein:

$R_1$ is aryl, optionally substituted with 1 to 3 substituents independently selected from the group consisting of halogen, $C_1$-$C_6$ alkyl, $C_1$-$C_6$ alkoxy, and $CF_3$; and $R_2$ and $R_3$ are both H.

5. The compound according to claim 1, wherein $R_1$ is $NR_5R_6$.

6. The compound according to claim 5, wherein $R_5$ and $R_6$ are each independently selected from the group consisting of $C_1$-$C_6$ alkyl, $(CH_2)_n$aryl, 5- to 10-membered heterocyclyl, wherein the aryl of $(CH_2)_n$aryl and the 5- to 10-membered heterocyclyl of $R_5$ and $R_6$ are each optionally substituted with 1 to 5 substituents independently selected from the group consisting of halogen, $C_1$-$C_6$ alkyl, CN, $OCF_3$, and $CF_3$.

7. The compound according to claim 1, wherein $R_5$ and $R_6$, taken together with nitrogen atom to which they are bonded, form a 4- to 10-membered heterocyclyl optionally substituted with 1 to 4 substituents independently selected from the group consisting of halogen, $C_1$-$C_3$ alkyl, $CF_3$, aryl, 5- to 6-membered heterocyclyl, and $NR_{28}R_{29}$.

8. The compound according to claim 1, wherein $R_2$ and $R_3$ are both H; $R_4$ is $CONR_7R_8$, and $R_7$ is selected from the group consisting of H and $C_1$-$C_6$ alkyl.

9. The compound according to claim 1, wherein $R_2$ and $R_3$ are both H; and $R_4$ is

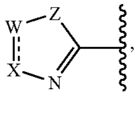

wherein X is selected from the group consisting of N, $CR_{14}$, and $CR_{15}R_{16}$; and Z is selected from the group consisting of $NR_{17}$ and O.

10. The compound according to claim 9, wherein $R_{13}$ and $R_{14}$, taken together with atoms to which they are bonded, form a 5- to 6-membered partially unsaturated, or unsaturated cycloalkyl, or a 5- to 7-membered heterocyclyl, each of which are optionally substituted with 1 to 3 substituents independently selected from the group consisting of halogen and $C_1$-$C_3$ alkyl.

11. The compound according to claim 9, wherein W is O and Z is NH.

12. The compound according to claim 9, wherein X is $CR_{14}$, and Z is N.

13. The compound according to claim 1, wherein

A is $SO_2$;

$R_1$ is aryl optionally substituted with 1 to 5 substituents independently chosen from halogen, $C_1$-$C_6$ alkyl, CN, $OCF_3$, and $CF_3$;

$R_2$ and $R_3$ are each independently selected from the group consisting of H and $CH_3$;

$R_4$ is $CONHR_8$; wherein $R_8$ is selected from the group consisting of $C_1$-$C_6$ alkyl, and $(CH_2)_qCR_{18}R_{19}R_{20}$; wherein $R_{18}$ is selected from the group consisting of $(CH_2)_mOR_{22}$, $(CH_2)_nCOOR_{22}$, and $(CH_2)_nCONR_{22}R_{23}$; and $R_{19}$ and $R_{20}$ are each independently $C_1$-$C_6$ alkyl.

14. The compound according to claim 1, wherein

A is $SO_2$;

$R_1$ is $NR_5R_6$;

$R_2$ and $R_3$ are each independently selected from the group consisting of H and $CH_3$;

$R_4$ is $CONHR_8$; wherein $R_8$ is selected from the group consisting of $C_1$-$C_6$ alkyl and $(CH_2)_qCR_{18}CR_{19}CR_{20}$; wherein $R_{18}$ is $(CH_2)_mOR_{22}$, $(CH_2)_nCOOR_{22}$, and $(CH_2)_nCONR_{22}R_{23}$; and $R_{19}$ and $R_{20}$ are each independently $C_1$-$C_6$ alkyl.

15. The compound according to claim 1, wherein

A is $SO_2$;

$R_1$ is selected from the group consisting of $C_1$-$C_6$ alkyl, aryl, haloaryl, and $CF_3$aryl;

$R_2$ and $R_3$ are each independently selected from the group consisting of H and $CH_3$; and $R_4$ is

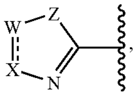

wherein X is selected from the group consisting of N, $CR_{14}$, and $CR_{15}R_{16}$; and Z is selected from the group consisting of $NR_{17}$ and O.

16. The compound according to claim 1, wherein

A is selected from the group consisting of $CH_2$ and $SO_2$;

$R_1$ is $NR_5R_6$;

$R_2$ and $R_3$ are each independently selected from the group consisting of H and $CH_3$; and $R_4$ is

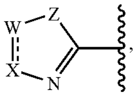

wherein X is selected from the group consisting of N, $CR_{14}$, and $CR_{15}R_{16}$; and Z is selected from the group consisting of $NR_{17}$ and O.

17. The compound according to claim 1, selected from the group consisting of (1-(phenylsulfonyl)-2,3-dihydro-1H-pyrido[2,3-b][1,4]oxazin-7-yl)(piperidin-1-yl)methanone;

N-tert-butyl-1-(piperidin-1-ylsulfonyl)-2,3-dihydro-1H-pyrido[2,3-b]-[1,4]oxazine-7-carboxamide;

N-tert-butyl-1-(4-cyanophenylsulfonyl)-2,3-dihydro-1H-pyrido[2,3-b][1,4]oxazine-7-carboxamide;

morpholino(1-(phenyl-sulfonyl)-2,3-dihydro-1H-pyrido[2,3-b][1,4]oxazin-7-yl)methanone;

N-tert-butyl-1-(phenyl-sulfonyl)-2,3-dihydro-1H-pyrido[2,3-b][1,4]oxazine-7-carboxamide;

(S)—N-(3,3-dimethyl-1-(methylamino)-1-oxobutan-2-yl)-1-(phenyl-sulfonyl)-2,3-dihydro-1H-pyrido[2,3-b][1,4]oxazine-7-carboxamide;

N-tert-butyl-1-(4-fluoro-phenylsulfonyl)-2,3-dihydro-1H-pyrido[2,3-b][1,4]oxazine-7-carboxamide;

1-(4-fluorophenyl-sulfonyl)-N-isobutyl-2,3-dihydro-1H-pyrido[2,3-b][1,4]oxazine-7-carboxamide;

1-(4-fluorophenyl-sulfonyl)-N-((tetrahydro-2H-pyran-4-yl)methyl)-2,3-dihydro-1H-pyrido[2,3-b][1,4]oxazine-7-carboxamide;

1-(4-fluorophenyl-sulfonyl)-N-neopentyl-2,3-dihydro-1H-pyrido[2,3-b][1,4]oxazine-7-carboxamide;

1-(4-fluorophenyl-sulfonyl)-N-(3-methoxypropyl)-2,3-dihydro-1H-pyrido[2,3-b][1,4]oxazine-7-carboxamide;

N-cyclopentyl-1-(4-fluorophenyl-sulfonyl)-2,3-dihydro-1H-pyrido[2,3-b][1,4]oxazine-7-carboxamide;

N,N-diethyl-1-(4-fluorophenylsulfonyl)-2,3-dihydro-1H-pyrido[2,3-b][1,4]oxazine-7-carboxamide;

1-(4-fluorophenyl-sulfonyl)-N-((tetrahydrofuran-2-yl)methyl)-2,3-dihydro-1H-pyrido[2,3-b][1,4]oxazine-7-carboxamide;

(S)—N-(3,3-dimethyl-1-(methylamino)-1-oxobutan-2-yl)-1-(4-fluorophenyl-sulfonyl)-2,3-dihydro-1H-pyrido[2,3-b][1,4]oxazine-7-carboxamide;

N-tert-butyl-1-(pyridin-3-ylsulfonyl)-2,3-dihydro-1H-pyrido[2,3-b][1,4]oxazine-7-carboxamide;

N-cyclopentyl-1-(pyridin-3-ylsulfonyl)-2,3-dihydro-1H-pyrido[2,3-b][1,4]oxazine-7-carboxamide;

N,N-diethyl-1-(pyridin-3-ylsulfonyl)-2,3-dihydro-1H-pyrido[2,3-b][1,4]oxazine-7-carboxamide;

N-(3-methoxypropyl)-1-(pyridin-3-ylsulfonyl)-2,3-dihydro-1H-pyrido[2,3-b][1,4]oxazine-7-carboxamide;

N-tert-butyl-1-(3-fluorophenylsulfonyl)-2,3-dihydro-1H-pyrido[2,3-b][1,4]oxazine-7-carboxamide;

N-cyclopentyl-1-(3-fluorophenylsulfonyl)-2,3-dihydro-1H-pyrido[2,3-b][1,4]oxazine-7-carboxamide;

N-tert-butyl-1-(2-fluorophenylsulfonyl)-2,3-dihydro-1H-pyrido[2,3-b][1,4]oxazine-7-carboxamide;

N-cyclopentyl-1-(2-fluorophenylsulfonyl)-2,3-dihydro-1H-pyrido[2,3-b][1,4]oxazine-7-carboxamide;

N-tert-butyl-1-(4-chlorophenylsulfonyl)-2,3-dihydro-1H-pyrido[2,3-b][1,4]oxazine-7-carboxamide;

1-(4-chlorophenyl-sulfonyl)-N-cyclopentyl-2,3-dihydro-1H-pyrido[2,3-b][1,4]oxazine-7-carboxamide;

N-tert-butyl-1-(4-(trifluoromethyl)phenylsulfonyl)-2,3-dihydro-1H-pyrido[2,3-b][1,4]oxazine-7-carboxamide;

N-cyclopentyl-1-(4-(trifluoromethyl)phenylsulfonyl)-2,3-dihydro-1H-pyrido[2,3-b][1,4]oxazine-7-carboxamide;

N-tert-butyl-1-(isobutylsulfonyl)-2,3-dihydro-1H-pyrido[2,3-b][1,4]oxazine-7-carboxamide;

N-cyclopentyl-1-(isobutylsulfonyl)-2,3-dihydro-1H-pyrido[2,3-b][1,4]oxazine-7-carboxamide;

N-tert-butyl-1-(1-methyl-1H-imidazol-4-ylsulfonyl)-2,3-dihydro-1H-pyrido-[2,3-b][1,4]oxazine-7-carboxamide;

N-cyclopentyl-1-(1-methyl-1H-imidazol-4-ylsulfonyl)-2,3-dihydro-1H-pyrido[2,3-b][1,4]oxazine-7-carboxamide;

N-benzyl-1-(4-fluorophenylsulfonyl)-N-methyl-2,3-dihydro-1H-pyrido[2,3-b][1,4]oxazine-7-carboxamide;

1-(4-chlorophenyl-sulfonyl)-N-(cyclopropyl-methyl)-2,3-dihydro-1H-pyrido[2,3-b][1,4]oxazine-7-carboxamide;

1-(4-chlorophenyl-sulfonyl)-N-(2-methoxy-ethyl)-N-methyl-2,3-dihydro-1H-pyrido-[2,3-b][1,4]oxazine-7-carboxamide;

N-(2-methoxyethyl)-N-methyl-1-(4-(trifluoro-methyl)phenylsulfonyl)-2,3-dihydro-1H-pyrido-[2,3-b][1,4]oxazine-7-carboxamide;

N-benzyl-N-methyl-1-(4-(trifluoromethyl)phenylsulfonyl)-2,3-dihydro-1H-pyrido-[2,3-b][1,4]oxazine-7-carboxamide;

N-(2-methyl-1-(pyrrolidin-1-yl)propan-2-yl)-1-(4-(trifluoromethyl)phenylsulfonyl)-2,3-dihydro-1H-pyrido[2,3-b][1,4]oxazine-7-carboxamide;

N-(2-(dimethylamino)-ethyl)-N-ethyl-1-(4-(trifluoromethyl)phenylsulfonyl)-2,3-dihydro-1H-pyrido[2,3-b][1,4]oxazine-7-carboxamide;

N-(1-hydroxy-2-methyl-propan-2-yl)-1-(4-(trifluoromethyl)phenylsulfonyl)-2,3-dihydro-1H-pyrido[2,3-b][1,4]oxazine-7-carboxamide;

N-tert-butyl-N-methyl-1-(4-(trifluoromethyl)-phenylsulfonyl)-2,3-dihydro-1H-pyrido[2,3-b][1,4]oxazine-7-carboxamide;

N-tert-butyl-N-(2-cyanoethyl)-1-(4-(trifluoromethyl)phenylsulfonyl)-2,3-dihydro-1H-pyrido[2,3-b][1,4]oxazine-7-carboxamide;

N-tert-butyl-N-ethyl-1-(4-(trifluoromethyl)phenylsulfonyl)-2,3-dihydro-1H-pyrido-[2,3-b][1,4]oxazine-7-carboxamide;

N-tert-butyl-N-(2-methoxyethyl)-1-(4-(trifluoromethyl)phenylsulfonyl)-2,3-dihydro-1H-pyrido[2,3-b][1,4]oxazine-7-carboxamide;

N-tert-butyl-N-(2-hydroxyethyl)-1-(4-(trifluoromethyl)phenylsulfonyl)-2,3-dihydro-1H-pyrido[2,3-b][1,4]oxazine-7-carboxamide;

N-(3-aminopropyl)-N-tert-butyl-1-(4-(trifluoromethyl)phenylsulfonyl)-2,3-dihydro-1H-pyrido[2,3-b][1,4]oxazine-7-carboxamide;

N-(2-methyl-1-morpholinopropan-2-yl)-1-(4-(trifluoromethyl)phenylsulfonyl)-2,3-dihydro-1H-pyrido[2,3-b][1,4]oxazine-7-carboxamide;

N-(2-amino-2-methylpropyl)-1-(4-(trifluoromethyl)phenylsulfonyl)-2,3-dihydro-1H-pyrido[2,3-b][1,4]oxazine-7-carboxamide;

N-tert-butyl-1-(4-(trifluoromethoxy)phenylsulfonyl)-2,3-dihydro-1H-pyrido[2,3-b][1,4]oxazine-7-carboxamide;

piperidin-1-yl(1-(4-(trifluoromethyl)phenylsulfonyl)-2,3-dihydro-1H-pyrido[2,3-b][1,4]oxazin-7-yl)methanone;

morpholino(1-(4-(trifluoromethyl)phenylsulfonyl)-2,3-dihydro-1H-pyrido[2,3-b][1,4]oxazin-7-yl)methanone;

N-(2-methoxyethyl)-1-(4-(trifluoromethyl)phenylsulfonyl)-2,3-dihydro-1H-pyrido-[2,3-b][1,4]oxazine-7-carboxamide;

1',1'-dioxide-thiomorpholino(1-(4-(trifluoromethyl)phenylsulfonyl)-2,3-dihydro-1H-pyrido[2,3-b][1,4]oxazin-7-yl)methanone;

N-tert-butyl-1-(3,5-dichlorophenylsulfonyl)-2,3-dihydro-1H-pyrido[2,3-b][1,4]oxazine-7-carboxamide;

N-tert-butyl-1-(2,4-dichlorophenylsulfonyl)-2,3-dihydro-1H-pyrido[2,3-b][1,4]oxazine-7-carboxamide;

N-tert-butyl-1-(3,4-dichlorophenylsulfonyl)-2,3-dihydro-1H-pyrido[2,3-b][1,4]oxazine-7-carboxamide;

N-tert-butyl-1-(4-fluoro-2-methylphenylsulfonyl)-2,3-dihydro-1H-pyrido[2,3-b][1,4]oxazine-7-carboxamide;

N-tert-butyl-1-(2-chloro-4-fluorophenylsulfonyl)-2,3-dihydro-1H-pyrido[2,3-b][1,4]oxazine-7-carboxamide;

(S)—N-(3,3-dimethyl-1-(methylamino)-1-oxobutan-2-yl)-1-(4-fluorophenylsulfonyl)-N-methyl-2,3-dihydro-1H-pyrido[2,3-b][1,4]oxazine-7-carboxamide;

N-tert-butyl-1-(5-methylthiophen-2-ylsulfonyl)-2,3-dihydro-1H-pyrido[2,3-b][1,4]oxazine-7-carboxamide;

1-(benzylsulfonyl)-N-tert-butyl-2,3-dihydro-1H-pyrido[2,3-b][1,4]oxazine-7-carboxamide;

N-tert-butyl-1-(4-chlorobenzylsulfonyl)-2,3-dihydro-1H-pyrido[2,3-b][1,4]oxazine-7-carboxamide;

N-tert-butyl-1-(4-fluorobenzylsulfonyl)-2,3-dihydro-1H-pyrido[2,3-b][1,4]oxazine-7-carboxamide;

N-tert-butyl-1-(4-(trifluoromethyl)benzylsulfonyl)-2,3-dihydro-1H-pyrido[2,3-b][1,4]oxazine-7-carboxamide;

N-(1-hydroxy-2-(hydroxymethyl)butan-2-yl)-1-(4-(trifluoromethyl)phenylsulfonyl)-2,3-dihydro-1H-pyrido[2,3-b][1,4]oxazine-7-carboxamide;

1-(4-(trifluoromethyl)-phenylsulfonyl)-N-(2,4,4-trimethylpentan-2-yl)-2,3-dihydro-1H-pyrido[2,3-b][1,4]oxazine-7-carboxamide;

N-tert-pentyl-1-(4-(trifluoromethyl)phenylsulfonyl)-2,3-dihydro-1H-pyrido[2,3-b]-[1,4]oxazine-7-carboxamide;

N-(1-(hydroxymethyl)-cyclopentyl)-1-(4-(trifluoromethyl)phenylsulfonyl)-2,3-dihydro-1H-pyrido[2,3-b][1,4]oxazine-7-carboxamide;

(S)-methyl 1-(1-(4-(trifluoromethyl)phenylsulfonyl)-2,3-dihydro-1H-pyrido[2,3-b][1,4]oxazine-7-carbonyl)piperidine-2-carboxylate;

(S)-(2-methylpiperidin-1-yl)(1-(4-(trifluoromethyl)-phenylsulfonyl)-2,3-dihydro-1H-pyrido[2,3-b][1,4]oxazin-7-yl)-methanone;

ethyl 1-(1-(4-(trifluoromethyl)phenylsulfonyl)-2,3-dihydro-1H-pyrido[2,3-b][1,4]oxazine-7-carboxamido)-cyclopropanecarboxylate;

ethyl 1-(1-(4-(trifluoro-methyl)phenylsulfonyl)-2,3-dihydro-1H-pyrido-[2,3-b][1,4]oxazine-7-carboxamido)cyclo-butanecarboxylate;

+/−(2-(hydroxymethyl)piperidin-1-yl)(1-(4-(trifluoromethyl)phenylsulfonyl)-2,3-dihydro-1H-pyrido[2,3-b][1,4]oxazin-7-yl)methanone;

+/−methyl 2-(1-(1-(4-(trifluoromethyl)phenylsulfonyl)-2,3-dihydro-1H-pyrido[2,3-b][1,4]oxazine-7-carbonyl)piperidin-2-yl)acetate;

+/−(2-(methoxymethyl)-piperidin-1-yl)(1-(4-(trifluoromethyl)phenylsulfonyl)-2,3-dihydro-1H-pyrido[2,3-b][1,4]oxazin-7-yl)methanone;

+/−(2-(pyrrolidin-1-ylmethyl)piperidin-1-yl)(1-(4-(trifluoromethyl)-phenylsulfonyl)-2,3-dihydro-1H-pyrido[2,3-b][1,4]oxazin-7-yl)-methanone;

+/−(2-(morpholino-methyl)piperidin-1-yl)(1-(4-(trifluoromethyl)-phenylsulfonyl)-2,3-dihydro-1H-pyrido[2,3-b][1,4]oxazin-7-yl)methanone;

N-(2-methyl-1-(piperidin-1-yl)propan-2-yl)-1-(4-(trifluoromethyl)phenylsulfonyl)-2,3-dihydro-1H-pyrido[2,3-b][1,4]oxazine-7-carboxamide;

(R)-1-(1-(4-(trifluoro-methyl)phenylsulfonyl)-2,3-dihydro-1H-pyrido-[2,3-b][1,4]oxazine-7-carbonyl)piperidine-2-carboxylic acid;

N-tert-butyl-1-(propylsulfonyl)-2,3-dihydro-1H-pyrido[2,3-b][1,4]oxazine-7-carboxamide;

N-tert-butyl-1-(ethylsulfonyl)-2,3-dihydro-1H-pyrido[2,3-b][1,4]oxazine-7-carboxamide;

N-tert-butyl-1-(3-methylbenzylsulfonyl)-2,3-dihydro-1H-pyrido[2,3-b][1,4]oxazine-7-carboxamide;

N-tert-butyl-1-(4-tert-butylphenylsulfonyl)-2,3-dihydro-1H-pyrido[2,3-b][1,4]oxazine-7-carboxamide;

N-tert-butyl-1-(3-(trifluoromethyl)phenylsulfonyl)-2,3-dihydro-1H-pyrido[2,3-b][1,4]oxazine-7-carboxamide;

N-tert-butyl-1-(2-(trifluoromethoxy)phenylsulfonyl)-2,3-dihydro-1H-pyrido[2,3-b][1,4]oxazine-7-carboxamide;

N-tert-butyl-1-(3-(trifluoromethoxy)phenylsulfonyl)-2,3-dihydro-1H-pyrido[2,3-b][1,4]oxazine-7-carboxamide;

N-tert-butyl-1-(m-tolylsulfonyl)-2,3-dihydro-1H-pyrido[2,3-b][1,4]oxazine-7-carboxamide;

N-tert-butyl-1-(naphthalen-1-ylsulfonyl)-2,3-dihydro-1H-pyrido[2,3-b][1,4]oxazine-7-carboxamide;

N-tert-butyl-1-(naphthalen-2-ylsulfonyl)-2,3-dihydro-1H-pyrido[2,3-b][1,4]oxazine-7-carboxamide;

N-tert-butyl-1-(3-chlorophenylsulfonyl)-2,3-dihydro-1H-pyrido[2,3-b][1,4]oxazine-7-carboxamide;

N-tert-butyl-1-(thiophen-3-ylsulfonyl)-2,3-dihydro-1H-pyrido[2,3-b][1,4]oxazine-7-carboxamide;

N-tert-butyl-1-(2,5-dimethylthiophen-3-ylsulfonyl)-2,3-dihydro-1H-pyrido[2,3-b][1,4]oxazine-7-carboxamide;

N-tert-butyl-1-(4-methylthiophen-2-ylsulfonyl)-2,3-dihydro-1H-pyrido[2,3-b][1,4]oxazine-7-carboxamide;

N-tert-butyl-1-(4-phenoxyphenylsulfonyl)-2,3-dihydro-1H-pyrido[2,3-b][1,4]oxazine-7-carboxamide;

N-tert-butyl-1-(5-chlorothiophen-2-ylsulfonyl)-2,3-dihydro-1H-pyrido[2,3-b][1,4]oxazine-7-carboxamide;

1-(3,4-dichlorophenylsulfonyl)-N-(1-hydroxy-2-methylpropan-2-yl)-2,3-dihydro-1H-pyrido[2,3-b][1,4]oxazine-7-carboxamide;

1-(4-chloro-2-fluorophenylsulfonyl)-N-(1-hydroxy-2-methylpropan-2-yl)-2,3-dihydro-1H-pyrido[2,3-b][1,4]oxazine-7-carboxamide;

1-(4-chloro-2-fluorophenylsulfonyl)-N-(2-hydroxy-2-methylpropyl)-2,3-dihydro-1H-pyrido[2,3-b][1,4]oxazine-7-carboxamide;

1-(3,4-dichlorophenylsulfonyl)-N-(2-hydroxy-2-methylpropyl)-2,3-dihydro-1H-pyrido[2,3-b][1,4]oxazine-7-carboxamide;

1-(3-chloro-4-fluorophenylsulfonyl)-N-(1-hydroxy-2-methylpropan-2-yl)-2,3-dihydro-1H-pyrido[2,3-b][1,4]oxazine-7-carboxamide;

1-(3-chloro-4-methoxyphenylsulfonyl)-N-(1-hydroxy-2-methylpropan-2-yl)-2,3-dihydro-1H-pyrido[2,3-b][1,4]oxazine-7-carboxamide;

1-(3-fluoro-4-methoxyphenylsulfonyl)-N-(1-hydroxy-2-methylpropan-2-yl)-2,3-dihydro-1H-pyrido[2,3-b][1,4]oxazine-7-carboxamide;

1-(2,4-difluorophenylsulfonyl)-N-(1-hydroxy-2-methylpropan-2-yl)-2,3-dihydro-1H-pyrido[2,3-b][1,4]oxazine-7-carboxamide;

1-(2-fluoro-4-methoxyphenylsulfonyl)-N-(1-hydroxy-2-methylpropan-2-yl)-2,3-dihydro-1H-pyrido[2,3-b][1,4]oxazine-7-carboxamide;

1-(3-chloro-4-methoxyphenylsulfonyl)-N-(2-hydroxy-2-methylpropyl)-2,3-dihydro-1H-pyrido[2,3-b][1,4]oxazine-7-carboxamide;

1-(3-fluoro-4-methoxyphenylsulfonyl)-N-(2-hydroxy-2-methylpropyl)-2,3-dihydro-1H-pyrido[2,3-b][1,4]oxazine-7-carboxamide;

1-(2,4-difluorophenylsulfonyl)-N-(2-hydroxy-2-methylpropyl)-2,3-dihydro-1H-pyrido[2,3-b][1,4]oxazine-7-carboxamide;

1-(2-fluoro-4-methoxyphenylsulfonyl)-N-(2-hydroxy-2-methylpropyl)-2,3-dihydro-1H-pyrido[2,3-b][1,4]oxazine-7-carboxamide;

1-(3-chloro-4-fluorophenylsulfonyl)-N-(2-hydroxy-2-methylpropyl)-2,3-dihydro-1H-pyrido[2,3-b][1,4]oxazine-7-carboxamide;

1-(3,4-difluorophenylsulfonyl)-N-(2-hydroxy-2-methylpropyl)-2,3-dihydro-1H-pyrido[2,3-b][1,4]oxazine-7-carboxamide;

1-(3,4-dichlorophenylsulfonyl)-N-((1S,2S)-2-hydroxycyclopentyl)-2,3-dihydro-1H-pyrido[2,3-b][1,4]oxazine-7-carboxamide;

1-(4-chloro-2-fluorophenylsulfonyl)-N-((1S,2S)-2-hydroxycyclopentyl)-2,3-dihydro-1H-pyrido[2,3-b][1,4]oxazine-7-carboxamide;

1-(3,4-dichlorophenylsulfonyl)-N-(2-methyl-1-morpholinopropan-2-yl)-2,3-dihydro-1H-pyrido[2,3-b][1,4]oxazine-7-carboxamide;

1-(4-chloro-2-fluorophenylsulfonyl)-N-(2-methyl-1-morpholinopropan-2-yl)-2,3-dihydro-1H-pyrido[2,3-b][1,4]oxazine-7-carboxamide;

1-(3,4-dichlorophenyl-sulfonyl)-N-(2-hydroxyethyl)-2,3-dihydro-1H-pyrido[2,3-b][1,4]oxazine-7-carboxamide;

1-(4-chloro-2-fluorophenylsulfonyl)-N-(2-hydroxyethyl)-2,3-dihydro-1H-pyrido[2,3-b][1,4]oxazine-7-carboxamide;

(1-(3,4-dichloro-phenylsulfonyl)-2,3-dihydro-1H-pyrido[2,3-b][1,4]oxazin-7-yl)(4-(methylsulfonyl)piperazin-1-yl)methanone;

(1-(3,4-dichlorophenyl-sulfonyl)-2,3-dihydro-1H-pyrido[2,3-b][1,4]oxazin-7-yl)(4-(pyridin-2-ylsulfonyl)piperazin-1-yl)methanone;

(1-(3,4-dichlorophenyl-sulfonyl)-2,3-dihydro-1H-pyrido[2,3-b][1,4]oxazin-7-yl)(4-(phenylsulfonyl)piperazin-1-yl)methanone;

4-(1-(3,4-dichlorophenylsulfonyl)-2,3-dihydro-1H-pyrido[2,3-b][1,4]oxazine-7-carbonyl)-N,N-dimethyl piperazine-1-sulfonamide;

1-(3,4-dichlorophenyl-sulfonyl)-N-(2-hydroxy-ethyl)-N-methyl-2,3-dihydro-1H-pyrido[2,3-b][1,4]oxazine-7-carboxamide;

1-(3,4-dichlorophenyl sulfonyl)-N-(3-hydroxy-2,2-dimethylpropyl)-N-methyl-2,3-dihydro-1H-pyrido[2,3-b][1,4]oxazine-7-carboxamide;

(R)-(1-(3,4-dichlorophenyl sulfonyl)-2,3-dihydro-1H-pyrido[2,3-b][1,4]oxazin-7-yl)(2-(hydroxymethyl)pyrrolidin-1-yl)methanone;

(1-(3,4-dichlorophenyl-sulfonyl)-2,3-dihydro-1H-pyrido[2,3-b][1,4]oxazin-7-yl)(4-methylpiperazin-1-yl)methanone;

(1-(3,4-dichlorophenyl-sulfonyl)-2,3-dihydro-1H-pyrido[2,3-b][1,4]oxazin-7-yl)(4,4-dimethyl-oxazolidin-3-yl)methanone;

(1-(3,4-dichlorophenyl-sulfonyl)-2,3-dihydro-1H-pyrido[2,3-b][1,4]oxazin-7-yl)(3-hydroxyazetidin-1-yl)methanone;

(1-(3,4-dichlorophenyl-sulfonyl)-2,3-dihydro-1H-pyrido[2,3-b][1,4]oxazin-7-yl)(3,3-difluoro-pyrrolidin-1-yl)methanone;

(1-(3,4-dichlorophenyl-sulfonyl)-2,3-dihydro-1H-pyrido[2,3-b][1,4]oxazin-7-yl)(4-hydroxypiperidin-1-yl)methanone;

(1-(3,4-dichlorophenyl-sulfonyl)-2,3-dihydro-1H-pyrido[2,3-b][1,4]oxazin-7-yl)(3,3-difluoroazetidin-1-yl)methanone;

(1-(3,4-dichlorophenyl-sulfonyl)-2,3-dihydro-1H-pyrido[2,3-b][1,4]oxazin-7-yl)(3-methoxyazetidin-1-yl)methanone;

azetidin-1-yl(1-(3,4-dichlorophenylsulfonyl)-2,3-dihydro-1H-pyrido[2,3-b][1,4]oxazin-7-yl)methanone;

1-(3,4-dichlorophenyl-sulfonyl)-N-(3-hydroxy-2,2-dimethylpropyl)-2,3-dihydro-1H-pyrido[2,3-b][1,4]oxazine-7-carboxamide;

1-(3,4-dichlorophenyl-sulfonyl)-N-((1S,2R)-2-hydroxycyclopentyl)-2,3-dihydro-1H-pyrido[2,3-b][1,4]oxazine-7-carboxamide;

1-(3,4-dichlorophenyl-sulfonyl)-N-((1R,2R)-2-hydroxycyclopentyl)-2,3-dihydro-1H-pyrido[2,3-b][1,4]oxazine-7-carboxamide;

1-(3,4-dichlorophenyl-sulfonyl)-N-(trans-4-hydroxycyclohexyl)-2,3-dihydro-1H-pyrido[2,3-b][1,4]oxazine-7-carboxamide;

1-(3,4-dichlorophenyl-sulfonyl)-N-((1R,2R)-2-hydroxycyclohexyl)-2,3-dihydro-1H-pyrido[2,3-b][1,4]oxazine-7-carboxamide;

methyl 2-(1-(3,4-dichlorophenylsulfonyl)-2,3-dihydro-1H-pyrido[2,3-b][1,4]oxazine-7-carboxamido)-2-methylpropanoate;

N-cyclobutyl-1-(3,4-dichlorophenylsulfonyl)-2,3-dihydro-1H-pyrido[2,3-b][1,4]oxazine-7-carboxamide;

N-benzyl-1-(3,4-dichlorophenylsulfonyl)-2,3-dihydro-1H-pyrido[2,3-b][1,4]oxazine-7-carboxamide;

ethyl 1-(1-(3,4-dichloro-phenylsulfonyl)-2,3-dihydro-1H-pyrido[2,3-b][1,4]oxazine-7-carboxamido)cyclobutanecarboxylate;

N-tert-butyl-1-(morpholinosulfonyl)-2,3-dihydro-1H-pyrido[2,3-b][1,4]oxazine-7-carboxamide;

N-(3-hydroxy-2,2-dimethylpropyl)-1-(morpholinosulfonyl)-2,3-dihydro-1H-pyrido-[2,3-b][1,4]oxazine-7-carboxamide;

1-(morpholinosulfonyl)-N-tert-pentyl-2,3-dihydro-1H-pyrido[2,3-b][1,4]oxazine-7-carboxamide 1-(N,N-dimethyl-sulfamoyl)-N-tert-pentyl-2,3-dihydro-1H-pyrido[2,3-b][1,4]oxazine-7-carboxamide;

1-(N,N-dimethyl-sulfamoyl)-N-(1-hydroxy-2-methylpropan-2-yl)-2,3-dihydro-1H-pyrido[2,3-b][1,4]oxazine-7-carboxamide;

N-tert-butyl-1-(N,N-dimethylsulfamoyl)-2,3-dihydro-1H-pyrido[2,3-b][1,4]oxazine-7-carboxamide;

N-(1-hydroxy-2-methylpropan-2-yl)-1-(piperidin-1-ylsulfonyl)-2,3-dihydro-1H-pyrido[2,3-b][1,4]oxazine-7-carboxamide;

N-(2-methyl-1-morpholinopropan-2-yl)-1-(piperidin-1-ylsulfonyl)-2,3-dihydro-1H-pyrido[2,3-b][1,4]oxazine-7-carboxamide;

N-tert-butyl-1-(pyrrolidin-1-ylsulfonyl)-2,3-dihydro-1H-pyrido[2,3-b][1,4]oxazine-7-carboxamide;

N-(1-hydroxy-2-methylpropan-2-yl)-1-(pyrrolidin-1-ylsulfonyl)-2,3-dihydro-1H-pyrido[2,3-b][1,4]oxazine-7-carboxamide;

N-tert-butyl-1-(4-(trifluoromethyl)piperidin-1-ylsulfonyl)-2,3-dihydro-1H-pyrido-[2,3-b][1,4]oxazine-7-carboxamide;

N-tert-pentyl-1-(4-(trifluoromethyl)piperidin-1-ylsulfonyl)-2,3-dihydro-1H-pyrido-[2,3-b][1,4]oxazine-7-carboxamide;

N-(1-hydroxy-2-methylpropan-2-yl)-1-(4-(trifluoromethyl)piperidin-1-ylsulfonyl)-2,3-dihydro-1H-pyrido[2,3-b][1,4]oxazine-7-carboxamide;

N-(3-tert-butylisoxazol-5-yl)-1-(4-(trifluoromethyl)piperidin-1-ylsulfonyl)-2,3-dihydro-1H-pyrido[2,3-b][1,4]oxazine-7-carboxamide;

N-(5-tert-butylisoxazol-3-yl)-1-(4-(trifluoromethyl)piperidin-1-ylsulfonyl)-2,3-dihydro-1H-pyrido[2,3-b][1,4]oxazine-7-carboxamide;

N-(3-hydroxy-2,2-dimethylpropyl)-1-(4-(trifluoromethyl)piperidin-1-ylsulfonyl)-2,3-dihydro-1H-pyrido[2,3-b][1,4]oxazine-7-carboxamide;

N-tert-butyl-1-(4,4-difluoropiperidin-1-ylsulfonyl)-2,3-dihydro-1H-pyrido[2,3-b][1,4]oxazine-7-carboxamide;

1-(4,4-difluoropiperidin-1-ylsulfonyl)-N-(1-hydroxy-2-methylpropan-2-yl)-2,3-dihydro-1H-pyrido[2,3-b][1,4]oxazine-7-carboxamide;

N-tert-butyl-1-(4-phenylpiperidin-1-ylsulfonyl)-2,3-dihydro-1H-pyrido[2,3-b][1,4]oxazine-7-carboxamide;

N-tert-pentyl-1-(4-phenylpiperidin-1-ylsulfonyl)-2,3-dihydro-1H-pyrido[2,3-b][1,4]oxazine-7-carboxamide;

N-(1-hydroxy-2-methylpropan-2-yl)-1-(4-phenylpiperidin-1-ylsulfonyl)-2,3-dihydro-1H-pyrido[2,3-b][1,4]oxazine-7-carboxamide;

N-(3-hydroxy-2,2-dimethylpropyl)-1-(4-phenylpiperidin-1-ylsulfonyl)-2,3-dihydro-1H-pyrido[2,3-b][1,4]oxazine-7-carboxamide;

N-(5-tert-butylisoxazol-3-yl)-1-(4-phenylpiperidin-1-ylsulfonyl)-2,3-dihydro-1H-pyrido[2,3-b][1,4]oxazine-7-carboxamide;

N-tert-butyl-1-(3,3-difluoropyrrolidin-1-ylsulfonyl)-2,3-dihydro-1H-pyrido[2,3-b][1,4]oxazine-7-carboxamide;

1-(3,3-difluoropyrrolidin-1-ylsulfonyl)-N-tert-pentyl-2,3-dihydro-1H-pyrido[2,3-b][1,4]oxazine-7-carboxamide;

N-(5-tert-butylisoxazol-3-yl)-1-(3,3-difluoro-pyrrolidin-1-ylsulfonyl)-2,3-dihydro-1H-pyrido-[2,3-b][1,4]oxazine-7-carboxamide;

N-tert-butyl-1-(4-fluoropiperidin-1-ylsulfonyl)-2,3-dihydro-1H-pyrido[2,3-b][1,4]oxazine-7-carboxamide;

1-(4-fluoropiperidin-1-ylsulfonyl)-N-tert-pentyl-2,3-dihydro-1H-pyrido[2,3-b][1,4]oxazine-7-carboxamide;

1-(4-fluoropiperidin-1-ylsulfonyl)-N-(1-hydroxy-2-methylpropan-2-yl)-2,3-dihydro-1H-pyrido[2,3-b][1,4]oxazine-7-carboxamide;

1-(4-fluoropiperidin-1-ylsulfonyl)-N-(3-hydroxy-2,2-dimethylpropyl)-2,3-dihydro-1H-pyrido[2,3-b][1,4]oxazine-7-carboxamide;

N-tert-butyl-1-(4-methylpiperidin-1-ylsulfonyl)-2,3-dihydro-1H-pyrido[2,3-b][1,4]oxazine-7-carboxamide;

1-(4-methylpiperidin-1-ylsulfonyl)-N-tert-pentyl-2,3-dihydro-1H-pyrido[2,3-b][1,4]oxazine-7-carboxamide;

N-(1-hydroxy-2-methylpropan-2-yl)-1-(4-methylpiperidin-1-ylsulfonyl)-2,3-dihydro-1H-pyrido[2,3-b][1,4]oxazine-7-carboxamide;

N-(3-hydroxy-2,2-dimethylpropyl)-1-(4-methylpiperidin-1-ylsulfonyl)-2,3-dihydro-1H-pyrido[2,3-b][1,4]oxazine-7-carboxamide;

N-tert-butyl-1-(4-methylpiperazin-1-ylsulfonyl)-2,3-dihydro-1H-pyrido[2,3-b][1,4]oxazine-7-carboxamide;

1-(4-methylpiperazin-1-ylsulfonyl)-N-tert-pentyl-2,3-dihydro-1H-pyrido[2,3-b][1,4]oxazine-7-carboxamide;

N-tert-butyl-1-(4-(pyrrolidin-1-yl)piperidin-1-ylsulfonyl)-2,3-dihydro-1H-pyrido[2,3-b][1,4]oxazine-7-carboxamide;

N-tert-pentyl-1-(4-(pyrrolidin-1-yl)piperidin-1-ylsulfonyl)-2,3-dihydro-1H-pyrido-[2,3-b][1,4]oxazine-7-carboxamide;

1-(N-benzylsulfamoyl)-N-tert-butyl-2,3-dihydro-1H-pyrido[2,3-b][1,4]oxazine-7-carboxamide;

1-(N-benzylsulfamoyl)-N-(1-hydroxy-2-methylpropan-2-yl)-2,3-dihydro-1H-pyrido-[2,3-b][1,4]oxazine-7-carboxamide;

N-tert-butyl-1-(N-isobutylsulfamoyl)-2,3-dihydro-1H-pyrido[2,3-b][1,4]oxazine-7-carboxamide;

N-(1-hydroxy-2-methylpropan-2-yl)-1-(N-isobutylsulfamoyl)-2,3-dihydro-1H-pyrido[2,3-b][1,4]oxazine-7-carboxamide;

N-(3-hydroxy-2,2-dimethylpropyl)-1-(N-isobutylsulfamoyl)-2,3-dihydro-1H-pyrido-[2,3-b][1,4]oxazine-7-carboxamide;

N-tert-butyl-1-(isoindolin-2-ylsulfonyl)-2,3-dihydro-1H-pyrido[2,3-b][1,4]oxazine-7-carboxamide;

N-tert-butyl-1-(4-chloropiperidin-1-ylsulfonyl)-2,3-dihydro-1H-pyrido[2,3-b][1,4]oxazine-7-carboxamide;

1-(4-chloropiperidin-1-ylsulfonyl)-N-tert-pentyl-2,3-dihydro-1H-pyrido[2,3-b][1,4]oxazine-7-carboxamide;

1-(4-chloropiperidin-1-ylsulfonyl)-N-(1-hydroxy-2-methylpropan-2-yl)-2,3-dihydro-1H-pyrido[2,3-b][1,4]oxazine-7-carboxamide;

1-(4-chloropiperidin-1-ylsulfonyl)-N-(3-hydroxy-2,2-dimethylpropyl)-2,3-dihydro-1H-pyrido[2,3-b][1,4]oxazine-7-carboxamide;

N-tert-butyl-1-(3,4-dihydroisoquinolin-2(1H)-ylsulfonyl)-2,3-dihydro-1H-pyrido[2,3-b][1,4]oxazine-7-carboxamide;

1-(3,4-dihydroisoquinolin-2(1H)-ylsulfonyl)-N-tert-pentyl-2,3-dihydro-1H-pyrido-[2,3-b][1,4]oxazine-7-carboxamide;

1-(3,4-dihydroisoquinolin-2(1H)-ylsulfonyl)-N-(1-hydroxy-2-methylpropan-2-yl)-2,3-dihydro-1H-pyrido[2,3-b][1,4]oxazine-7-carboxamide;

1-(3,4-dihydroisoquinolin-2(1H)-ylsulfonyl)-N-(3-hydroxy-2,2-dimethylpropyl)-2,3-dihydro-1H-pyrido[2,3-b][1,4]oxazine-7-carboxamide;

1-(3,4-dihydroisoquinolin-2(1H)-ylsulfonyl)-N-(3-hydroxy-2,2-dimethyl-propyl)-N-methyl-2,3-dihydro-1H-pyrido[2,3-b][1,4]oxazine-7-carboxamide;

N-tert-butyl-1-(3,3-difluoroazetidin-1-ylsulfonyl)-2,3-dihydro-1H-pyrido[2,3-b][1,4]oxazine-7-carboxamide;

1-(3,3-difluoroazetidin-1-ylsulfonyl)-N-tert-pentyl-2,3-dihydro-1H-pyrido[2,3-b][1,4]oxazine-7-carboxamide;

1-(3,3-difluoroazetidin-1-ylsulfonyl)-N-(1-hydroxy-2-methylpropan-2-yl)-2,3-dihydro-1H-pyrido[2,3-b][1,4]oxazine-7-carboxamide;

1-(3,3-difluoroazetidin-1-ylsulfonyl)-N-(3-hydroxy-2,2-dimethylpropyl)-2,3-dihydro-1H-pyrido[2,3-b][1,4]oxazine-7-carboxamide;

(cis-2,6-dimethylpiperidin-1-yl)(1-(4-(trifluoromethyl)phenylsulfonyl)-2,3-dihydro-1H-pyrido[2,3-b][1,4]oxazin-7-yl)methanone;

(2,6-dimethylmorpholino)(1-(4-(trifluoromethyl)phenylsulfonyl)-2,3-dihydro-1H-pyrido[2,3-b][1,4]oxazin-7-yl)methanone;

(2,6-dimethylmorpholino)(1-(4-(trifluoromethyl)phenylsulfonyl)-2,3-dihydro-1H-pyrido[2,3-b][1,4]oxazin-7-yl)methanone;

(3,5-dimethylpiperidin-1-yl)(1-(4-(trifluoromethyl)phenylsulfonyl)-2,3-dihydro-1H-pyrido[2,3-b][1,4]oxazin-7-yl)methanone;

(3,5-dimethylpiperidin-1-yl)(1-(4-(trifluoromethyl)phenylsulfonyl)-2,3-dihydro-1H-pyrido[2,3-b][1,4]oxazin-7-yl)methanone;

methyl 4-(1-(3,4-dichlorophenylsulfonyl)-2,3-dihydro-1H-pyrido[2,3-b][1,4]oxazine-7-carboxamido)tetrahydro-2H-pyran-4-carboxylate;

1-(1-(4-(trifluoromethyl)phenylsulfonyl)-2,3-dihydro-1H-pyrido[2,3-b][1,4]oxazine-7-carboxamido)cyclopropanecarboxylic acid;

2-(1-(1-(4-(trifluoromethyl)phenylsulfonyl)-2,3-dihydro-1H-pyrido[2,3-b][1,4]oxazine-7-carbonyl)piperidin-2-yl)acetic acid;

1-(1-(4-(trifluoromethyl)phenylsulfonyl)-2,3-dihydro-1H-pyrido[2,3-b][1,4]oxazine-7-carboxamido)cyclobutanecarboxylic acid;

1-(3,4-dichlorophenylsulfonyl)-N-(1-(hydroxymethyl)cyclobutyl)-2,3-dihydro-1H-pyrido[2,3-b][1,4]oxazine-7-carboxamide;

7-(3-ethyl-1,2,4-oxadiazol-5-yl)-1-(phenylsulfonyl)-2,3-dihydro-1H-pyrido[2,3-b][1,4]oxazine;

7-(5-phenyl-1,3,4-oxadiazol-2-yl)-1-(phenylsulfonyl)-2,3-dihydro-1H-pyrido[2,3-b][1,4]oxazine;

7-(5-tert-butyl-1,3,4-oxadiazol-2-yl)-1-(4-fluorophenylsulfonyl)-2,3-dihydro-1H-pyrido[2,3-b][1,4]oxazine;

N-cyclopentyl-5-(1-(4-fluorophenylsulfonyl)-2,3-dihydro-1H-pyrido[2,3-b][1,4]oxazin-7-yl)-1,2,4-oxadiazole-3-carboxamide;

N-tert-butyl-5-(1-(4-fluoro-phenyl sulfonyl)-2,3-dihydro-1H-pyrido[2,3-b][1,4]oxazin-7-yl)-1,2,4-oxadiazole-3-carboxamide;

(5-(1-(4-fluorophenyl-sulfonyl)-2,3-dihydro-1H-pyrido[2,3-b][1,4]oxazin-7-yl)-1,2,4-oxadiazol-3-yl)(morpholino)methanone;

5-(1-(4-fluorophenylsulfonyl)-2,3-dihydro-1H-pyrido[2,3-b][1,4]oxazin-7-yl)-N-(3-methoxypropyl)-1,2,4-oxadiazole-3-carboxamide;

7-(oxazolo[4,5-b]pyridin-2-yl)-1-(phenylsulfonyl)-2,3-dihydro-1H-pyrido[2,3-b][1,4]oxazine;

N-tert-butyl-1-(4-fluorobenzyl)-2-oxo-2,3-dihydro-1H-pyrido[2,3-b][1,4]oxazine-7-carboxamide;

1-benzyl-N-cyclopentyl-2-oxo-2,3-dihydro-1H-pyrido[2,3-b][1,4]oxazine-7-carboxamide;

1-benzyl-N-tert-butyl-2-oxo-2,3-dihydro-1H-pyrido[2,3-b][1,4]oxazine-7-carboxamide;

N-cyclopentyl-1-(4-fluorobenzyl)-2-oxo-2,3-dihydro-1H-pyrido[2,3-b][1,4]oxazine-7-carboxamide;

1-(4-chlorobenzyl)-N-cyclopentyl-2-oxo-2,3-dihydro-1H-pyrido[2,3-b][1,4]oxazine-7-carboxamide;

7-(5,5-dimethyl-2,5-dihydro-1,2,4-oxadiazol-3-yl)-1-(4-(trifluoromethyl)phenylsulfonyl)-2,3-dihydro-1H-pyrido[2,3-b][1,4]oxazine;

7-(4,4-dimethyl-4,5-dihydro-1H-imidazol-2-yl)-1-(4-(trifluoromethyl)phenylsulfonyl)-2,3-dihydro-1H-pyrido[2,3-b][1,4]oxazine;

7-(5,5-dimethyl-1,4,5,6-tetrahydropyrimidin-2-yl)-1-(4-(trifluoromethyl)phenylsulfonyl)-2,3-dihydro-1H-pyrido[2,3-b][1,4]oxazine;

7-(5-phenyl-1H-imidazol-2-yl)-1-(4-(trifluoromethyl)phenylsulfonyl)-2,3-dihydro-1H-pyrido[2,3-b][1,4]oxazine; and 7-(5-phenyloxazol-2-yl)-1-(4-(trifluoromethyl)phenylsulfonyl)-2,3-dihydro-1H-pyrido[2,3-b][1,4]oxazine.

18. A pharmaceutical composition comprising a compound according to claim 1 and a pharmaceutically acceptable diluent, excipient, or carrier.

19. The compound according to claim 1, selected from the group consisting of N-tert-pentyl-1-(4-(trifluoromethyl)piperidin-1-ylsulfonyl)-2,3-dihydro-1H-pyrido[2,3-b][1,4]oxazine-7-carboxamide;

N-tert-butyl-1-(4,4-difluoropiperidin-1-ylsulfonyl)-2,3-dihydro-1H-pyrido[2,3-b][1,4]oxazine-7-carboxamide;

1-(4-fluoropiperidin-1-ylsulfonyl)-N-tert-pentyl-2,3-dihydro-1H-pyrido[2,3-b][1,4]oxazine-7-carboxamide;

7-(5-tert-butyl-1,3,4-oxadiazol-2-yl)-1-(4-fluorophenylsulfonyl)-2,3-dihydro-1H-pyrido[2,3-b][1,4]oxazine; and N-tert-butyl-1-(4-fluorobenzyl)-2-oxo-2,3-dihydro-1H-pyrido[2,3-b][1,4]oxazine-7-carboxamide.

20. The compound according to claim 1, having the structure defined by N-(3-tert-butylisoxazol-5-yl)-1-(4-(trifluoromethyl)piperidin-1-ylsulfonyl)-2,3-dihydro-1H-pyrido[2,3-b][1,4]oxazine-7-carboxamide.

* * * * *